US011136384B2

(12) United States Patent
Dupont et al.

(10) Patent No.: US 11,136,384 B2
(45) Date of Patent: *Oct. 5, 2021

(54) METHODS FOR TREATMENT OF CANCER COMPRISING TIGIT-BINDING AGENTS

(71) Applicant: MEREO BIOPHARMA 5, INC., Redwood City, CA (US)

(72) Inventors: Jakob Dupont, Hillsborough, CA (US); Hema Parmar, San Mateo, CA (US)

(73) Assignee: MEREO BIOPHARMA 5, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/119,883

(22) Filed: Dec. 11, 2020

(65) Prior Publication Data

US 2021/0101971 A1    Apr. 8, 2021

Related U.S. Application Data

(63) Continuation of application No. 16/464,820, filed as application No. PCT/US2017/063918 on Nov. 30, 2017.

(60) Provisional application No. 62/479,609, filed on Mar. 31, 2017, provisional application No. 62/427,903, filed on Nov. 30, 2016.

(51) Int. Cl.
| | |
|---|---|
| *A61K 39/00* | (2006.01) |
| *C07K 16/24* | (2006.01) |
| *A61P 35/00* | (2006.01) |
| *C07K 5/10* | (2006.01) |
| *C07K 5/12* | (2006.01) |
| *C07K 14/47* | (2006.01) |
| *C07K 16/28* | (2006.01) |

(52) U.S. Cl.
CPC .............. *C07K 16/24* (2013.01); *A61P 35/00* (2018.01); *C07K 5/10* (2013.01); *C07K 5/12* (2013.01); *C07K 14/47* (2013.01); *C07K 16/2803* (2013.01); *C07K 16/2818* (2013.01); *C07K 16/2827* (2013.01); *A61K 2039/505* (2013.01); *A61K 2039/545* (2013.01); *A61K 2039/55* (2013.01); *C07K 2317/76* (2013.01); *Y02A 50/30* (2018.01)

(58) Field of Classification Search
CPC ................................................ A61K 2039/505
See application file for complete search history.

(56) References Cited

U.S. PATENT DOCUMENTS

| | | |
|---|---|---|
| 7,193,069 B2 | 3/2007 | Isogai et al. |
| 7,282,570 B2 | 10/2007 | Goddard et al. |
| 7,943,743 B2 | 5/2011 | Korman et al. |
| 8,431,350 B2 | 4/2013 | Baldwin et al. |
| 8,728,474 B2 | 5/2014 | Honjo et al. |
| 8,758,753 B2 | 6/2014 | Mateo De Acosta Del Rio et al. |
| 9,499,596 B2 | 11/2016 | Clark et al. |
| 9,695,238 B2 | 7/2017 | Gao et al. |
| 9,713,641 B2 | 7/2017 | Hicklin et al. |
| RE46,534 E | 9/2017 | Baldwin et al. |
| 9,856,318 B2 | 1/2018 | Eisenbach-Schwartz et al. |
| 9,873,740 B2 | 1/2018 | Grogan et al. |
| RE46,805 E | 4/2018 | Baldwin et al. |
| RE46,816 E | 5/2018 | Baldwin et al. |
| 9,994,637 B2 | 6/2018 | Gao et al. |
| 10,017,572 B2 | 7/2018 | Grogan et al. |
| 10,047,158 B2 | 8/2018 | Grogan et al. |
| 10,112,997 B2 | 10/2018 | Gurney et al. |
| 10,189,902 B2 | 1/2019 | Maurer et al. |
| 10,537,633 B2 | 1/2020 | Tso et al. |
| 10,544,219 B2 | 1/2020 | Gurney et al. |
| 10,611,836 B2 | 4/2020 | Grogan et al. |
| 10,626,174 B2 | 4/2020 | Grogan et al. |
| 10,766,957 B2 | 9/2020 | Williams et al. |
| 11,008,390 B2 | 5/2021 | Maurer et al. |
| 2004/0121370 A1 | 6/2004 | Baldwin et al. |
| 2004/0185040 A1 | 9/2004 | Garcia-Martinez et al. |
| 2004/0258678 A1 | 12/2004 | Bodary et al. |
| 2006/0001053 A1 | 5/2006 | Isogai et al. |
| 2007/0041985 A1 | 2/2007 | Unger et al. |
| 2007/0054360 A1 | 3/2007 | Gao et al. |
| 2007/0072797 A1 | 3/2007 | Robinson et al. |
| 2008/0038264 A1 | 2/2008 | Bodary et al. |
| 2008/0050809 A1 | 2/2008 | Abuin et al. |
| 2008/0064049 A1 | 3/2008 | Clarke et al. |
| 2008/0178305 A1 | 7/2008 | Clarke et al. |
| 2009/0025801 A1 | 1/2009 | Stehr et al. |
| 2009/0142346 A1 | 6/2009 | Sato et al. |

(Continued)

FOREIGN PATENT DOCUMENTS

| | | |
|---|---|---|
| CN | 103073644 A | 5/2013 |
| EP | 2067791 | 6/2009 |

(Continued)

OTHER PUBLICATIONS

Harjunpää et al. (Clin. Exp. Immunol. May 2020; 200 (2): 108-19).*
Ingram et al. (Proc. Natl. Acad. Sci. USA. Apr. 10, 2018; 115 (15): 3912-3917).*
Kipps et al. (J. Exp. Med. Jan. 1, 1985; 161 (1): 1-17).*
Perez-Santos et al. (Expert Opinion on Therapeutic Patents. 2020; 30 (2): 83-6).*

(Continued)

*Primary Examiner* — Stephen L Rawlings

(74) *Attorney, Agent, or Firm* — Wolff IP a Prof Corp; Jessica Wolff

(57) ABSTRACT

Methods for enhancing the immune response and/or treatment of diseases such as cancer comprising an agent that specifically binds TIGIT are disclosed. The TIGIT-binding agents may include polypeptides, antibodies, and/or bispecific agents.

30 Claims, 2 Drawing Sheets

Specification includes a Sequence Listing.

(56) References Cited

U.S. PATENT DOCUMENTS

| | | |
|---|---|---|
| 2009/0258013 A1 | 10/2009 | Clark et al. |
| 2010/0316646 A1 | 12/2010 | Gao et al. |
| 2012/0128687 A1 | 5/2012 | Adler et al. |
| 2012/0213774 A1 | 8/2012 | Fertig et al. |
| 2013/0251720 A1 | 9/2013 | Clark et al. |
| 2014/0186380 A1 | 7/2014 | Gurney et al. |
| 2014/0271664 A1 | 9/2014 | Garcia-Martinez et al. |
| 2014/0341902 A1 | 11/2014 | Maecker et al. |
| 2015/0152160 A1 | 6/2015 | Gao et al. |
| 2015/0216970 A1 | 8/2015 | Grogan et al. |
| 2015/0322119 A1 | 11/2015 | Engelhardt et al. |
| 2016/0000909 A1 | 1/2016 | Eisenbach-Schwartz et al. |
| 2016/0008463 A1 | 1/2016 | Eisenbach-Schwartz et al. |
| 2016/0152720 A1 | 6/2016 | Kim et al. |
| 2016/0176963 A1 | 6/2016 | Maurer et al. |
| 2016/0185863 A1 | 6/2016 | Gao et al. |
| 2016/0355589 A1 | 12/2016 | Williams et al. |
| 2016/0376365 A1 | 12/2016 | Gurney et al. |
| 2017/0037133 A1 | 2/2017 | Fiedler et al. |
| 2017/0088613 A1 | 3/2017 | Grogan et al. |
| 2017/0107300 A1 | 4/2017 | Kuchroo et al. |
| 2017/0198042 A1 | 7/2017 | Williams et al. |
| 2017/0209574 A1 | 7/2017 | Cao |
| 2017/0260594 A1 | 9/2017 | Molinero et al. |
| 2017/0281764 A1 | 10/2017 | Tso et al. |
| 2017/0340733 A1 | 11/2017 | Cao |
| 2018/0355040 A1 | 12/2018 | Chand et al. |
| 2019/0010246 A1* | 1/2019 | Liang ............... C07K 16/3061 |
| 2019/0077864 A1 | 3/2019 | Gurney et al. |
| 2019/0365861 A1* | 12/2019 | Bernett ............. A61K 39/3955 |
| 2020/0024351 A1* | 1/2020 | Reeves ............. C07K 16/2818 |
| 2020/0181274 A1* | 6/2020 | Saville ............. C07K 16/2827 |

FOREIGN PATENT DOCUMENTS

| | | | | |
|---|---|---|---|---|
| EP | | 1539228 | 12/2010 | |
| EP | | 1891107 | 7/2011 | |
| EP | | 2399932 | 11/2016 | |
| EP | | 2279412 | 7/2017 | |
| EP | | 3208612 | 9/2019 | |
| EP | | 3214095 | 12/2019 | |
| EP | | 3021869 | 7/2020 | |
| EP | | 3331915 | 2/2021 | |
| WO | | 2003/068943 | 8/2003 | |
| WO | | 2004/024068 | 3/2004 | |
| WO | | 2006/121168 | 11/2006 | |
| WO | WO 2006/124667 A2 | | 11/2006 | |
| WO | WO 2008/042236 A2 | | 4/2008 | |
| WO | | 2009/009523 | 1/2009 | |
| WO | | 2009/126688 | 10/2009 | |
| WO | | 2010/077634 | 7/2010 | |
| WO | | 2011/066342 | 6/2011 | |
| WO | WO 2011/100566 A2 | | 8/2011 | |
| WO | | 2011/109789 | 9/2011 | |
| WO | WO 2014/089113 A1 | | 6/2014 | |
| WO | WO 2014/089169 A2 | | 6/2014 | |
| WO | | 2014/179664 | 11/2014 | |
| WO | WO 2015/009856 A2 | | 1/2015 | |
| WO | | 2015/048312 | 4/2015 | |
| WO | | 2015/117002 | 8/2015 | |
| WO | WO 2015/143343 A2 | | 9/2015 | |
| WO | WO 2016/011264 A2 | | 1/2016 | |
| WO | WO 2016/028656 A1 | | 2/2016 | |
| WO | WO 2016/040892 A1 | | 3/2016 | |
| WO | WO 2016/054555 A2 | | 4/2016 | |
| WO | WO 2016/100882 A1 | | 6/2016 | |
| WO | WO 2016/106302 A1 | | 6/2016 | |
| WO | WO 2016/109546 A2 | | 7/2016 | |
| WO | WO 2016/191643 A2 | | 12/2016 | |
| WO | | 2017/021526 | 2/2017 | |
| WO | WO 2017/030823 A2 | | 2/2017 | |
| WO | | 2017/053748 | 3/2017 | |
| WO | WO 2017/037707 A1 | | 3/2017 | |
| WO | WO 2017/048824 A1 | | 3/2017 | |
| WO | | 2017/059095 | 6/2017 | |
| WO | | 2017/152088 | 9/2017 | |
| WO | WO 2018/102536 A1 | | 6/2018 | |
| WO | WO-2018102536 A1 * | | 6/2018 | ......... C07K 16/2803 |
| WO | | 2018/160704 | 9/2018 | |
| WO | | 2019/023504 | 1/2019 | |

OTHER PUBLICATIONS

Park et al. (Cancer Res. Jul. 1, 2017; 77 (13 Suppl.): 2003; pp. 1-4).*
Brodská et al. (Cancer Immunol. Res. Oct. 2016; 4 (10): 815-819).*
Blümich et al. (PNAS. 2018; 115 (15): 3912-7).*
Clinical Trial NCT03119428 (A Study of OMP-313M32 in Subjects With Locally Advanced or Metastatic Solid Tumors); Posted Apr. 18, 2017; pp. 1-8).*
Joller, N., et al., "Treg cells expressing the coinhibitory molecule TIGIT selectively inhibit proinflammatory Th1 and Th17 cell responses," *Immunity* 40(4):569-581, Elsevier Inc., United States (2014).
UniProtKB, "TIGIT_Mouse," Accession No. P86176, accessed at http://www.uniprot.org/uniprot/P86176, accessed on Sep. 5, 2016, 8 pages.
Uniprotkb, "TIGIT_Human," Accession No. Q495A1, accessed at http://www.uniprot.org/uniprot/Q495A1, accessed on Sep. 5, 2016, 12 pages.
Chan, C.J., et al., "Receptors that interact with nectin and nectin-like proteins in the immunosurveillance and immunotherapy of cancer," *Current Opinion in Immunology* 24(2):246-251, Elsevier Ltd., England (2012).
Chauvin, J-M., et al., "TIGIT and PD-1 impair tumor antigen-specific CD8$^+$ T cells in melanoma patients," *The Journal of Clinical Investigation* 125(5):2046-2058, American Society for Clinical Investigation, United States (2015).
Johnston, R.J., et al., "The Immunoreceptor TIGIT Regulates Antitumor and Antiviral CD8$^+$ T cell Effector Function," *Cancer Cell* 26(6):923-937, Elsevier Inc., United States (2014).
Johnston, R.J., et al., "The Immunoreceptor TIGIT Regulates Antitumor and Antiviral CD8$^+$ T cell Effector Function," *Cancer Cell* 26:S1-S20, Supplemental Data, Elsevier Inc., United States (2014).
Joller, N., et al., "Cutting Edge: TIGIT Has T Cell-Intrinsic Inhibitory Functions," *The Journal of Immunology* 186(3):1338-1342, The American Association of Immunologists, Inc., United States (2011).
Joller, N., et al., "Cutting Edge: TIGIT Has T Cell-Intrinsic Inhibitory Functions," *The Journal of Immunology* 186(3):1338-1342, Supplementary Figures 1-4 and Supplementary Tables 1-2, The American Association of Immunologists, Inc., United States (2011).
Lozano, E., et al., "The TIGIT/CD226 Axis Regulates Human T Cell Function," *The Journal of Immunology* 188(8):3869-3875, The American Association of Immunologists, Inc., United States (2012).
Stanietsky, N., et al., "Mouse TIGIT inhibits NK-cell cytotoxicity upon interaction with PVR," *European Journal of Immunology* 43(8):2138-2150, Weinheim Wiley-VCH, Germany (2013).
Yu, X., et al., "The surface protein TIGIT suppresses T cell activation by promoting the generation of mature immunoregulatory dendritic cells," *Nature Immunology* 10(1):48-57, Nature Publishing Group, England (2009).
Yu, X., et al., "The surface protein TIGIT suppresses T cell activation by promoting the generation of mature immunoregulatory dendritic cells," *Nature Immunology* 10(1):48-57, Supplementary Figures 1-7 and Supplementary Tables 1-3, Nature Publishing Group, England (2009).
Stanietsky, N., et al., "The interaction of TIGIT with PVR and PVRL2 inhibits human NK cell cytotoxicity," *Proc Natl Acad Sci USA* 106(42):17858-17863, National Academy of Sciences, United States (2009).
International Search Report and Written Opinion for International Application No. PCT/US2017/063918, ISA/US, Alexandria, Virginia, dated Mar. 7, 2018, 10 pages.
Stengel, K.F., et al., "Structure of TIGIT immunoreceptor bound to poliovirus receptor reveals a cell-cell adhesion and signaling mechanism that requires *cis-trans* receptor clustering," *Proceedings of the National Academy of Sciences* 109(14):5399-5404, National Academy of Sciences, United States (2012).

(56) References Cited

OTHER PUBLICATIONS

International Preliminary Report on Patentability and Written Opinion for International Application No. PCT/US2017/063918, The International Bureau of WIPO, dated Jun. 4, 2019, 7 pages.
Pauken, K.E., et al., "TIGIT and CD226: Tipping the Balance between Costimulatoty and Coinhibitory Molecules to Augment the Cancer Immunotherapy Toolkit," Cancer Cell 26(6):785-787, Cell Press, United States (2014).
English translation of CN 103073644 A, published on May 1, 2013, University of Science and Technology of China, document FP23.
Meibohm et al., "Pharmacokinetics and Pharmacodynamics of Biotech Drugs", Encyclopedia of Molecular Cell Biology and Molecular Medicine, 2nd Edition. vol. 10, Edited by Robert A. Meyers, Copyright 2005, Wiley-VCH Verlag GmbH & Co. KGaA, Weinheim, pp. 211-239.
White et al., "Antibody-Targeted Immunotherapy for Treatment ofMalignancy", Annu. Rev. Med., 2001, 52:125-45.
Blackburn, et al., "Coregulation of CD8+ T cell exhaustion by multiple inhibitory receptors during chronic viral infection", at Immunol. Jan. 2009;10(1):29-37. doi: 10.1038/ni.1679. Epub Nov. 30, 2008.
Callahan, et al., "At the bedside: CTLA-4- and PD-1-blocking antibodies in cancer immunotherapy", Leukoc Biol. Jul. 2013;94(1):41-53. doi: 10.1189/jlb.1212631. Epub May 10, 2013.
Chen et al., "Molecular pathways: next-generation immunotherapy-inhibiting programmed death-ligand 1 and programmed death-1", Clin Cancer Res. Dec. 15, 2012;18(24):6580-7. doi: 10.1158/1078-0432.CCR-12-1362. Epub Oct. 19, 2012.
Comps-Agrar et al.,"TIGIT mediated T cell exhaustion in cancer is dependent on TIGIT/CD226 interaction (TUM2P.907)", the Journal of Immunology, vol. 192, No. S1, May 1, 2014 (May 1, 2014).
Curran et al., "PD-1 and CTLA-4 combination blockade expands infiltrating T cells and reduces regulatory T and myeloid cells within B16 melanoma tumors", Proc Natl Acad Sci U S A. Mar. 2, 2010;107(9):4275-80. doi: 10.1073/pnas.0915174107. Epub Feb. 16, 2010.
Duraiswamy et al., "Dual blockade of PD-1 and CTLA-4 combined with tumor vaccine effectively restores T-cell rejection function in tumors", Cancer Res. Jun. 15, 2013;73(12):3591-603. doi: 10.1158/0008-5472.CAN-12-4100. Epub Apr. 30, 2013.
Grogan et al."TIGIT inhibits CD8+ T cell effector function during chronic viral infection and cancer (TUM7P.933)", the Journal of Immunology, vol. 192, No. S1, May 1, 2014 (May 1, 2014).
Hamid et al., "Anti-programmed death-1 and anti-programmed death-ligand 1 antibodies in cancer therapy", Expert Opin Biol Ther. Jun. 2013;13(6):847-61. doi: 10.1517/14712598.2013.770836 Epub Feb. 19, 2013.
Hutloff, A., "T-cell costimulation. Basic mechanisms and new aspects", Z Rheumatol. Sep. 2011;70(7):588-91. doi: 10.1007/s00393-011-0862-y.
Jin et al., "Cooperation of Tim-3 and PD-1 in CD8 T-cell exhaustion during chronic viral infection", Proc Natl Acad Sci U S A Aug. 17, 2010;107(33):14733-8. doi: 10.1073/pnas.1009731107. Epub Aug. 2, 2010.
Joller et al., "Immune checkpoints in central nervous system autoimmunity", mmunol Rev. Jul. 2012;248(1):122-39. doi: 10.1111/j.1600-065X.2012.01136.x.
Levin et al., "Vstm3 is a member of the CD28 family and an important modulator of T-cell function", Eur J Immunol. Apr. 2011;41(4):902-15. doi: 10.1002/eji.201041136. Epub Mar. 18, 2011.
Inozume et al."Development of a novel immunotherapy for melanoma which inhibits interaction between CD155 on melanoma cells and TIGIT on activated CTL", Abstracts of the 2013 International Investigative Dermatology Meeting. May 8-11, 2013. Edinburgh, Scotland, United Kingdom, J Invest Dermatol. May 2013;133 Suppl 1:S1-311.
Inozume et al., "CD155 is highly expressed by melanoma tissues and it suppresses the activation of melanoma specific CTLs via interaction with TIGIT", Journal of Dermatological Science, vol. 69, Issue 2, E67-E68, Feb. 1, 2013.
Intlekofer et al., "At the bench: preclinical rationale for CTLA-4 and PD-1 blockade as cancer immunotherapy", J Leukoc Biol. Jul. 2013;94(1):25-39. doi: 10.1189/jlb.1212621. Epub Apr. 26, 2013.
Malyguine et al., "Malyguine ELISPOT Assay for Monitoring Cytotoxic T Lymphocytes (CTL) Activity in Cancer Vaccine Clinical Trials. Cells. 2012;1 (2):111-126. Published May 10, 2012. doi:10.3390/cells1020111", Cells. May 10, 2012;1(2):111-26. doi: 10.3390/cells1020111.
Matsuzaki et al., "Tumor-infiltrating NY-ESO-1-specific CD8+ T cells are negatively regulated by LAG-3 and PD-1 in human ovarian cancer", Proc Natl Acad Sci U S A. Apr. 27, 2010;107(17):7875-80. doi: 10.1073/pnas.1003345107. Epub Apr. 12, 2010.
McDermott and Atkins, "PD-1 as a potential target in cancer therapy", Cancer Med. Oct. 2013;2(5):662-73. doi: 10.1002/cam4.106. Epub Jul. 21, 2013.
Mullard, A., "New checkpoint inhibitors ride the immunotherapy tsunami", at Rev Drug Discov. Jul. 2013;12(7):489-92. doi: 10.1038/nrd4066.
Nakamoto et al., "Synergistic reversal of intrahepatic HCV-specific CD8 T cell exhaustion by combined PD-1/CTLA-4 blockade", PLoS Pathog. Feb. 2009;5(2):e1000313. doi: 10.1371/journal.ppat.1000313. Epub Feb. 27, 2009.
Quezada and Peggs, "Exploiting CTLA-4, PD-1 and PD-L1 to reactivate the host immune response against cancer", Br J Cancer. Apr. 30, 2013;108(8):1560-5. doi: 10.1038/bjc.2013.117. Epub Mar. 19, 2013.
Yu et al., "Simultaneous inhibition of two regulatory T-cell subsets enhanced Interleukin-15 efficacy in a prostate tumor model", Proc Natl Acad Sci U S A. Apr. 17, 2012;109(16):6187-92. doi: 10.1073/pnas.1203479109. Epub Apr. 2, 2012.
Zhou et al., "Coexpression of Tim-3 and PD-1 identifies a CD8+ T-cell exhaustion phenotype in mice with disseminated acute myelogenous leukemia", Blood. Apr. 28, 2011;117(17):4501-10. doi: 10.1182/blood-2010-10-310425. Epub Mar. 8, 2011.
Chew et al., "TIGIT Marks Exhausted T Cells, Correlates with Disease Progression, and Serves as a Target for Immune Restoration in HIV and SIV Infection", PLoS Pathog. Jan. 7, 2016;12(1):e1005349. doi: 10.1371/journal.ppat.1005349. eCollection Jan. 2016.
Foks et al., "Agonistic anti-TIGIT treatment inhibits T cell responses in LDLr deficient mice without affecting atherosclerotic lesion development", PLoS One. Dec. 20, 2013;8(12):e83134. doi: 10.1371/journal.pone.0083134. eCollection 2013.
Friedrich et al., "Preclinical characterization of AMG 330, a CD3/CD33-bispecific T-cell-engaging antibody with potential for treatment of acute myelogenous leukemia", Mol Cancer Ther. Jun. 2014;13(6):1549-57. doi: 10.1158/1535-7163.MCT-13-0956. Epub Mar. 27, 2014.
Hou et al., "Recombinant soluble CD226 protein directly inhibits cancer cell proliferation in vitro", Int Immunopharmacol. Mar. 2014;19(1):119-26. doi: 10.1016/j.intimp.2014.01.012 Epub Jan. 27, 2014.
Inozume et al., "Melanoma Cells Control Antimelanoma CTL Responses via Interaction between TIGIT and CD155 in the Effector Phase", J Invest Dermatol. Jan. 2016;136(1):255-63. doi: 10.1038/JID.2015.404.
Kong et al., "T-Cell Immunoglobulin and ITIM Domain (TIGIT) Associates with CD8+ T-Cell Exhaustion and Poor Clinical Outcome in AML Patients", Clin Cancer Res. Jun. 15, 2016;22(12):3057-66. doi: 10.1158/1078-0432.CCR-15-2626. Epub Jan. 13, 2016.
Krupka et al., "Blockade of the PD-1/PD-L1 axis augments lysis of AML cells by the CD33/CD3 BiTE antibody construct AMG 330: reversing a T-cell-induced immune escape mechanism", Leukemia. Feb. 2016;30(2):484-91. doi: 10.1038/leu.2015.214. Epub Aug. 4, 2015.
Mellman, Ira, "Developments in Cancer Immunotherapy", Nov. 2017 (20 pages).
Mun et al., "Air sparging for prevention of antibody disulfide bond reduction in harvested CHO cell culture fluid", Biotechnol Bioeng. Apr. 2015;112(4):734-42. doi: 10.1002/bit.25495. Epub Dec. 23, 2014.

(56) References Cited

OTHER PUBLICATIONS

Robert et al., "Anti-programmed-death-receptor-1 treatment with pembrolizumab in ipilimumab-refractory advanced melanoma: a randomised dose-comparison cohort of a phase 1 trial", Lancet. Sep. 20, 2014;384(9948):1109-17. doi: 10.1016/S0140-6736(14)60958-2. Epub Jul. 15, 2014.

Zheng and Zhou, "Human Cancer Immunotherapy with PD-1/PD-L1 Blockade", Biomark Cancer. Sep. 20, 2015;7(Suppl 2):15-8. doi: 10 4137/BIC.S29325. eCollection 2015.

FDA News Release (2016) regarding approval of anti-PD-L 1 antibody for treatment of bladder cancer (3 pages).

Zhan et al., "From monoclonal antibodies to small molecules: the development of inhibitors targeting the PD-1/PD-L1 pathway", Drug Discov Today. . Jun. 2016;21(6):1027-36. doi: 10.1016/j.drudis.2016.04.011. Epub Apr. 16, 2016.

Inozume et al., Poster presented at the Journal of Investigative Dermatology & International Investigative Dermatology Meeting, Edinburgh UK, May 8-11, 2013.

Selby et al., "Antitumor activity of concurrent blockade of immune checkpoint molecules CTLA-4 and PD-1 in preclinical models", PLoS One. Sep. 9, 2016;11(9):e0161779. doi: 10.1371/journal.pone.0161779. eCollection 2016.

Wolchok et al., "Nivolumab plus ipilimumab in advanced melanoma", N Engl J Med. Jul. 11, 2013;369(2):122-33. doi: 10.1056/NEJMoa1302369. Epub Jun. 2, 2013.

Mahnke and Enk, "TIGIT-CD155 Interactions in Melanoma: A Novel Co-Inhibitory Pathway with Potential for Clinical Intervention", J Invest Dermatol. Jan. 2016;136(1):9-11. doi: 10.1016/j.jid.2015.10.048.

NCT02794571, "A Phase Ia/Ib Open-Label, Dose-Escalation Study of the Safety and Pharmacokinetics of Tiragolumab as a Single Agent and in Combination With Atezolizumab and/or Other Anti-Cancer Therapies in Patients With Locally Advanced or Metastatic Tumors", 2016, retrieved from https://clinicaltrials.gov/ct2/show/NCT02794571?term=NCT02794571&draw=2&rank=1 on Jun. 28, 2021 (22 pages).

NCT02913313, "Phase 1/2a First-In-Human Study of BMS-986207 Monoclonal Antibody Alone and in Combination With Nivolumab or With Nivolumab and Ipilimumab in Advanced Solid Tumors", 2016, retrieved from https://clinicaltrials.gov/ct2/show/NCT02913313?term=NCT02913313&draw=2&rank=1 (10 pages).

Agrawal et al., "Nivolumab dose selection: challenges, opportunities, and lessons learned for cancer immunotherapy", J Immunother Cancer Nov. 15, 2016;4:72. doi: 10.1186/s40425-016-0177-2. eCollection 2016.

John et al., "Blockade of PD-1 immunosuppression boosts CAR T-cell therapy", Oncoimmunology. Oct. 1, 2013;2(10):e26286. doi: 10.4161/onci.26286. Epub Oct. 10, 2013.

Magee et al., "GUCY2C-targeted chimeric antigen receptor expressing T cells extend survival in a therapeutic mouse model of metastatic colorectal cancer", Journal for ImmunoTherapy of Cancer 2013, 1(Suppl 1):P22 http://www.immunotherapyofcancer.org/content/1/S1/P22.

Stamm et al., "Immune checkpoints PVR and PVRL2 are prognostic markers in AML and their blockade represents a new therapeutic option", Oncogene. Sep. 2018;37(39):5269-5280. doi: 10.1038/s41388-018-0288-y. Epub May 31, 2018.

\* cited by examiner

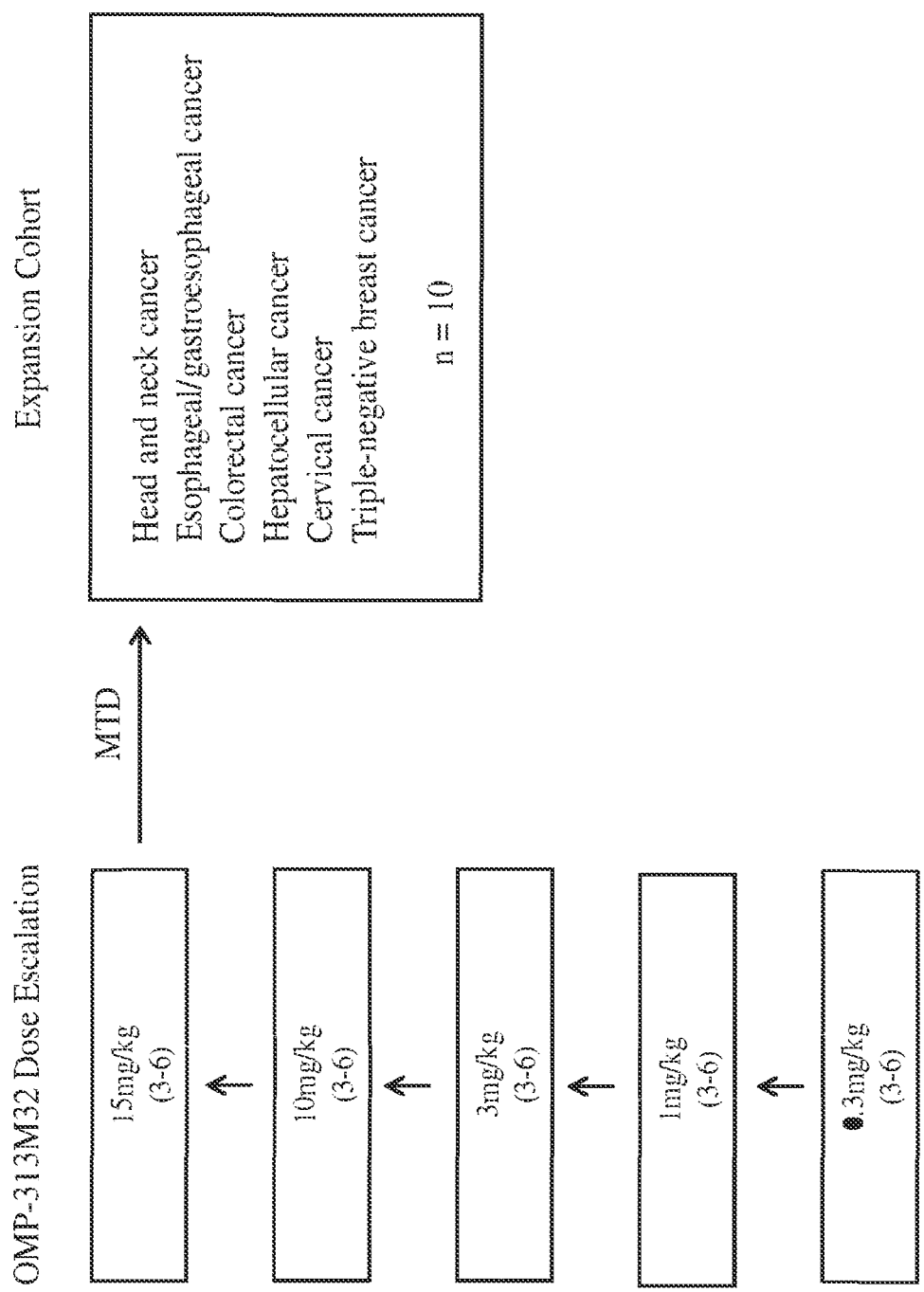

US 11,136,384 B2

METHODS FOR TREATMENT OF CANCER COMPRISING TIGIT-BINDING AGENTS

CROSS-REFERENCE TO RELATED APPLICATIONS

The present invention is a continuation of U.S. patent application Ser. No. 16/464,820, filed May 29, 2019, which is the U.S. National Phase of International Patent Application No. PCT/US2017/063918, filed Nov. 30, 2017, which claims the benefit of priority to U.S. Provisional Application No. 62/479,609, filed Mar. 31, 2017, and to U.S. Provisional Application No. 62/427,903, filed Nov. 30, 2016, each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 11, 2020, is named OMP-164US-CON1_SeqListing.txt and is 48 kilobytes in size.

FIELD OF THE INVENTION

The present invention generally relates to methods for treating cancer using agents that bind human TIGIT, particularly antibodies that specifically bind the extracellular domain of TIGIT.

BACKGROUND OF THE INVENTION

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include agents and methods to induce or enhance specific immune responses or to inhibit or reduce specific immune responses.

The immune system is a highly complex system made up of a great number of cell types, including but not limited to, T-cells, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases).

The concept of cancer immunosurveillance is based on the theory that the immune system can recognize tumor cells, mount an immune response, and suppress the development and/or progression of a tumor. However, it is clear that many cancer/tumor cells have developed mechanisms to evade the immune system which can allow for uninhibited growth of those cells. Cancer/tumor immunotherapy focuses on the development of new and novel agents that can activate and/or boost the immune system to achieve a more effective attack against tumor cells resulting in increased killing of tumor cells and/or inhibition of tumor growth.

BRIEF SUMMARY OF THE INVENTION

The present invention provides methods for treatment of cancer (i.e., inhibiting tumor growth) using agents that bind T-cell immunoreceptor with Ig and ITIM domains (TIGIT), including, but not limited to, antibodies that specifically bind the extracellular domain of TIGIT. In certain embodiments, the agent is a TIGIT antagonist. In some embodiments, a method comprises using a TIGIT-binding agent to induce, activate, promote, increase, enhance, or prolong an immune response to cancer and/or a tumor. In some embodiments, a method comprises using a TIGIT-binding agent to inhibit tumor growth. In some embodiments, a method comprises using a TIGIT-binding agent for the treatment of cancer. In some embodiments, a method comprises using a TIGIT-binding agent in combination with at least one additional therapeutic agent.

In some embodiments of the invention, a method of inhibiting tumor growth in a subject comprises administering to the subject a therapeutically effective amount of a TIGIT-binding agent, wherein the tumor is a colorectal cancer (CRC) such as a microsatellite instability-high colorectal cancer (MSI CRC) or a microsatellite stable colorectal cancer (MSS CRC), a triple negative breast cancer (TNBC), a Merkel cell carcinoma, an endometrial cancer, or an esophageal cancer. In some embodiments, a method of inhibiting tumor growth in a subject comprises administering to the subject a therapeutically effective amount of an antibody that specifically binds the extracellular domain of human TIGIT, wherein the tumor is a microsatellite instability-high colorectal cancer, a microsatellite stable colorectal cancer, a triple negative breast cancer, a Merkel cell carcinoma, an endometrial cancer, or an esophageal cancer, and wherein the antibody that binds human TIGIT comprises a heavy chain CDR1 comprising TSDYAWN (SEQ ID NO:4), a heavy chain CDR2 comprising YISYSGSTSYN-PSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the invention, a method of inhibiting tumor growth in a subject comprises administering to the subject a therapeutically effective amount of a TIGIT-binding agent, wherein the tumor is a solid tumor with high microsatellite instability (MSI). In some embodiments, a method of inhibiting tumor growth in a subject comprises administering to the subject a therapeutically effective amount of an antibody that specifically binds the extracellular domain of human TIGIT, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments the solid tumor with high MSI is selected from the group consisting of a MSI CRC, a MSI gastric cancer, a MSI endometrium cancer, a MSI ovarian cancer, a MSI hepatobiliary tract cancer, a MSI urinary tract cancer, a MSI brain cancer, or a MSI skin cancer.

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the tumor is a microsatellite instability-high colorectal cancer, a microsatellite stable colorectal cancer, a triple negative breast cancer, a Merkel cell carcinoma, an endometrial cancer, or an esophageal cancer. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the tumor is a colorectal cancer (CRC) such as a microsatellite instability-high colorectal cancer or a microsatellite stable colorectal cancer, a triple negative breast cancer, a Merkel cell carcinoma, an endometrial cancer, or an esophageal cancer, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the combination therapy comprises an anti-PD-1 antibody. In some embodiments, the combination therapy comprises an anti-PD-L1 antibody.

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the tumor is a solid tumor with high MSI. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the tumor is a solid tumor with a high microsatellite instability, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the combination therapy comprises an anti-PD-1 antibody. In some embodiments, the combination therapy comprises an anti-PD-L1 antibody. In some embodiments the solid tumor with high MSI is selected from the group consisting of a MSI CRC, a MSI gastric cancer, a MSI endometrium cancer, a MSI ovarian cancer, a MSI hepatobiliary tract cancer, a MSI urinary tract cancer, a MSI brain cancer or a MSI skin cancer.

In some embodiments of the invention, a method of inhibiting tumor growth in a subject comprises administering to the subject a therapeutically effective amount of a TIGIT-binding agent, wherein the tumor is resistant or refractory to treatment with a PD-1 antagonist or a PD-L1 antagonist. In some embodiments, a method of inhibiting tumor growth in a subject comprises administering to the subject a therapeutically effective amount of an antibody that specifically binds the extracellular domain of human TIGIT, wherein the tumor is resistant or refractory to treatment with a PD-1 antagonist or a PD-L1 antagonist; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor was resistant or refractory to treatment with a PD-1 antagonist or a PD-L1 antagonist. As used herein, a tumor is resistant or refractory to treatment with an agent wherein there is tumor growth progression during or after treatment with the agent. In some embodiments, a tumor is resistant or refractory to treatment with an agent that is administered as a single agent. In some embodiments, a tumor is resistant or refractory to treatment with an agent that is administered as a first-line treatment or a second-line treatment. In some embodiments, the tumor is resistant or refractory to treatment with an anti-PD-1 antibody (e.g., as a single agent). In some embodiments, the tumor is resistant or refractory to treatment with an anti-PD-L1 antibody (e.g., as a single agent). In some embodiments, the tumor resistant or refractory to treatment with a PD-1 antagonist or a PD-L1 antagonists is selected from the group consisting of melanoma, non-small cell lung cancer (NSCLC), renal cell carcinoma, squamous cell carcinoma of the head and neck, urothelial carcinoma, colorectal cancer (e.g. MSI or DNA mismatch repair defective (dMMR) metastatic CRC) and hepatocellular carcinoma.

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the tumor is resistant or refractory to treatment with a PD-1 antagonist or a PD-L1 antagonist as a single agent. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the tumor is resistant or refractory to treatment with a PD-1 antagonist or a PD-L1 antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a tumor is resistant or refractory to treatment with an agent that is administered as a first-line treatment or a second-line treatment. In some embodiments, a tumor is resistant or refractory to treatment with a PD-1 antagonist as a single agent, but is responsive to treatment with this agent in combination with a TIGIT-binding agent. In some embodiments, a tumor is resistant or refractory to treatment with a PD-L1 antagonist as a single agent, but is responsive to treatment with this agent in combination with a TIGIT-binding agent. In some embodiments, the tumor is resistant or refractory to treatment with an anti-PD-1 antibody (e.g., as a single agent). In some embodiments, the tumor is resistant or refractory to treatment with an anti-PD-L1 antibody (e.g., as a single agent). In some embodiments, the combination therapy comprises an anti-PD-1 antibody. In some embodiments, the combination therapy comprises an anti-PD-L1 antibody. In some embodiments, the tumor resistant or refractory to treatment with a PD-1 antagonist or a PD-L1 antagonists is selected from the group consisting of melanoma, NSCLC, renal cell carcinoma, squamous cell carcinoma of the head and neck, urothelial carcinoma, colorectal cancer MSI or dMMR metastatic CRC) and hepatocellular carcinoma.

In some embodiments of the invention, a method of inhibiting tumor growth in a subject comprises administering to the subject a therapeutically effective amount of a TIGIT-binding agent, wherein the subject has previously been treated with a PD-1 antagonist or a PD-L1 antagonist as a single agent. In some embodiments, a method of inhibiting tumor growth in a subject comprises administering to the subject a therapeutically effective amount of an antibody that specifically binds the extracellular domain of human TIGIT, wherein the subject has previously been treated with a PD-1 antagonist or a PD-LL antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with a PD-1 antagonist or a PD-L1 antagonist, wherein there was disease progression on or after treatment. In some embodiments, there is tumor growth recurrence after treatment with a PD-1 antagonist or a PD-L1 antagonist. As used herein, tumor growth recurrence is defined as the return of cancer after treatment and after a period of time during which the cancer was not detected. The cancer may come back where it was first found or it may be found somewhere else in the body. In some embodiments, the recurrence is local recurrence, regional recurrence, or distant recurrence. In some embodiments, the subject has previously been treated with an anti-PD-1 antibody. In some embodiments, the subject has previously been treated with an anti-PD-L1 antibody. In some embodiments, the tumor is selected from the group consisting of melanoma, NSCLC, renal cell carcinoma, squamous cell carcinoma of the head and neck, urothelial carcinoma, colorectal cancer (e.g. MSI or dMMR metastatic CRC) and hepatocellular carcinoma.

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the subject has previously been treated with a PD-1 antagonist or a PD-L1 antagonist as a single agent. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the subject has previously been treated with a PD-1 antagonist or a PD-L1 antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with a PD-1 antagonist or a PD-L1 antagonist, wherein there was disease progression on or after treatment. In some embodiments, there is tumor growth recurrence after treatment with a PD-1 antagonist or a PD-L1 antagonist. In some embodiments, the recurrence is local recurrence, regional recurrence, or distant recurrence. In some embodiments, the combination therapy "resensitizes" the tumor to treatment with a PD-1 antagonist or a PD-L1 antagonist. In some embodiments, the subject has previously been treated with an anti-PD-1 antibody. In some embodiments, the subject has previously been treated with an anti-PD-L1 antibody. In some embodiments, the combination therapy comprises an anti-PD-1 antibody. In some embodiments, the combination therapy comprises an anti-PD-L1 antibody. In some embodiments, the tumor is selected from the group consisting of melanoma, NSCLC, renal cell carcinoma, squamous cell carcinoma of the head and neck, urothelial carcinoma, colorectal cancer (e.g. MSI or dMMR metastatic CRC) and hepatocellular carcinoma.

In some embodiments of the invention, a method of inhibiting tumor growth in a subject comprises administering to the subject a therapeutically effective amount of a TIGIT-binding agent, wherein the tumor expresses poliovirus receptor (PVR) and/or poliovirus receptor-related 2 (PVRL2). In some embodiments, a method of inhibiting tumor growth in a subject comprises administering to the subject a therapeutically effective amount of an antibody that specifically binds the extracellular domain of human TIGIT, wherein the tumor expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the tumor expresses PVR and/or PVRL2. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the tumor expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is selected from the group consisting of melanoma. NSCLC, renal cell carcinoma, squamous cell carcinoma of the head and neck, urothelial carcinoma, colorectal cancer (e.g. MSI or dMMR) metastatic CRC and hepatocellular carcinoma.

In some embodiments of the invention, a method of inhibiting tumor growth in a subject comprises administering to the subject a therapeutically effective amount of a TIGIT-binding agent, wherein the tumor comprises tumor-infiltrating lymphocytes (TILs). In some embodiments, a method of inhibiting tumor growth in a subject comprises administering to the subject a therapeutically effective amount of an antibody that specifically binds the extracellular domain of human TIGIT, wherein the tumor comprises tumor-infiltrating lymphocytes; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the invention, a method of inhibiting tumor growth in a subject, comprising administering to the subject a therapeutically effective amount of a TIGIT-binding agent in combination with a PD-1 antagonist or a PD-L1 antagonist, wherein the tumor comprises tumor-infiltrating lymphocytes. In some embodiments, a method of inhibiting tumor growth in a subject, comprising administering to the subject a therapeutically effective amount of an antibody that specifically binds the extracellular domain of human TIGIT in combination with a PD-1 antagonist or a PD-L1 antagonist, wherein the tumor comprises tumor-infiltrating lymphocytes; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the invention, a method of inhibiting tumor growth in a subject comprises administering to the subject a therapeutically effective amount of a TIGIT-binding agent, wherein the tumor comprises regulatory T-cells (Tregs). In some embodiments, a method of inhibiting tumor growth in a subject comprises administering to the subject a therapeutically effective amount of an antibody that specifically binds the extracellular domain of human TIGIT, wherein the tumor comprises Tregs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the invention, a method of inhibiting tumor growth in a subject comprises administering to the subject a therapeutically effective amount of a TIGIT-binding agent in combination with a PD-1 antagonist or a PD-L1 antagonist, wherein the tumor comprises Tregs. In some embodiments, a method of inhibiting tumor growth in a subject comprises administering to the subject a therapeutically effective amount of an antibody that specifically binds the extracellular domain of human TIGIT in combination with a PD-1 antagonist or a PD-L1 antagonist, wherein the tumor comprises Tregs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the methods described herein, the tumor is selected from the group consisting of: lung tumor, liver tumor, breast tumor, renal cell carcinoma/kidney tumor, prostate tumor, gastrointestinal/gastric tumor, melanoma, cervical tumor, bladder tumor, glioblastoma, head and neck tumor, pancreatic tumor, ovarian tumor, colorectal tumor, endometrial tumor, anal tumor and esophageal tumor.

In some embodiments, the lung tumor comprises NSCLC, such as NSCLC squamous cell or NSCLC adenocarcinoma.

In some embodiments, the breast tumor comprises triple-negative breast cancer (TNBC).

In some embodiments, the tumor is a solid tumor with high MSI. In some embodiments, the solid tumor with high microsatellite instability is a MSI colorectal cancer (MSI CRC), a MSI gastric cancer, a MSI endometrium cancer, a MSI ovarian cancer, a MSI hepatobiliary tract cancer, a MSI urinary tract cancer, a MSI brain cancer or a MSI skin cancer. In some embodiments, the solid tumor with high MSI is a MSI CRC.

In some embodiments, the tumor is a microsatellite stable (MSS) tumor. In some embodiments, the tumor is a microsatellite stable colorectal cancer (MSS CRC).

In some embodiments, the tumor is selected from the group consisting of a melanoma, a NSCLC, a renal cell carcinoma, a squamous cell carcinoma of the head and neck, a urothelial carcinoma, a colorectal cancer (e.g. MSI or dMMR metastatic CRC) and hepatocellular carcinoma.

In some embodiments of the methods described herein, the agent is an antibody that specifically binds the extracellular domain of human TIGIT, which comprises a heavy chain CDR1 comprising TSDYAWN (SEQ ID NO:4), a heavy chain CDR2 comprising YISYSGSTSYNPSLRS (SEQ ID NO:5), and a heavy chain CDR3 comprising ARRQVGLGFAY (SEQ ID NO:6), and/or a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the methods described herein, the agent is an antibody that specifically binds the extracellular domain of TIGIT, wherein the antibody comprises a heavy chain variable region having at least 90% sequence identity to SEQ ID NO:10 and/or a light chain variable region having at least 90% sequence identity to SEQ ID NO:11. In some embodiments, an antibody comprises a heavy chain variable region having at least 95% sequence identity to SEQ ID NO:10 and/or a light chain variable region having at least 95% sequence identity to SEQ ID NO:11. In some embodiments, an antibody comprises a heavy chain variable region comprising SEQ ID NO:10 and a light chain variable region comprising SEQ ID NO:11.

In some embodiments of the methods described herein, the TIGIT-binding agent is an antibody which is a monoclonal antibody, a humanized antibody, a human antibody, a recombinant antibody, a chimeric antibody, a bispecific antibody, an antibody fragment comprising an antigen-binding site, an IgG antibody, an IgG1 antibody, an IgG2 antibody, or an IgG4 antibody. In some embodiments, the antibody is monovalent. In some embodiments, the antibody is bivalent. In some embodiments, the antibody is monospecific. In some embodiments, the antibody is bispecific.

In some embodiments of the methods described herein, an antibody that specifically binds human TIGIT comprises a heavy chain amino acid sequence of SEQ ID NO:13 and a light chain amino acid sequence of SEQ ID NO:15. In some embodiments, an antibody that specifically binds human TIGIT comprises a heavy chain amino acid sequence of SEQ ID NO:17 and a light chain amino acid sequence of SEQ ID NO:15.

In some embodiments of the methods described herein, an antibody that specifically binds human TIGIT, does not bind mouse TIGIT. In some embodiments an antibody that specifically binds human TIGIT, does not bind rat TIGIT. In some embodiments an antibody that specifically binds human TIGIT, does not bind rabbit TIGIT. In some embodiments an antibody that specifically binds human TIGIT, does not bind marmoset TIGIT. In some embodiments an antibody that specifically binds human TIGIT, does not bind dog TIGIT. In some embodiments an antibody that specifically binds human TIGIT, does not bind pig TIGIT. In some embodiments an antibody that specifically binds human TIGIT, does not bind cynomolgus monkey TIGIT. In some embodiments an antibody that specifically binds human TIGIT, does not bind rhesus monkey TIGIT.

In some embodiments of the methods described herein, an antibody that specifically binds human TIGIT comprises the heavy chain variable region and the light chain variable region from antibody OMP-313M32. In some embodiments, the antibody comprises the heavy chain variable region encoded by the plasmid deposited with ATCC as Designation No. PTA-122346. In some embodiments, the antibody comprises a polypeptide comprising the heavy chain variable region encoded by the plasmid deposited with ATCC as Designation No. PTA-122346. In some embodiments, the antibody comprises the light chain variable region encoded by the plasmid deposited with ATCC as Designation No. PTA-122347. In some embodiments, the antibody comprises the light chain encoded by the plasmid deposited with ATCC as Designation No. PTA-122347. In some embodiments, the antibody comprises the heavy chain variable region encoded by the plasmid deposited with ATCC as Designation No. PTA-122346 and the light chain variable region encoded by the plasmid deposited with ATCC as Designation No. PTA-122347. In some embodiments, the antibody comprises a polypeptide encoded by the plasmid deposited with ATCC as PTA-122346 and a polypeptide encoded by the plasmid deposited with ATCC as Designation No. PTA-122347.

In some embodiments of the methods described herein, the TIGIT-binding agent is monovalent. In some embodiments, the TIGIT-binding agent is bivalent. In some embodiments, the TIGIT-binding agent is monospecific. In some embodiments, the TIGIT-binding agent is bispecific. In some embodiments, the bispecific agent is a heterodimeric agent or heterodimeric molecule. In some embodiments, a heterodimeric agent comprises an antibody that specifically binds TIGIT. In some embodiments, the bispecific agent is a homodimeric agent or homodimeric molecule. In some embodiments, a homodimeric agent comprises an antibody that specifically binds TIGIT.

In some embodiments of the methods described herein, the TIGIT-binding agent is an antibody that competes for specific binding to human TIGIT with an antibody described herein. In some embodiments, a TIGIT-binding agent binds the same epitope on human TIGIT as an antibody described herein. In some embodiments, a TIGIT-binding agent binds an epitope on human TIGIT that overlaps with the epitope on TIGIT bound by an antibody described herein. In some embodiments, a TIGIT-binding agent binds an epitope comprising amino acids within SEQ ID NO:27. In some embodiments, a TIGIT-binding agent binds an epitope comprising amino acids within SEQ ID NO:28. In some embodiments, a TIGIT-binding agent binds an epitope comprising amino acids within SEQ ID NO:27 and SEQ ID NO:28. In some embodiments, a TIGIT-binding agent binds an epitope comprising amino acids Q62 and I109 of SEQ ID NO:1. In some embodiments, a TIGIT-binding agent binds an epitope comprising amino acids Q62 and T119 of SEQ ID NO:1. In some embodiments, a TIGIT-binding agent binds an epitope comprising amino acids Q64 and I109 of SEQ ID NO:1. In some embodiments, a TIGIT-binding agent binds an epitope comprising amino acids Q64 and T119 of SEQ ID NO:1. In some embodiments, a TIGIT-binding agent binds an epitope comprising amino acids Q62, Q64, and I109 of SEQ ID NO:1. In some embodiments, a TIGIT-binding agent binds an epitope comprising amino acids Q62, Q64, and T119 of SEQ ID NO:1. In some embodiments, a TIGIT-binding agent binds an epitope comprising amino acids Q62, I109, and T119 of SEQ ID NO:1. In some embodiments, a TIGIT-binding agent binds an epitope comprising amino acids Q64, I109, and T119 of SEQ ID NO:1. In some embodiments, a TIGIT-binding agent binds an epitope comprising amino acids Q62, Q64, I109, and T119 of SEQ ID NO:1. In some embodiments, a TIGIT-binding agent binds an epitope comprising at least one amino acid selected from the group consisting of: N58, E60, Q62, Q64, L65, F107, I109, H111, T117, T119, G120, and R121 of SEQ ID NO:1. In some embodiments, the epitope is a conformational epitope. In some embodiments, a TIGIT-binding agent binds an epitope that does not comprise amino acid V100 of SEQ ID NO:1.

In some embodiments of the methods described herein, the agent that specifically binds TIGIT is an antibody, wherein the antibody is part of a bispecific agent. In some embodiments, a bispecific agent comprises a first arm which binds TIGIT and a second arm which binds a second target. In some embodiments, a bispecific agent comprises a first arm that specifically binds TIGIT and a second arm, wherein the first arm comprises an anti-TIGIT antibody. In some embodiments, a bispecific agent comprises a first arm that binds TIGIT and a second arm which comprises an antigen-binding site from an antibody. In some embodiments, a bispecific agent comprises a first arm that binds TIGIT and a second arm that specifically binds PD-1, PD-L1, CTLA4, TIM-3, LAG-3, OX-40, or GITR. In some embodiments, a bispecific agent comprises a first arm that binds TIGIT and a second arm that specifically binds a tumor antigen. In some embodiments, a bispecific agent comprises a first arm that binds TIGIT and a second arm that comprises an immune response stimulating agent. In some embodiments, the immune response stimulating agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA4 antibody, anti-PD-1 antibody, anti-PD-L1 antibody, anti-GITR antibody, anti-OX-40 antibody, anti-LAG-3 antibody, and anti-TIM-3 antibody.

In some embodiments, the bispecific agent is a heterodimeric agent or heterodimeric molecule. In some embodiments, the bispecific agent is a homodimeric agent or homodimeric molecule. In some embodiments, a heterodimeric molecule comprises a first arm which binds human TIGIT and a second arm which binds a second target. In some embodiments, a heterodimeric molecule comprises a first arm that specifically binds human TIGIT and a second arm, wherein the first arm comprises an anti-TIGIT antibody. In some embodiments, a heterodimeric molecule comprises a first arm that binds human TIGIT and a second arm which comprises an antigen-binding site from an antibody that specifically binds a second target. In some embodiments, a heterodimeric molecule is a bispecific antibody. In some embodiments, a heterodimeric molecule comprises a first arm that binds human TIGIT and a second arm that specifically binds a tumor antigen. In some embodiments, a heterodimeric molecule comprises a first arm that binds human TIGIT and a second arm that specifically binds PD-1, PD-L1, CTLA-4, TIM-3, LAG-3, OX-40, 4-1BB, or GITR. In some embodiments, a heterodimeric molecule comprises a first arm that binds TIGIT and a second arm that comprises an immunotherapeutic agent. In some embodiments, the immunotherapeutic agent is selected from the group consisting of: granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), 4-1BB ligand, GITRL, OX-40L, anti-CD3 antibody, anti-CTLA-4 antibody, anti-PD-1 antibody, anti-PD-L1 antibody, anti-4-1BB antibody, anti-GITR antibody, anti-OX-40 antibody, anti-LAG-3 antibody, and anti-TIM-3 antibody.

In some embodiments of the methods described herein, an agent specifically binds TIGIT and inhibits binding of TIGIT to PVR. In some embodiments, an agent specifically binds TIGIT and inhibits or blocks the interaction between TIGIT and PVR. In some embodiments, an agent specifically binds TIGIT and inhibits binding of TIGIT to PVRL2. In some embodiments, an agent specifically binds TIGIT and inhibits or blocks the interaction between TIGIT and PVRL2. In some embodiments, an agent specifically binds TIGIT and inhibits binding of TIGIT to PVRL3. In some embodiments, an agent specifically binds TIGIT and inhibits or blocks the interaction between TIGIT and PVRL3. In some embodiments, the agent is an antagonist of TIGIT. In some embodiments, an agent specifically binds TIGIT and inhibits TIGIT signaling. In some embodiments, an agent specifically binds TIGIT and is an antagonist of TIGIT-mediated signaling. In some embodiments, an agent specifically binds TIGIT and inhibits TIGIT activation. In some embodiments, an agent specifically binds TIGIT and inhibits phosphorylation of TIGIT. In some embodiments, an agent specifically binds TIGIT and decreases cell surface expression of TIGIT.

In some embodiments of the methods described herein, an agent specifically binds TIGIT and induces, activates, promotes, increases, enhances, and/or prolongs an immune response. In some embodiments, the immune response is directed to (e.g., kills) a tumor or tumor cell. In some embodiments, the agent increases cell-mediated immunity. In some embodiments, the agent increases T-cell activity. In some embodiments, the agent increases cytolytic T-cell (CTL) activity. In some embodiments, the agent increases natural killer (NK) cell activity. In some embodiments, the agent increases IL-2 production and/or the number of IL-2-producing cells. In some embodiments, the agent increases IFN-gamma production and/or the number of IFN-gamma-producing cells. In some embodiments, the agent increases a Th1-type immune response. In some embodiments, the agent decreases IL-4 production and/or the number of IL-4-producing cells. In some embodiments, the agent decreases IL-10 and/or the number of IL-10-producing cells. In some embodiments, the agent decreases IL-6 production and/or the number of IL-6-producing cells. In some embodiments, the agent decreases IL-5 production and/or the number of IL-5-producing cells. In some embodiments, the agent decreases a Th2-type immune response. In some embodiments, the agent decreases the number of Treg cells. In some embodiments, the agent decreases Treg activity. In some embodiments, the agent inhibits and/or decreases the suppressive activity of Tregs. In some embodiments, the agent decreases the number of myeloid-derived suppressor cells (MDSCs). In some embodiments, the agent inhibits and/or decreases the suppressive activity of MDSCs.

In some embodiments of the methods described herein, an agent specifically binds TIGIT and inhibits tumor growth. In some embodiments, the agent reduces tumor growth. In some embodiments, the agent reduces tumor growth to an undetectable size. In some embodiments, the agent induces long-term anti-tumor immunity.

In another aspect, the invention provides compositions comprising a TIGIT-binding agent for use in the methods described herein. In some embodiments, the invention provides pharmaceutical compositions comprising a TIGIT-binding agent for use in the methods described herein and a pharmaceutically acceptable carrier.

In certain embodiments of the methods described herein, the TIGIT-binding agent is isolated. In certain embodiments, the TIGIT-binding agent is substantially pure.

The invention also provides polynucleotides comprising a polynucleotide that encodes a TIGIT-binding agent. In some embodiments, the polynucleotide is isolated. In some embodiments, the invention provides vectors that comprise the polynucleotides, as well as cells that comprise the vectors and/or the polynucleotides. In some embodiments, the invention also provides cells comprising or producing a TIGIT-binding agent. In some embodiments, the cell is a monoclonal cell line.

In some embodiments of the methods described herein, a method further comprises administering at least one additional therapeutic agent. In some embodiments, the additional therapeutic agent is a chemotherapeutic agent. In some embodiments, the additional therapeutic agent is an antibody. In some embodiments, the additional therapeutic agent is an anti-PD-1 antibody, an anti-PD-L1 antibody, an anti-CTLA4 antibody, an anti-LAG-3 antibody, or an anti-TIM-3 antibody. In some embodiments, the additional therapeutic agent is an inhibitor of the Notch pathway, the Wnt pathway, or the RSPO/LGR pathway. In some embodiments, the additional therapeutic agent is an immunotherapeutic agent. As used herein, the phrase "immunotherapeutic agent" is used in the broadest sense and refers to a substance that directly or indirectly affects or modulates the immune system. In some embodiments, an immunotherapeutic agent is an agent that directly or indirectly stimulates the immune system by inducing activation or increasing activity of any of the immune system's components. As the TIGIT-binding agents are considered immunotherapeutic agents, this additional immunotherapeutic agent may be considered a "second" immunotherapeutic agent. In some embodiments, the second immunotherapeutic agent is selected from the group consisting of: GM-CSF, M-CSF, G-CSF, IL-2, IL-3, IL-12, IL-15, B7-1 (CD80), B7-2 (CD86), 4-1BB ligand, GITRL, OX-40 ligand, anti-CD3 antibody, anti-CTLA-4 antibody, anti-CD28 antibody, anti-PD-1 antibody, anti-PD-L1 antibody, anti-4-1BB antibody, anti-GITR antibody, anti-OX-40 antibody, anti-LAG-3 antibody, and anti-TIM-3 antibody. In some embodiments, the second immunotherapeutic agent is a fusion protein comprising: GM-CSF, M-CSF, G-CSF, IL-2, IL-3, IL-12, IL-15, B7-1 (CD80), B7-2 (CD86), 4-1BB ligand, GITRL, OX-40 ligand, or a fragment thereof. In some embodiments, the second immunotherapeutic agent is a fusion protein comprising at least one copy of the extracellular domain of GITRL, OX40 ligand, or 4-1BB ligand.

In some embodiments of the methods described herein, the subject is human. In some embodiments, the subject has had a tumor or a cancer, at least partially, removed.

In some embodiments of the methods described herein, the tumor or the cancer expresses PD-L1. In some embodiments, a method further comprises a step of determining the level of PD-L1 expression in the tumor or cancer. In some embodiments, determining the level of PD-L1 expression is done prior to treatment or contact with a TIGIT-binding agent. In some embodiments, if the tumor or cancer has an elevated expression level of PD-L1, a TIGIT-binding agent is administered to the subject.

In some embodiments, the invention comprises a method of inhibiting tumor growth in a subject, comprising administering to the subject a therapeutically effective amount of an antibody that specifically binds the extracellular domain of human TIGIT, wherein the tumor is a head and neck cancer, esophageal/gastroesophageal cancer, gastric cancer, colorectal cancer, anal cancer, hepatocellular cancer/liver cancer, cervical cancer, lung cancer (e.g., NSCLC), melanoma, Merkel cell carcinoma, renal cell carcinoma/kidney cancer, bladder cancer, ovarian cancer, pancreatic cancer, endometrial cancer, and triple negative breast cancer, a known MSI high solid tumor (including MSI CRC) or a MSS colorectal cancer; wherein the tumor is resistant or refractory to treatment with an anti-PD-1 antibody or an anti-PD-L1 antibody; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments of the methods described herein, the subject has previously been treated with an anti-PD-1 antibody or an anti-PD-L1 antibody. In some embodiments, the antibody that specifically binds the extracellular domain of human TIGIT is administered to the subject at a dose of about 0.1 mg/kg, about 0.3 mg/kg, about 1 mg/kg, about 1.5 mg/kg, about 2 mg/kg, about 2.5 mg/kg, about 3 mg/kg, about 5 mg/kg, about 7.5 kg/kg, or about 10 mg/kg. In some embodiments, the antibody that specifically binds the extracellular domain of human TIGIT is administered once about every week, once about every two weeks, once about every three weeks, or once about every four weeks. In some embodiments, the subject has a histologically confirmed advanced relapsed or refractory solid tumor.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

FIG. 2. A schematic diagram showing dose escalation and expansion for the initial phase of a clinical trial using anti-TIGIT antibody 313M32.

DETAILED DESCRIPTION OF THE INVENTION

Figure 1:
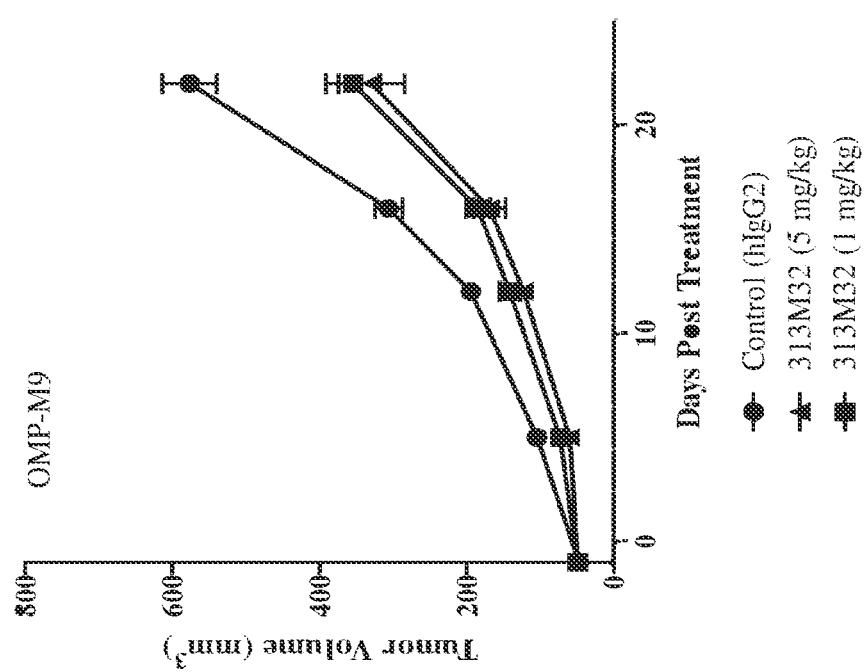
FIG. 1. Inhibition of tumor growth by anti-TIGIT antibody OMP-313M32 in a humanized mouse model. Humanized mice were injected subcutaneously with patient-derived melanoma tumor cells (OMP-M9, 75,000 cells/mouse). Tumors were allowed to grow 19 days until they had reached an average volume of approximately 50 mm$^3$. Tumor-bearing mice were randomized into groups (n=8 mice per group). Tumor-bearing mice were treated with either a control antibody or anti-TIGIT antibody OMP-313M32. Mice were dosed every 5 days at 1 mg/kg or 5 mg/kg. Tumor growth was monitored and tumor volumes were measured with electronic calipers at the indicated time points.

The present invention provides methods of using novel agents, wherein the agents include, but not limited to, polypeptides, antibodies, heterodimeric molecules, and homodimeric molecules that specifically bind human TIGIT. Methods of using the novel agents for inhibiting tumor growth and/or for treating cancer are provided. Methods of using the novel agents, such as methods of activating an immune response, methods of stimulating an immune response, methods of promoting an immune response, methods of increasing an immune response, methods of activating natural killer (NK) cells and/or T-cells, methods of increasing the activity of NK cells and/or T-cells, methods of promoting the activity of NK cells and/or T-cells, methods of decreasing and/or inhibiting suppressor T-cells (i.e., regulatory T-cells), and/or methods of decreasing and/or inhibiting myeloid-derived suppressor cells are further provided.

I. Definitions

To facilitate an understanding of the present invention, a number of terms and phrases are defined below.

The terms "agonist" and "agonistic" as used herein refer to or describe an agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein.

The terms "antagonist" and "antagonistic" as used herein refer to or describe an agent that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein.

The terms "modulation" and "modulate" as used herein refer to a change or an alteration in a biological activity. Modulation includes, but is not limited to, stimulating an activity or inhibiting an activity. Modulation may be an increase or a decrease in activity, a change in binding characteristics, or any other change in the biological, functional, or immunological properties associated with the activity of a protein, a pathway, a system, or other biological targets of interest.

The term "antibody" as used herein refers to an immunoglobulin molecule that recognizes and specifically binds a target through at least one antigen-binding site. The target may be a protein, polypeptide, peptide, carbohydrate, polynucleotide, lipid, or a combination of any of the foregoing. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies, bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and generally refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain or the variable region of an antibody heavy chain, either alone or in combination. Generally, the variable region of a heavy chain or a light chain consists of four framework regions connected by three complementarity determining regions (CDRs), also known as "hypervariable regions". The CDRs in each chain are held together in close proximity by the framework regions and, with the CDRs from the other chain, contribute to the formation of the antigen-binding site(s) of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda Md.), and (2) an approach based on crystallographic studies of antigen-antibody complexes (Al Lazikani et al., 1997, *J. Mol. Biol.*, 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies that recognize different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The term "humanized antibody" as used herein refers to antibodies that are specific immunoglobulin chains, chimeric immunoglobulins, or fragments thereof that contain minimal non-human sequences. Typically, humanized antibodies are human immunoglobulins in which amino acid residues of the CDRs are replaced by amino acid residues from the CDRs of a non-human species (e.g., mouse, rat, rabbit, or hamster) that have the desired specificity, affinity, and/or binding capability. In some instances, the framework variable region amino acid residues of a human immunoglobulin may be replaced with the corresponding amino acid residues in an antibody from a non-human species. The humanized antibody can be further modified by the substitution of additional amino acid residues either in the framework variable region and/or within the replaced non-human amino acid residues to further refine and optimize antibody specificity, affinity, and/or binding capability. The humanized antibody may comprise variable domains containing all or substantially all of the CDRs that correspond to the non-human immunoglobulin, whereas all or substantially all of the framework variable regions are those of a human immunoglobulin sequence. In some embodiments, the variable domains comprise the framework regions of a human immunoglobulin sequence. In some embodiments, the variable domains comprise the framework regions of a human immunoglobulin consensus sequence. The humanized antibody can also comprise at least a portion of an immunoglobulin constant region or domain (Fc), typically that of a human immunoglobulin.

The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable regions of the light and heavy chains correspond to the variable regions of an antibody derived from one species of mammal (e.g., mouse, rat, rabbit, etc.) with the desired specificity, affinity, and/or binding capability, while the constant regions are homologous to the sequence in an antibody derived from another species.

The terms "epitope" and "antigenic determinant" are used interchangeably herein and refer to that portion of an antigen or target capable of being recognized and specifically bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

The terms "selectively binds" or "specifically binds" mean that an agent interacts more frequently, more rapidly, with greater duration, with greater affinity, or with some combination of the above to the epitope, protein, or target molecule than with alternative substances, including related and unrelated proteins. In certain embodiments "specifically binds" means, for instance, that an agent binds a protein or target with a $K_D$ of about 0.1 mM or less, but more usually less than about 1 µM. In certain embodiments, "specifically binds" means that an agent binds a target with a $K_D$ of at least about 0.1 µM or less, at least about 0.01 µM or less, or at least about 1 nM or less. Because of the sequence identity between homologous proteins in different species, specific binding can include an agent that recognizes a protein or target in more than one species (e.g., mouse TIGIT and human TIGIT). Likewise, because of homology within certain regions of polypeptide sequences of different proteins, specific binding can include an agent that recognizes more than one protein or target. It is understood that, in certain embodiments, an agent that specifically binds a first target may or may not specifically bind a second target. As such, "specific binding" does not necessarily require (although it can include) exclusive binding, i.e. binding to a single target. Thus, an agent may, in certain embodiments, specifically bind more than one target. In certain embodiments, multiple targets may be bound by the same antigen-binding site on the agent. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. Generally, but not necessarily, reference to binding means specific binding.

As used herein. "selecting" and "selected" in reference to a patient is used to mean that a particular patient is specifically chosen from a larger group of patients on the basis of (due to) the particular patient having a predetermined criteria, e.g., the patient has a tumor with an elevated expression level of PVR and/or PVRL2. Similarly, "selectively treating a patient having a tumor" refers to providing treatment to a cancer patient that is specifically chosen from a larger group of patients on the basis of (due to) the particular patient having a predetermined criteria, e.g., the patient has a tumor with an elevated expression level of PVR and/or PVRL2. Similarly, "selectively administering" refers to administering a drug to a cancer patient that is specifically chosen from a larger group of patients on the basis of (due to) the particular patient having a predetermined criteria, e.g., the patient the patient has a tumor with an elevated expression level of PVR and/or PVRL2. By selecting, selectively treating and selectively administering, it is meant that a patient is delivered a personalized therapy for cancer based on the patient's cancer biology, rather than being delivered a standard treatment regimen based solely on the patient having a cancer, such as CRC or NSCLC.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or other members of the immunoglobulin superfamily, in certain embodiments, a "polypeptide" can occur as a single chain or as two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, the coding region of a nucleotide sequence.

A "conservative amino acid substitution" is one in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies of the invention do not abrogate the binding of the polypeptide or antibody containing the amino acid sequence, to the target binding site. Methods of identifying nucleotide and amino acid conservative substitutions which do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "immune response" as used herein includes responses from both the innate immune system and the adaptive immune system. It includes both cell-mediated and/or humoral immune responses. It includes, but is not limited to, both T-cell and B-cell responses, as well as responses from other cells of the immune system such as natural killer (NK) cells, monocytes, macrophages, etc.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (non-cancerous) or malignant (cancerous) including pre-cancerous lesions.

The term "metastasis" as used herein refers to the process by which a cancer spreads or transfers from the site of origin to other regions of the body with the development of a similar cancerous lesion at a new location. Generally, a "metastatic" or "metastasizing" cell is one that loses adhesive contacts with neighboring cells and migrates via the bloodstream or lymph from the primary site of disease to secondary sites throughout the body.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "subject" refers to any animal (e.g., a mammal), including, but not limited to, humans, non-human primates, canines, felines, rabbits, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier, or adjuvant" or "acceptable pharmaceutical carrier" refer to an excipient, carrier, or adjuvant that can be administered to a subject, together with at least one agent of the present disclosure, and which does not destroy the pharmacological activity thereof and is non-toxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of an agent, an antibody, a polypeptide, a polynucleotide, a small organic molecule, or other drug effective to "treat" a disease or disorder in a subject such as, a mammal. In the case of cancer or a tumor, the therapeutically effective amount of an agent (e.g., polypeptide or antibody) has a therapeutic effect and as such can enhance or boost the immune response, enhance or boost the anti-tumor response, increase cytolytic activity of immune cells, increase killing of tumor cells, increase killing of tumor cells by immune cells, reduce the number of tumor cells; decrease tumorigenicity, tumorigenic frequency, or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods of the present invention if the patient shows one or more of the following: an increased immune response, an increased anti-tumor response, increased cytolytic activity of immune cells, increased killing of tumor cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Use and Pharmaceutical Compositions

The TIGIT-binding agents of the invention are useful in a variety of applications including, but not limited to, therapeutic treatment methods, such as treatment of cancer. In some embodiments, the therapeutic treatment methods comprise immunotherapy for cancer. In certain embodiments, a TIGIT-binding agent is useful for activating, promoting, increasing, and/or enhancing an immune response, inhibiting tumor growth, reducing tumor volume, increasing tumor cell apoptosis, and/or reducing the tumorigenicity of a tumor.

The present invention provides methods for inhibiting tumor growth using a TIGIT-binding agent. In certain embodiments, the method of inhibiting tumor growth comprises administering to a subject a therapeutically effective amount of a TIGIT-binding agent. In some embodiments, the TIGIT-binding agent is an antibody that specifically binds the extracellular domain of human TIGIT. In certain embodiments, the subject is a human. In certain embodiments, the subject has a tumor or the subject had a tumor which was at least partially removed.

In some embodiments, the invention provides a method of inhibiting tumor growth (e.g., treating cancer) in a subject, comprising administering to the subject a therapeutically effective amount of a TIGIT-binding agent, wherein the tumor is a microsatellite instability-high colorectal cancer (MSI CRC), a microsatellite stable colorectal cancer (MSS CRC), a triple negative breast cancer (TNBC), a Merkel cell carcinoma, an endometrial cancer, or an esophageal cancer. In some embodiments, a method of inhibiting tumor growth (e.g., treating cancer) in a subject, comprising administering to the subject a therapeutically effective amount of an antibody that specifically binds the extracellular domain of human TIGIT, wherein the tumor is a microsatellite instability-high colorectal cancer (MSI CRC), a microsatellite stable colorectal cancer (MSS CRC), a triple negative breast cancer (TNBC), a Merkel cell carcinoma, an endometrial cancer, or an esophageal cancer; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is an esophageal cancer. In some embodiments, the tumor is an esophageal cancer that has progressed on at least one prior systemic therapy or line of treatment for unresectable and/or metastatic disease. In some embodiments, the tumor is a triple-negative breast cancer. In some embodiments, the tumor is a triple negative breast cancer that has been histologically confirmed as an incurable, advanced estrogen receptor-neg, progesterone receptor-neg, and human epidermal growth factor receptor 2-neg adenocarcinoma of the breast.

In some embodiments, histological confirmation is conducted by a skilled artisan, such as a trained clinical physician, using any method known in the art, such as immunohistochemistry.

In some embodiments, the invention provides a method of inhibiting tumor growth (e.g., treating cancer) in a subject, comprising administering to the subject a therapeutically effective amount of a TIGIT-binding agent, wherein the tumor is a solid tumor with high MSI. In some embodiments, a method of inhibiting tumor growth (e.g., treating cancer) in a subject, comprising administering to the subject a therapeutically effective amount of an antibody that specifically binds the extracellular domain of human TIGIT, wherein the tumor is a solid tumor with high MSI; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments the solid tumor with high MSI can include a MSI CRC, a MSI gastric cancer, a MSI endometrium cancer, a MSI ovarian cancer, a MSI hepatobiliary tract cancer, a MSI urinary tract cancer, a MSI brain cancer, or a MSI skin cancer.

Generally, tumors can be classified according to their microsatellite stability (MSI). For example, solid tumors can be classified as MSI-high, MSI-low or MSI-stable tumors. MSI-high tumors can include, without limitation, colon cancer, gastric cancer, endometrium cancer, ovarian cancer, hepatobiliary tract cancer, urinary tract cancer, brain cancer and skin cancer. MSI can be determined using any method known in the art, such as polymerase chain reaction (PCR) or immunohistochemistry (IHC). In some embodiments, MSI is determined in a sample obtained from a cancer patient. In some embodiments the sample is a biopsy sample (e.g., needle biopsy). In some embodiments, MSI is determined in a polymerase chain reaction (PCR) based method, such as but not limited to, reverse transcription PCR (RT-PCR), quantitative RT-PCR (qPCR), TaqMan™®, or TaqMan™® low density array (TLDA). In some embodiments, the MSI is determined using a microarray. In some embodiments, MSI is determined by DNA sequencing, such as next-generation sequencing. In some embodiments, MSI is determined in an immunohistochemistry (IHC) assay. In some embodiments, a tumor MSI is compared to a predetermined MSI. In some embodiments, a tumor is classified as a MSI-high tumor if the MSI in the tumor is higher than the predetermined MSI. In some embodiments, the predetermined MSI is the MSI in a reference tumor sample, a reference normal tissue sample, a series of reference tumor samples, or a series of reference normal tissue samples.

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor is a microsatellite instability-high colorectal cancer, a microsatellite stable colorectal cancer, a triple negative breast cancer, a Merkel cell carcinoma, an endometrial cancer, or an esophageal cancer. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the tumor is a microsatellite instability-high colorectal cancer, a microsatellite stable colorectal cancer, a triple negative breast cancer, a Merkel cell carcinoma, an endometrial cancer, or an esophageal cancer, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a method of inhibiting tumor growth (e.g., treating cancer) in a subject, comprises administering to the subject a therapeutically effective amount of an antibody that specifically binds the extracellular domain of human TIGIT in combination with a PD-L1 antagonist, wherein the tumor is a microsatellite instability-high colorectal cancer, a microsatellite stable colorectal cancer, a triple negative breast cancer, a Merkel cell carcinoma, an endometrial cancer, or an esophageal cancer, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is an esophageal cancer. In some embodiments, the tumor is an esophageal cancer that has progressed on at least one prior systemic therapy or line of treatment for unresectable and/or metastatic disease. In some embodiments, the tumor is a triple-negative breast cancer. In some embodiments, the tumor is a triple negative breast cancer that has been histologically confirmed as an incurable, advanced estrogen receptor-neg, progesterone receptor-neg, and human epidermal growth factor receptor 2-neg adenocarcinoma of the breast.

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor is a solid tumor with high MSI. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the tumor is a solid tumor with high MSI, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a method of inhibiting tumor growth (e.g., treating cancer) in a subject, comprises administering to the subject a therapeutically effective amount of an antibody that specifically binds the extracellular domain of human TIGIT in combination with a PD-L1 antagonist, wherein the tumor is a solid tumor with high MSI, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments the solid tumor with high microsatellite instability can include a MSI CRC, a MSI gastric cancer, a MSI endometrium cancer, a MSI ovarian cancer, a MSI hepatobiliary tract cancer, a MSI urinary tract cancer, a MSI brain cancer, or a MSI skin cancer.

In some embodiments, the invention provides a method of inhibiting tumor growth (e.g., treating cancer) in a subject, comprising administering to the subject a therapeutically effective amount of a TIGIT-binding agent, wherein the tumor is resistant or refractory to treatment with a PD-1 antagonist or a PD-L1 antagonist. In some embodiments, a method of inhibiting tumor growth (e.g., treating cancer) in a subject, comprises administering to the subject a therapeutically effective amount of an antibody that specifically binds the extracellular domain of human TIGIT, wherein the tumor is resistant or refractory to treatment with a PD-1 antagonist, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is resistant or refractory to treatment with an anti-PD-1 antibody. In some embodiments, a method of inhibiting tumor growth (e.g., treating cancer) in a subject, comprises administering to the subject a therapeutically effective amount of an antibody that specifically binds the extracellular domain of human TIGIT, wherein the tumor is resistant or refractory to treatment with a PD-L1 antagonist, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is resistant or refractory to treatment with an anti-PD-L1 antibody.

In some embodiments, the tumor that is resistant or refractory to treatment with a PD-1 antagonist or a PD-L1 antagonist is selected from the group consisting of melanoma, NSCLC, renal cell carcinoma, squamous cell carcinoma of the head and neck, urothelial carcinoma, colorectal cancer (e.g. MSI or dMMR metastatic CRC) and hepatocellular carcinoma.

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor is resistant or refractory to treatment with a PD-1 antagonist as a single agent or a PD-L1 antagonist as a single agent. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the tumor is resistant or refractory to treatment with a PD-1 antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the PD-1 antagonist is an anti-PD-1 antibody. In some embodiments, the anti-PD-1 antibody is pembrolizumab (KEYTRUDA®). In some embodiments, the anti-PD-1 antibody is nivolumab (OPDIVO®). In some embodiments, a method of inhibiting tumor growth (treating cancer) in a subject, comprises administering to the subject a therapeutically effective amount of an antibody that specifically binds the extracellular domain of human TIGIT in combination with a PD-L1 antagonist, wherein the tumor is resistant or refractory to treatment with a PD-L1 antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the PD-L1 antagonist is an anti-PD-L1 antibody. In some embodiments, the anti-PD-L1 antibody is atezolizumab (TECENTRIQ®). In some embodiments, the anti-PD-L1 antibody is avelumab (MSB0010718C).

In some embodiments, the tumor is resistant or refractory to treatment with a PD-1 antagonist as a single agent or a PD-L1 antagonist as a single agent can include a melanoma, a NSCLC, a renal cell carcinoma, a squamous cell carcinoma of the head and neck, a urothelial carcinoma, a colorectal cancer (e.g. MSI or dMMR metastatic CRC) and a hepatocellular carcinoma.

In some embodiments, the invention provides a method of inhibiting tumor growth (e.g., treating cancer) in a subject, comprising administering to the subject a therapeutically effective amount of a TIGIT-binding agent, wherein the subject has previously been treated with a PD-1 antagonist or a PD-L1 antagonist. In some embodiments, a method of inhibiting tumor growth (e.g., treating cancer) in a subject, comprises administering to the subject a therapeutically effective amount of an antibody that specifically binds the extracellular domain of human TIGIT, wherein the subject has previously been treated with a PD-1 antagonist, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a method of inhibiting tumor growth (e.g., treating cancer) in a subject, comprises administering to the subject a therapeutically effective amount of an antibody that specifically binds the extracellular domain of human TIGIT, wherein the subject has previously been treated with a PD-L1 antagonist, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with a PD-1 antagonist or a PD-L1 antagonist as a single agent. In some embodiments, the subject has previously been treated with a PD-1 antagonist or a PD-L1 antagonist, wherein there was disease progression on or after treatment. Subjects that have disease progression on or after a specific treatment may be referred to herein as "progressors". In some embodiments, the subject has previously been treated with an anti-PD-1 antibody as a first-line treatment. In some embodiments, the subject has previously been treated with an anti-PD-1 antibody as a second-line or third-line treatment. In some embodiments, the subject has previously been treated with pembrolizumab (KEYTRUDA®). In some embodiments, the subject has previously been treated with nivolumab (OPDIVO®). In some embodiments, the subject has previously been treated with an anti-PD-L1 antibody as a first-line treatment. In some embodiments, the subject has previously been treated with an anti-PD-L1 antibody as a second-line or third-line treatment. In some embodiments, the subject has previously been treated with atezolizumab (TECENTRIQ®). In some embodiments, the subject has previously been treated with avelumab (MSB0010718C). In some embodiments, the subject has previously been treated with a PD-1 antagonist or a PD-L1 antagonist as part of a combination therapy. In some embodiments, the subject has previously been treated with an anti-PD-1 antibody and a second checkpoint inhibitor. In some embodiments, the subject has previously been treated with an anti-PD-1 antibody and an anti-CTLA-4 antibody. In some embodiments, the subject has previously been treated with nivolumab (OPDIVO®) and ipilimumab (YERVOY®). In some embodiments, the subject has previously been treated with an anti-PD-1 antibody and a chemotherapeutic agent. In some embodiments, the subject has previously been treated with an anti-PD-L1 antibody and a second checkpoint inhibitor. In some embodiments, the subject has previously been treated with an anti-PD-L1 antibody and an anti-CTLA-4 antibody. In some embodiments, the subject has previously been treated with an anti-PD-L1 antibody and ipilimumab (YERVOY®). In some embodiments, the subject has previously been treated with an anti-PD-L1 antibody and a chemotherapeutic agent.

In some embodiments, the invention provides a method of inhibiting tumor growth (e.g., treating cancer) in a subject, comprising administering to the subject a therapeutically effective amount of a TIGIT-binding agent in combination with a PD-1 antagonist, wherein the subject has previously been treated with a PD-1 antagonist or a PD-L1 antagonist. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the subject has previously been treated with a PD-1 antagonist; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with an anti-PD-1 antibody. In some embodiments, the subject has previously been treated with pembrolizumab (KEYTRUDA®). In some embodiments, the subject has previously been treated with nivolumab (OPDIVO®). In some embodiments, tumor growth progressed during treatment with an anti-PD-1 antibody. In some embodiments, tumor growth recurred after treatment with an anti-PD-1 antibody. In some embodiments, the tumor is responsive to a combination therapy of the anti-TIGIT antibody and an anti-PD-1 antibody. In some embodiments, the tumor is responsive to a combination therapy of the anti-TIGIT antibody and an anti-PD-1 antibody, wherein the response is better than the response obtained with administration of the anti-TIGIT antibody alone. In some embodiments, a method of inhibiting tumor growth (treating cancer) in a subject, comprises administering to the subject a therapeutically effective amount of an antibody that specifically binds the extracellular domain of human TIGIT in combination with a PD-L1 antagonist, wherein the subject has previously been treated with a PD-L1 antagonist as a single agent; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with an anti-PD-L1 antibody. In some embodiments, the subject has previously been treated with atezolizumab (TECENTRIQ®). In some embodiments, the subject has previously been treated with avelumab (MSB0010718C). In some embodiments, tumor growth progressed during treatment with an anti-PD-L1 antibody. In some embodiments, tumor growth recurred after treatment with an anti-PD-L1 antibody. In some embodiments, the tumor is responsive to a combination therapy of the anti-TIGIT antibody and an anti-PD-L1 antibody. In some embodiments, the tumor is responsive to a combination therapy of the anti-TIGIT antibody and an anti-PD-L1 antibody, wherein the response is better than the response obtained with administration of the anti-TIGIT antibody alone.

In some embodiments, the tumor in the subject previously treated with a PD-1 antagonist or a PD-L1 antagonist can have a tumor such as a melanoma, a NSCLC, a renal cell carcinoma, a squamous cell carcinoma of the head and neck, a urothelial carcinoma, a colorectal cancer (e.g. MSI or dMMR metastatic CRC) or a hepatocellular carcinoma.

In some embodiments, the invention provides a method of inhibiting tumor growth (e.g., treating cancer) in a subject, comprising administering to the subject a therapeutically effective amount of a TIGIT-binding agent, wherein the tumor/cancer expresses PVR and/or PVRL2. In some embodiments, a method of inhibiting tumor growth (e.g., treating cancer) in a subject, comprises administering to the subject a therapeutically effective amount of an antibody that specifically binds the extracellular domain of human TIGIT, wherein the tumor/cancer expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a tumor sample is obtained from the subject and the expression level of PVR and/or PVRL2 is determined. In some embodiments, the expression level of PVR is used to select a subject for treatment. In some embodiments, the expression level of PVRL2 is used to select a subject for treatment.

In some embodiments, the invention provides a method of inhibiting tumor growth (e.g., treating cancer) in a subject, comprising selectively administering to the subject a therapeutically effective amount of a TIGIT-binding agent, on the basis that the tumor/cancer expresses PVR and/or PVRL2. In some embodiments, a method of inhibiting tumor growth (e.g., treating cancer) in a subject, comprises selectively administering to the subject a therapeutically effective amount of an antibody that specifically binds the extracellular domain of human TIGIT, on the basis that the tumor/cancer expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the tumor/cancer expressing PVR and/or PVRL2 includes a NSCLC, a renal cell carcinoma, a squamous cell carcinoma of the head and neck, a urothelial carcinoma, a colorectal cancer (e.g. MSI or dMMR metastatic CRC) or a hepatocellular carcinoma.

In some embodiments, the tumor/cancer expressing PVR and/or PVRL2 includes a CRC, a gastric cancer, a endometrium cancer, a ovarian cancer, a hepatobiliary tract cancer, a urinary tract cancer, a brain cancer, or a skin cancer.

In some embodiments, the tumor/cancer expressing PVR and/or PVRL2 includes a MSI CRC, a MSI gastric cancer, a MSI endometrium cancer, a MSI ovarian cancer, a MSI hepatobiliary tract cancer, a MSI urinary tract cancer, a MSI brain cancer, or a MSI skin cancer.

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor expresses PVR and/or PVRL2. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the tumor expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a method of inhibiting tumor growth (e.g., treating cancer) in a subject, comprises administering to the subject a therapeutically effective amount of an antibody that specifically binds the extracellular domain of human TIGIT in combination with a PD-L1 antagonist, wherein the tumor expresses PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the anti-TIGIT antibody is administered in combination with an anti-PD-1 antibody. In some embodiments, the anti-TIGIT antibody is administered in combination with pembrolizumab (KEYTRUDA®). In some embodiments, the anti-TIGIT antibody is administered in combination with nivolumab (OPDIVO®). In some embodiments, the anti-TIGIT antibody is administered in combination with an anti-PD-L1 antibody. In some embodiments, the anti-TIGIT antibody is administered in combination with atezolizumab (TECENTRIQ®).

In some embodiments, the expression level of PVR and/or PVRL2 in a tumor sample is determined to be at a high level.

In some embodiments, the expression level of PVR in the sample is compared to a pre-determined expression level of PVR. In some embodiments, the expression level of PVRL2 in the sample is compared to a pre-determined expression level of PVRL2. In some embodiments, the pre-determined expression level of PVR expression is an expression level of PVR in a reference tumor sample, a reference normal tissue sample, a series of reference tumor samples, or a series of reference normal tissue samples. In some embodiments, the pre-determined expression level of PVRL2 expression is an expression level of PVRL2 in a reference tumor sample, a reference normal tissue sample, a series of reference tumor samples, or a series of reference normal tissue samples. In some embodiments, the expression level of PVR or PVRL2 is determined using an immunohistochemistry (IHC) assay. In some embodiments, the expression level of PVR and/or PVRL2 is determined using an assay which comprises an H-score evaluation. In some embodiments, the expression level of PVR is determined using an antibody that specifically binds PVR. In some embodiments, the expression level of PVRL2 is determined using an antibody that specifically binds PVRL2. In some embodiments, PVR is detected on tumor cells. In some embodiments, the PVRL2 is detected on tumor cells. In some embodiments, PVR is detected on tumor-infiltrating immune cells and/or in the tumor microenvironment. In some embodiments, PVRL2 is detected on tumor-infiltrating immune cells and/or in the tumor microenvironment.

In certain embodiments, the expression level of PVR and/or PVRL2 is determined using PCR-based methods, such as but not limited to, reverse transcription PCR (RT-PCR), quantitative RT-PCR (qPCR), TaqMan™®, or TaqMan™® low density array (TLDA). In some embodiments, the expression level of a biomarker is determined using a microarray.

In certain embodiments, the expression level PVR and/or PVRL2 is determined using protein-based methods. In some embodiments, the expression level of a biomarker is measured or determined by multi-analyte profile testing, radioimmunoassay (RIA), Western blot assay, immunofluorescent assay, enzyme immunoassay, enzyme linked immunosorbent assay (ELISA), immunoprecipitation assay, chemiluminescent assay, immunohistochemical (IHC) assay, dot blot assay, or slot blot assay. In some embodiments, the expression level of PVR and/or PVRL2 is determined using an IHC assay. In some embodiments, the assay uses an antibody (e.g., as anti-PVR or PVRL2 antibody). In some embodiments wherein the assay uses an antibody, the antibody is detectably labeled. In some embodiments, the label is selected from the group consisting of an immunofluorescent label, a chemiluminescent label, a phosphorescent label, an enzyme label, a radiolabel, an avidin/biotin label, colloidal gold particles, colored particles, and magnetic particles.

In some embodiments, the determining of the level of PVR and/or PVRL2 expression is done prior to treatment with a TIGIT-binding agent. In some embodiments, if a tumor or cancer has an elevated expression level of PVR and/or PVRL2, a TIGIT-binding agent is administered to the subject. In some embodiments, a method comprises (i) obtaining a tumor sample from the subject; (ii) measuring the expression level of PVR and/or PVRL2 in the sample; and (iii) administering an effective amount of a TIGIT-binding agent to the subject if the tumor or cancer has an elevated or high expression level of PVR and/or PVRL2.

In some embodiments, the invention provides a method of inhibiting tumor growth (e.g., treating cancer) in a subject, comprising selectively administering to the subject a therapeutically effective amount of a TIGIT-binding agent in combination with a PD-1 antagonist or a PD-L1 antagonist, on the basis that the tumor has an elevated expression level of PVR and/or PVRL2. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist, wherein the tumor has an elevated expression level of PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, a method of inhibiting tumor growth (e.g., treating cancer) in a subject, comprises selectively administering to the subject a therapeutically effective amount of an antibody that specifically binds the extracellular domain of human TIGIT in combination with a PD-L1 antagonist, on the basis that the tumor has an elevated expression level of PVR and/or PVRL2; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the anti-TIGIT antibody is administered in combination with an anti-PD-1 antibody. In some embodiments, the anti-TIGIT antibody is administered in combination with pembrolizumab (KEYTRUDA®). In some embodiments, the anti-TIGIT antibody is administered in combination with nivolumab (OPDIVO®). In some embodiments, the anti-TIGIT antibody is administered in combination with an anti-PD-L1 antibody. In some embodiments, the anti-TIGIT antibody is administered in combination with atezolizumab (TECENTRIQ®).

In some embodiments, the sample is a biopsy sample. In some embodiments, the sample comprises tumor cells, tumor-infiltrating immune cells, stromal cells, and any combination thereof. In some embodiments, the sample is a formalin-fixed paraffin embedded (FFPE) sample. In some embodiments, the sample is archival, fresh, or frozen tissue.

Some patients have tumors with an active immune microenvironment. These tumors are referred to as "inflamed" or "hot" tumors and are characterized by the presence of, for example, tumor-infiltrating lymphocytes (TILs), IFN-gamma producing CD8+ T-cells, and expression of PD-L1. In some studies, inflamed or hot tumors have been associated with clinical response to immunotherapies.

Thus in some embodiments, the invention provides a method of inhibiting tumor growth (e.g., treating cancer) in a subject, comprising administering to the subject a therapeutically effective amount of a TIGIT-binding agent, wherein the tumor comprises TILs. In some embodiments, a method of inhibiting tumor growth (e.g., treating cancer) in a subject, comprises administering to the subject a therapeutically effective amount of an antibody that specifically binds the extracellular domain of human TIGIT, wherein the tumor comprises TILs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor comprises a high level of TILs as compared to a predetermined level. In some embodiments, the level of TILs is an absolute number of TILs. In some embodiments, the level of TILs is a percentage of a total cell number.

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor comprises TILs. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist or a PD-L1 antagonist, wherein the tumor comprises TILs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor comprises a high level of TILs as compared to a predetermined level. In some embodiments, the level of TILs is an absolute number of TILs. In some embodiments, the level of TILs is a percentage of a total cell number. In some embodiments, the anti-TIGIT antibody is administered in combination with an anti-PD-1 antibody. In some embodiments, the anti-TIGIT antibody is administered in combination with pembrolizumab (KEYTRUDA®). In some embodiments, the anti-TIGIT antibody is administered in combination with nivolumab (OPDIVO®). In some embodiments, the anti-TIGIT antibody is administered in combination with an anti-PD-L1 antibody. In some embodiments, the anti-TIGIT antibody is administered in combination with atezolizumab (TECENTRIQ®).

In some embodiments, the invention provides a method of inhibiting tumor growth (e.g., treating cancer) in a subject, comprising administering to the subject a therapeutically effective amount of a TIGIT-binding agent, wherein the tumor comprises a high level of regulatory T-cells (Tregs). In some embodiments, a method of inhibiting tumor growth (e.g., treating cancer) in a subject, comprises administering to the subject a therapeutically effective amount of an antibody that specifically binds the extracellular domain of human TIGIT, wherein the tumor comprises a high level of Tregs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:7), and a light chain CDR3 comprising QQHYSTP (SEQ ID NO:8).

In some embodiments, the invention provides a method of inhibiting tumor growth (e.g., treating cancer) in a subject, comprising administering to the subject a therapeutically effective amount of a TIGIT-binding agent in combination with a PD-1 antagonist or a PD-L1 antagonist, wherein the tumor comprises a high level of Tregs. In some embodiments, a method of inhibiting tumor growth (e.g., treating cancer) in a subject, comprises administering to the subject a therapeutically effective amount of an antibody that specifically binds the extracellular domain of human TIGIT in combination with a PD-1 antagonist or a PD-L1 antagonist, wherein the tumor comprises a high level of Tregs; and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the anti-TIGIT antibody is administered in combination with an anti-PD-1 antibody. In some embodiments, the anti-TIGIT antibody is administered in combination with pembrolizumab (KEYTRUDA®). In some embodiments, the anti-TIGIT antibody is administered in combination with nivolumab (OPDIVO®). In some embodiments, the anti-TIGIT antibody is administered in combination with an anti-PD-L1 antibody. In some embodiments, the anti-TIGIT antibody is administered in combination with atezolizumab (TECENTRIQ®).

In some embodiments, the presence of immune cells (e.g., TILs, Tregs, Teffs) in a tumor or within the tumor microenvironment is analyzed by assessing expression of specific proteins on or in the cells. Commonly used methods for the analysis of protein expression, include but are not limited to, immunohistochemistry (IHC)-based, antibody-based, and mass spectrometry-based methods. In some embodiments, protein expression on or in an immune cell is determined by an assay known to those of skill in the art, including but not limited to, multi-analyte profile test, enzyme-linked immunosorbent assay (ELISA), radioimmunoassay, Western blot assay, immunofluorescent assay, enzyme immunoassay, immunoprecipitation assay, chemiluminescent assay, immunohistochemical (IHC) assay, dot blot assay, or slot blot assay. Antibodies, generally monoclonal antibodies, may be used to detect expression of a gene product (e.g., protein). In some embodiments, the antibodies can be detected by direct labeling of the antibodies themselves. In other embodiments, an unlabeled primary antibody is used in conjunction with a labeled secondary antibody.

In some embodiments, the expression of a specific protein is determined using an agent that specifically binds that protein. Any molecular entity that displays specific binding to the protein can be employed to assess the expression of the protein in a sample. Specific binding agents include, but are not limited to, antibodies, antibody mimetics, and polynucleotides (e.g., aptamers). One of skill understands that the degree of specificity required is determined by the particular assay used to detect the protein.

CD45 (leukocyte common antigen, LCA; including all proteins in the CD45 family) is used as a marker for immune cells, including lymphocytes, NK cells, macrophages, monocytes, etc. T-cell can be separated into different subsets, including but not limited to, CD4+ T-cells or CD8+ T-cells. In some embodiments, CD45 is used as a marker for TILs in a tumor sample. In some embodiments, TILs are detected and/or assessed using an anti-CD45 antibody. In some embodiments, a cocktail of monoclonal anti-CD45 antibodies are used, each of which recognizes a different CD45 isotype and/or different epitopes. In some embodiments, TILs are detected and/or assessed using an anti-CD4 antibody. In some embodiments, TILs are detected and/or assessed using an anti-CD8 antibody.

It is known by those of skill in the art that FOXP3 is a regulatory T-cell (Treg) marker and can be used to detect and/or identify Tregs in a tumor sample. Studies have shown that Treg cells are comprised of many subpopulations with different functions and one subpopulation has been identified to be FOXP3+ and TIGIT+. In some embodiments, Tregs are detected and/or assessed by FOXP3 expression. In some embodiments, FOXP3 expression is detected and/or assessed using an anti-FOXP3 antibody. In some embodiments, a cocktail of monoclonal anti-FOXP3 antibodies are used, each of which recognizes a different isotype and/or different epitopes. In some embodiments, Tregs are detected and/or assessed by FOXP3 and TIGIT expression. In some embodiments, the TIGIT expression is detected and/or assessed using an anti-TIGIT antibody.

In some embodiments, wherein an antibody is used in the assay the antibody is detectably labeled. Examples of detectable substances include various enzymes, prosthetic groups, fluorescent materials, phosphorescent materials, luminescent materials, bioluminescent materials, chemiluminescent materials, radioactive materials, avidin/biotin, colloidal gold particles, colored particles and magnetic particles. Examples of suitable enzymes include horseradish peroxidase, alkaline phosphatase, ?-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

In some embodiments, the expression of CD45, CD4, CD8, FOXP3, and/or TIGIT is determined using an IHC assay. For example, FFPE sections are cut from a tumor sample and mounted on coated glass slides. Tissues are deparaffinized and rehydrated by successively incubating them in xylene, 100% ethanol, 95% ethanol, 70% ethanol, and distilled water for antigen retrieval. Slides are placed into retrieval solution and placed in a decloaker for antigen retrieval. To block endogenous peroxidase activity slides are incubated in hydrogen peroxide and washed in PBS. To block non-specific background staining slides are incubated in blocker. Slides are incubated with an anti-PD-L1 antibody. Specific binding is detected using a kit including diaminobenzidine (DAB). The sections are counterstained with hematoxylin. In some embodiments, the FFPE sections are mounted on coated glass slides and stained using an automated system, e.g., on a Ventana BenchMark® ULTRA instrument using Ventana reagents.

In some embodiments, the antibody is a polyclonal antibody. In some embodiments, the antibody is a monoclonal antibody. In some embodiments, the antibody is a mouse antibody that binds a human biomarker (e.g., CD45, CD4, CD8, FOXP3, TIGIT). In some embodiments, the antibody is a rabbit antibody that binds a human biomarker (e.g., CD45, CD4, CD8, FOXP3, TIGIT). In some embodiments, the antibody is a goat antibody that binds a human biomarker (e.g., CD45, CD4, CD8, FOXP3, TIGIT).

IHC slides may be analyzed using an automated instrument or evaluated manually by microscope. The staining intensity of each cell (0: no expression, 1: weak expression, 2: moderate expression, 3: strong expression) is measured and cells of each staining level are counted and a percentage for each type is calculated. The data is combined into a weighted H-score for each tissue section: H-score=[3×(% 3+cells)]+[2×(% 2+cells)]+[1×(% 1+cells)]. Using these parameters, the highest score available is H-score=300. In some embodiments, an H-score of 1 or less is considered negative. In some embodiments, the IHC assay has a cut-off value. In some embodiments, the IHC assay has a cut-off value for specificity. In some embodiments, the IHC assay has a cut-off value for efficacy. In some embodiments, the IHC assay has a cut-off value determined by screening of positive and negative tumor tissues. In some embodiments, the IHC assay has a cut-off value of about 25. In some embodiments, the IHC assay has a cut-off value of about 30, about 40, about 50, about 60, about 70, about 80, about 90, about 100, or about 110, or about 120.

Other suitable methods for analyzing the expression level of a biomarker include proteomics-based methods. Proteomics includes, among other things, study of the global changes of protein expression in a sample. In some embodiments, a proteomic method comprises the following steps: (1) separation of individual proteins in a sample by 2-D electrophoresis (2-D PAGE), (2) identification of individual proteins recovered from the gel (e.g., by mass spectrometry or N-terminal sequencing), and (3) analysis of the data using bioinformatics. In some embodiments, a proteomic method comprises using a tissue microarray (TMA). Tissue arrays may be constructed according to a variety of techniques known to one of skill in the art. In certain embodiments, a manual tissue arrayer is used to remove a "core" from a paraffin block prepared from a tissue sample. The core is then inserted into a separate paraffin block in a designated location on a grid. Cores from as many as about 400 samples can be inserted into a single recipient block. The resulting tissue array may be processed into thin sections for analysis. In some embodiments, a proteomic method comprises an antibody microarray. In some embodiments, a proteomic method comprises using mass spectrometry, including but not limited to, SELDI, MALDI, electro spray, and surface plasmon resonance methods. In some embodiments, a proteomic method comprises bead-based technology, including but not limited to, antibodies on beads in an array format. In some embodiments, the proteomic method comprises a reverse phase protein microarray (RPPM). In some embodiments, the proteomic method comprises multiplexed protein profiling, including but not limited to, the Global Proteome Survey (GPS) method.

Other suitable methods for analyzing the expression level of a biomarker include, but are not limited to, methods based on analyses of polynucleotide expression, sequencing of polynucleotides, and/or analyses of protein expression. For example, determination of biomarker expression levels may be performed by detecting the expression of mRNA expressed from the genes of interest, and/or by detecting the expression of a polypeptide encoded by the genes.

Commonly used methods for the analysis of polynucleotides, include Southern blot analysis, Northern blot analysis, and in situ hybridization, RNAse protection assays, and polymerase chain reaction (PCR)-based methods, such as reverse transcription polymerase chain reaction (RT-PCR), quantitative PCR (qPCR) as known as real-time PCR, TaqMan™®, TaqMan™® low density array (TLDA), anchored PCR, competitive PCR, rapid amplification of cDNA ends (RACE), and microarray analyses. RT-PCR is a quantitative method that can be used to compare mRNA levels in different samples to examine gene expression profiles. A variation of RT-PCR is real time quantitative PCR, which measures PCR product accumulation through a dual-labeled fluorigenic probe (e.g., TaqMan™® probe). There are many other PCR-based techniques known to one of skill in the art, including but not limited to, differential display, amplified fragment length polymorphism, BeadArray™ technology, high coverage expression profiling (Hi-CEP) and digital PCR. Representative methods for sequencing-based gene expression analyses include Serial Analysis of Gene Expression (SAGE), Massively Parallel Signature Sequencing (MPSS), and NexGen sequencing analysis, including mRNA sequencing.

In certain embodiments, biomarker expression is determined using a qPCR assay. For example, total RNA is extracted from a fresh frozen (FF) tissue sample or total RNA is extracted from a macro-dissected formalin-fixed paraffin embedded (FFPE) tissue sample. The quantity and quality of the total RNA is assessed by standard spectrophotometry and/or any other appropriate method (e.g., an Agilent Bioanalyzer). Following RNA extraction, the RNA sample is reverse transcribed using standard methods and/or a commercially available cDNA synthesis kit (e.g., Roche Transcriptor First Strand cDNA synthesis kit). The resultant cDNA is pre-amplified using, for example, an ABI pre-amplification kit. Expression of the biomarker(s) (e.g., CD45, CD4, CD8, Foxp3, TIGIT, other immune response genes) is assessed on, for example, a Roche Lightcycler® 480 system (Roche Diagnostics) using an ABI TaqMan® Gene Expression Mastermix. qPCR reactions are performed in triplicate. For each assay a subset of the samples is run without reverse transcription (the RT-neg control), as well as, control samples run without template. A universal human reference RNA sample is included on each plate to act as a positive control. Suitable reference genes are identified from a standard panel of reference genes. Candidate reference genes are selected with different cellular functions to eliminate risk of co-regulation. The most suitable reference genes are evaluated and selected using specific software and algorithms (e.g., Genex software; GeNorm and Normfinder algorithms). The expression level of each biomarker is normalized using the selected optimum reference genes. In some embodiments, these normalized (or standardized) expression values for each biomarker are used to calculate the decision value of the sample. In some embodiments, these normalized (or standardized) expression values for each biomarker are used to calculate an expression level.

In some embodiments, biomarker expression is determined using a PCR-based assay comprising specific primers and/or probes for a human biomarker (e.g., CD45, CD4, CD8, Foxp3, TIGIT). As used herein, the term "probe" refers to any molecule that is capable of selectively binding a specifically intended target biomolecule. Probes can be synthesized by one of skill in the art using known techniques, or derived from biological preparations. Probes may include but are not limited to, RNA, DNA, proteins, peptides, aptamers, antibodies, and organic molecules. The term "primer" or "probe" encompasses oligonucleotides that have a sequence of a specific SEQ ID NO or oligonucleotides that have a sequence complementary to a specific SEQ ID NO. In some embodiments, the probe is modified. In some embodiments, the probe is modified with a quencher. In some embodiments, the probe is labeled. Labels can include, but are not limited to, colorimetric, fluorescent, chemiluminescent, or bioluminescent labels.

Alternatively, biomarker expression levels may be determined by amplifying complementary DNA (cDNA) or complementary RNA (cRNA) produced from mRNA and analyzing it using a microarray. Microarray technology allows for simultaneous analysis of the expression of thousands of genes. A number of different array configurations and methods for their production are known to those skilled in the art. In addition, microarrays are commercially available (e.g., Affymetrix GeneChips®) or can be custom-produced. Microarrays currently in wide use include cDNA arrays and oligonucleotide arrays. In general, polynucleotides of interest (e.g., probes or probe sets) are plated, or arrayed, on a microchip substrate. In some embodiments, probes to at least 10, 25, 50, 100, 500, 1000, 5000, 10,000, 20,000, or 25,000 or more genes are immobilized on an array substrate. The substrate may be a porous or nonporous support, such as a glass, plastic or gel surface. The probes can include DNA, RNA, copolymer sequences of DNA and RNA, DNA and/or RNA analogues, or combinations thereof. In some embodiments, a microarray includes a support with an ordered array of binding sites for each individual gene. The microarrays can be addressable arrays or positionally addressable arrays, e.g., each probe of the array is located at a known, predetermined position on the solid support such that the identity of each probe can be determined from its position of the array.

Each probe on the microarray can be between 10-50,000 nucleotides in length. In some embodiments, the probes of the microarray can consist of nucleotide sequences with lengths of less than about 1,000 nucleotides, less than about 750 nucleotides, less than about 500 nucleotides, less than about 250 nucleotides, less than about 100 nucleotides, or less than about 50 nucleotides in length. Generally, an array includes positive control probes and negative control probes.

In certain embodiments, biomarker expression is determined using a microarray. For example, total RNA is extracted from a fresh frozen (FF) tissue sample or total RNA is extracted from a macro-dissected formalin-fixed paraffin embedded (FFPE) tissue sample. The quantity and quality of the total RNA is assessed by standard spectrophotometry and/or any other appropriate technology (e.g., an Agilent Bioanalyzer). Following RNA extraction, the RNA sample is amplified using standard methods and/or a commercially available amplification system (e.g., NuGEN Ovation® RNA Amplification System V2). The amplified cDNA is fragmented, labeled, and hybridized to a microarray (e.g., using NuGEN Encore® Biotin Module and Affymetrix GeneChip array) following standard procedures. The array is washed, stained, and scanned in accordance with the instructions for the microarray. The microarray data is pre-processed, the probe-level intensity measurements are background corrected, normalized, and summarized as expression measurements using the Robust Multichip algorithm (RMA). The probe level data is summarized to get the expression level of each biomarker (e.g., CD45, CD4, CD8, Foxp3, TIGIT). A combination of quality parameter threshold and data reduction techniques (e.g., principal component analysis) is applied to the data set to establish profile quality and identify potential outlying samples. These normalized (or standardized) expression values for each biomarker are used to calculate the decision value of the sample.

In some embodiments of any of the methods described herein, the tumor/cancer is selected from the group consisting of: lung, liver, breast, renal cell carcinoma/kidney, prostate, gastrointestinal/gastric, melanoma, cervical, bladder, glioblastoma, head and neck, pancreatic, ovarian, colorectal, endometrial, and esophageal. In some embodiments, a colorectal cancer is a microsatellite instability-high colorectal cancer. In some embodiments, a colorectal cancer is a microsatellite stable colorectal cancer. In some embodiments, an esophageal tumor is a histologically confirmed unresectable, advanced or recurrent esophageal or gastroesophageal junction cancer. In some embodiments, an esophageal tumor is a tumor that progressed on at least one prior systemic therapy or line of treatment for unresectable or metastatic disease. In some embodiments, a colorectal tumor is a histologically confirmed incurable, advanced adenocarcinoma of the colon or rectum. In some embodiments, a colorectal tumor is a tumor that has been treated with at least one prior line of standard chemotherapies for colorectal cancer or metastatic colorectal cancer and is refractory to or is progressing on those therapies. In some embodiments, a colorectal tumor is a tumor that has been treated with at least two prior lines of standard chemotherapies for colorectal cancer or metastatic colorectal cancer and is refractory to or is progressing on those therapies. In some embodiments, a liver tumor or hepatocellular tumor is a histologically confirmed advanced hepatocellular carcinoma, not eligible for surgical and/or locoregional therapies. In some embodiments, a liver tumor or hepatocellular tumor is progressing or has progressed after surgical and/or locoregional therapies. In some embodiments, a cervical tumor is a histologically confirmed recurrent or metastatic cervical cancer. In some embodiments, a cervical tumor is a tumor that progressed on at least one prior line of chemotherapy for cervical cancer. In some embodiments, a breast tumor is a triple-negative breast cancer. In some embodiments, a breast tumor has been histologically confirmed as an incurable, advanced estrogen receptor-neg, progesterone receptor-neg, and human epidermal growth factor receptor 2-neg adenocarcinoma of the breast. In some embodiments, a head and neck tumor is a histologically confirmed recurrent or metastatic squamous cell carcinoma of the head and neck (SCCHN), not amenable to standard curative or palliative therapies. In some embodiments, a head and neck tumor includes, but is not limited to, squamous cell carcinoma of the oral cavity, nasal cavity, paranasal sinuses, nasopharynx, oropharynx, hypopharynx or larynx. In some embodiments, a head and neck tumor includes primary or recurrent cancer for which no curative or established palliative treatments are amenable.

In some embodiments of the methods described here, the invention provides use of a TIGIT-binding agent in the manufacture or preparation of a medicament for inhibiting growth of a tumor or tumor cell. In some embodiments of the methods described here, the invention provides use of a TIGIT-binding agent in the manufacture or preparation of a medicament for the treatment of cancer. In some embodiments, a TIGIT-binding agent binds human TIGIT and inhibits or reduces growth of the cancer. In certain embodiments, the tumor/cancer comprises cancer stem cells. In certain embodiments, the frequency of cancer stem cells in the tumor/cancer is reduced. In certain embodiments, the subject is a human. In certain embodiments, the subject has had a tumor at least partially removed.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of a TIGIT-binding agent and at least one additional therapeutic agent results in additive or synergistic results. In some embodiments, the combination therapy results in an increase in the therapeutic index of the TIGIT-binding agent. In some embodiments, the combination therapy results in an increase in the therapeutic index of the additional therapeutic agent(s). In some embodiments, the combination therapy results in a decrease in the toxicity and/or side effects of the TIGIT-binding agent. In some embodiments, the combination therapy results in a decrease in the toxicity and/or side effects of the additional therapeutic agent(s).

In certain embodiments of the methods described herein, in addition to administering a TIGIT-binding agent, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that may be administered in combination with the TIGIT-binding agents include chemotherapeutic agents. Thus, in some embodiments, the method or treatment involves the administration of a TIGIT-binding agent in combination with a chemotherapeutic agent or in combination with a cocktail of chemotherapeutic agents. Treatment with a TIGIT-binding agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4$^{th}$ Edition, 2008, M. C. Perry, Editor, Lippincott, Williams & Wilkins, Philadelphia, Pa.

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

Chemotherapeutic agents useful in the instant invention include, but are not limited to, alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL™) and docetaxel (TAXOTERE®); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA®); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL™), docetaxel (TAXOTERE®), albumin-bound paclitaxel (ABRAXANE®), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In certain embodiments, the additional therapeutic agent is albumin-bound paclitaxel (ABRAXANE®).

In some embodiments, an additional therapeutic agent comprises an agent such as a small molecule. For example, treatment can involve the combined administration of an agent of the present invention with a small molecule that acts as an inhibitor against tumor-associated antigens including, but not limited to, EGFR, HER2 (ErbB2), and/or VEGF. In some embodiments, an agent of the present invention is administered in combination with a protein kinase inhibitor selected from the group consisting of: gefitinib (IRESSA®), erlotinib (TARCEVA®), sunitinib (SUTENT®), lapatinib, vandetanib (ZACTIMA®), AEE788, CI-1033, cediranib (RECENTIN®), sorafenib (NEXAVAR®), and pazopanib (GW786034B). In some embodiments, an additional therapeutic agent comprises an mTOR inhibitor.

In certain embodiments, the additional therapeutic agent is an agent that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the RSPO/LGR pathway. In some embodiments, the additional therapeutic agent is an inhibitor of the mTOR/AKR pathway.

In some embodiments of the methods described herein, an additional therapeutic agent comprises a biological molecule, such as an antibody. For example, treatment can involve the combined administration of a TIGIT-binding agent with an antibody against a tumor-associated antigen including, but not limited to, an antibody that binds EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN®), ramucirumab, trastuzumab (HERCEPTIN®), pertuzumab (OMNITARG™), panitumumab (VECTIBIX® nimotuzumab, zalutumumab, or cetuximab (ERBITUX®).

In certain embodiments of the methods described herein, in addition to administering a TIGIT-binding agent, the method or treatment further comprises administering at least one additional immunotherapeutic agent. In some embodiments, the additional immunotherapeutic agent is an immune response stimulating agent. In some embodiments, the immunotherapeutic agent (e.g., immune response stimulating agent) includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), an antibody that blocks immunosuppressive functions (e.g., an anti-CTLA4 antibody, anti-CD28 antibody, anti-CD3 antibody, anti-PD-1 antibody, anti-PD-L1 antibody), an antibody that enhances immune cell functions (e.g., an anti-GITR antibody or an anti-OX-40 antibody), a toll-like receptor (e.g., TLR4, TLR7, TLR9), a soluble ligand (e.g., GITRL or OX-40L), or a member of the B7 family (e.g., CD80, CD86). An additional immunotherapeutic agent (e.g., an immune response stimulating agent) can be administered prior to, concurrently with, and/or subsequently to, administration of the TIGIT-binding agent. Pharmaceutical compositions comprising a TIGIT-binding agent and an additional immunotherapeutic agent (e.g., an immune response stimulating agent(s)) are also provided. In some embodiments, the immunotherapeutic agent comprises 1, 2, 3, or more immunotherapeutic agents. In some embodiments, the immune response stimulating agent comprises 1, 2, 3, or more immune response stimulating agents.

In some embodiments of the methods described herein, the additional therapeutic agent is an antibody that is an immune checkpoint inhibitor. In some embodiments, the immune checkpoint inhibitor is an anti-PD-1 antibody, an anti-PD-L1 antibody, an anti-CTLA4 antibody, an anti-CD28 antibody, an anti-LAG3 antibody, an anti-TIM3 antibody, an anti-GITR antibody, or an anti-OX-40 antibody. In some embodiments, the immune checkpoint inhibitor is an anti-4-1BB antibody. In some embodiments, the additional therapeutic agent is an anti-PD-1 antibody selected from the groups consisting of: nivolumab (OPDIVO®), pembrolizumab (KEYTRUDA®), or pidilzumab. In some embodiments, the additional therapeutic agent is an anti-PD-1 antibody selected from the groups consisting of: MEDI0680, REGN2810, BGB-A317, and PDR001. In some embodiments, the additional therapeutic agent is an anti-PD-L1 antibody selected from the group consisting of: BMS935559 (MDX-1105), atezolizumab (TECENTRIQ®), durvalumab (MEDI4736), or avelumab (MSB0010718C). In some embodiments, the additional therapeutic agent is an anti-CTLA-4 antibody selected from the group consisting of: ipilimumab (YERVOY®) or tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566.

Furthermore, treatment with a TIGIT-binding agent can include combination treatment with other biologic molecules, such as one or more cytokines (e.g., lymphokines, interleukins, interferons, tumor necrosis factors, and/or growth factors) or can be accompanied by surgical removal of tumors, removal of cancer cells, or any other therapy deemed necessary by a treating physician.

In some embodiments, the TIGIT-binding agent can be administered in combination with a biologic molecule selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, PIGF, gamma-IFN, IL-1, IL-2, IL-3, IL-4, IL-5, IL-6, IL-7, IL-12, IL-15, and IL-18. In some embodiments, the TIGIT-binding agent can be administered in combination with a biologic molecule selected from the group consisting of: macrophage colony stimulating factor (M-CSF) and stem cell factor (SCF), In some embodiments of the methods described herein, treatment with a TIGIT-binding agent can be accompanied by surgical removal of tumors, removal of cancer cells, or any other surgical therapy deemed necessary by a treating physician.

In certain embodiments of the methods described herein, treatment involves the administration of a TIGIT-binding agent in combination with radiation therapy. Treatment with a TIGIT-binding agent can occur prior to, concurrently with, or subsequent to administration of radiation therapy. Dosing schedules for such radiation therapy can be determined by the skilled medical practitioner.

Combined administration can include co-administration, either in a single pharmaceutical formulation or using separate formulations, or consecutive administration in either order but generally within a time period such that all active agents can exert their biological activities simultaneously.

It will be appreciated that the combination of a TIGIT-binding agent and at least one additional therapeutic agent may be administered in any order or concurrently. In some embodiments, a TIGIT-binding agent will be administered to patients that have previously undergone treatment with a second/different therapeutic agent. In certain other embodiments, the TIGIT-binding agent and a second additional therapeutic agent will be administered substantially simultaneously or concurrently. For example, a subject may be given a TIGIT-binding agent while undergoing a course of treatment with an additional therapeutic agent (e.g., chemotherapy). In certain embodiments, a TIGIT-binding agent will be administered within 1 year of the treatment with the second therapeutic agent. In certain alternative embodiments, a TIGIT-binding agent will be administered within 10, 8, 6, 4, or 2 months of any treatment with a second therapeutic agent. In certain other embodiments, a TIGIT-binding agent will be administered within 4, 3, 2, or 1 weeks of any treatment with a second therapeutic agent. In some embodiments, an agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a TIGIT-binding agent depends on the type of disease to be treated, the severity and course of the disease, the responsiveness of the disease, whether the agent is administered for therapeutic or preventative purposes, previous therapy, the patient's clinical history, and so on, all at the discretion of the treating physician. The TIGIT-binding agent can be administered one time or over a series of treatments lasting from several days to several months, or until a cure is effected or a diminution of the disease state is achieved (e.g., reduction in tumor size). In some embodiments, the TIGIT-binding agent is administered over a series of treatments until there is disease progression. In some embodiments, optimal dosing schedules are calculated from measurements of drug accumulation in the body of the patient and will vary depending on the relative potency of an individual agent. The administering physician can determine optimum dosages, dosing methodologies, and repetition rates.

In certain embodiments of the methods described herein, dosage of the TIGIT-binding agent is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, a TIGIT binding agent is administered to a subject at a dose of about 0.1 mg/kg, about 0.3 mg/kg, about 1 mg/kg, about 1.5 mg/kg, about 2 mg/kg, about 2.5 mg/kg, about 3 mg/kg, about 5 mg/kg, about 7.5 kg/kg, about 10 mg/kg, about 12 mg/kg, about 12.5 mg/kg about 15 mg/kg, about 17.5 mg/kg, about 20 mg/kg or about 25 mg/kg. In certain embodiments, the dosage of the TIGIT-binding agent is from about 0.1 mg to about 20 mg/kg. In some embodiments, the dosage of the TIGIT-binding agent is about 0.3 mg/kg. In some embodiments, the dosage of the TIGIT-binding agent is about 1 mg/kg. In some embodiments, the dosage of the TIGIT-binding agent is about 1.5 mg/kg. In some embodiments, the dosage of the TIGIT-binding agent is about 2 mg/kg. In some embodiments, the dosage of the TIGIT-binding agent is about 2.5 mg/kg. In some embodiments, the dosage of the TIGIT-binding agent is about 3 mg/kg. In some embodiments, the dosage of the TIGIT-binding agent is about 5 mg/kg. In some embodiments, the dosage of the TIGIT-binding agent is about 7.5 mg/kg. In some embodiments, the dosage of the TIGIT-binding agent is about 10 mg/kg. In some embodiments, the dosage of the TIGIT-binding agent is about 12.5 mg/kg. In some embodiments, the dosage of the TIGIT-binding agent is about 15 mg/kg. In some embodiments, the dosage of the TIGIT-binding agent is about 17.5 mg/kg. In some embodiments, the dosage of the TIGIT-binding agent is about 20 mg/kg. In certain embodiments, the dosage can be given once or more daily, weekly, monthly, or yearly. In certain embodiments, the TIGIT-binding agent is given once every week, once every two weeks, once every three weeks, or once every four weeks.

In some embodiments, a TIGIT-binding agent may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

In some embodiments, the dosing schedule may be limited to a specific number of administrations or "cycles". In some embodiments, the agent is administered for 3, 4, 5, 6, 7, 8, or more cycles. For example, the agent is administered every 2 weeks for 6 cycles, the agent is administered every 3 weeks for 6 cycles, the agent is administered every 2 weeks for 4 cycles, the agent is administered every 3 weeks for 4 cycles, etc. Dosing schedules can be decided upon and subsequently modified by those skilled in the art.

In embodiments, the TIGIT binding agent is administered once about every week, once about every two weeks, once about every three weeks, once about every four weeks, once about every five weeks, once about every six weeks, once about every eight weeks, once about every twelve weeks, once about every month, once about every two months, once about every three months or longer. In certain embodiments, a TIGIT binding agent is administered to a subject at a dose of about 0.1 mg/kg, about 0.3 mg/kg, about 1 mg/kg, about 1.5 mg/kg, about 2 mg/kg, about 2.5 mg/kg, about 3 mg/kg, about 5 mg/kg, about 7.5 kg/kg, about 10 mg/kg, about 12 mg/kg, about 12.5 mg/kg about 15 mg/kg, about 17.5 mg/kg, about 20 mg/kg or about 25 mg/kg once about every two weeks.

In some embodiments, a TIGIT binding agent is administered to the subject at a dose of about 0.3 mg/kg once every two weeks.

In some embodiments, a TIGIT binding agent is administered to the subject at a dose of about 1 mg/kg once every two weeks.

In some embodiments, a TIGIT binding agent is administered to the subject at a dose of about 3 mg/kg once every two weeks.

In some embodiments, a TIGIT binding agent is administered to the subject at a dose of about 10 mg/kg once every two weeks.

In some embodiments, a TIGIT binding agent is administered to the subject at a dose of about 15 mg/kg once every two weeks.

In certain embodiments, the subject has received prior treatment with a PD-1 antagonist or a and/or a PD-L1 antagonist. In certain embodiments, the subject has a histologically confirmed advanced relapsed or refractory solid tumor.

In certain embodiments, the subject has head and neck cancer, esophageal/gastroesophageal cancer, gastric cancer, colorectal cancer, anal cancer, hepatocellular cancer/liver cancer, cervical cancer, lung cancer, melanoma, Merkel cell carcinoma, renal cell carcinoma/kidney cancer, bladder cancer, ovarian cancer, pancreatic cancer, endometrial cancer, anal cancer, triple negative breast cancer, a known MSI high solid tumor (including MSI CRC) or a MSS colorectal cancer.

The present invention provides methods of administering to a subject a TIGIT-binding agent comprising using an intermittent dosing strategy for administering one or more agents, which may reduce side effects and/or toxicities associated with administration of an agent, chemotherapeutic agent, etc. In some embodiments, a method for inhibiting tumor growth and/or treating cancer in a human subject comprises administering to the subject a therapeutically effective dose of a TIGIT-binding agent in combination with a therapeutically effective dose of a chemotherapeutic agent, wherein one or both of the agents are administered according to an intermittent dosing strategy. In some embodiments, the intermittent dosing strategy comprises administering an initial dose of a TIGIT-binding agent to the subject, and administering subsequent doses of the TIGIT-binding agent about once every 2 weeks. In some embodiments, the intermittent dosing strategy comprises administering an initial dose of a TIGIT-binding agent to the subject, and administering subsequent doses of the TIGIT-binding agent about once every 3 weeks. In some embodiments, the intermittent dosing strategy comprises administering an initial dose of a TIGIT-binding agent to the subject, and administering subsequent doses of the TIGIT-binding agent about once every 4 weeks. In some embodiments, the TIGIT-binding agent is administered using an intermittent dosing strategy and a second agent is administered weekly.

The present invention provides methods using compositions comprising TIGIT-binding agents. The present invention also provides methods described herein using pharmaceutical compositions comprising TIGIT-binding agents and a pharmaceutically acceptable vehicle. In some embodiments, the pharmaceutical compositions find use in immunotherapy. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified TIGIT-binding agent with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{st}$ Edition, 2012, Pharmaceutical Press, London.).

The pharmaceutical compositions of the present invention can be administered in any number of ways for either local or systemic treatment. In some embodiments, administration is (i) topical by epidermal or transdermal patches, ointments, lotions, creams, gels, drops, suppositories, sprays, liquids and powders; (ii) pulmonary by inhalation or insufflation of powders or aerosols, including by nebulizer, intratracheal, and intranasal; (iii) oral; or (iv) parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

TIGIT-binding agents can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, $22^{st}$ Edition, 2012, Pharmaceutical Press, London.

In certain embodiments, pharmaceutical formulations include a TIGIT-binding agent complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising a TIGIT-binding agent are produced. Suitable examples of sustained-release preparations include semi-permeable matrices of solid hydrophobic polymers containing an agent, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), sucrose acetate isobutyrate, and poly-D-(-)-3-hydroxybutyric acid.

III. TIGIT Binding Agents

T-cell immunoreceptor with Ig and ITIM domains (TIGIT) is a type I transmembrane glycoprotein that contains an immunoglobulin variable (IgV) domain. TIGIT belongs to the poliovirus receptor (PVR) family and binds to the poliovirus receptor (PVR; CD155) with high affinity and to PVRL-2 (CD112) and PVRL-3 (CD113) with a lower affinity. TIGIT is expressed on T-cells, including regulatory T-cells (Tregs) and memory T-cells, as well as on NK cells and is upregulated following activation of naïve CD4+ T-cells. The full-length amino acid (aa) sequence for human TIGIT (UniProtKB No. Q495A1) is known in the art and are provided herein as SEQ ID NO:1. As used herein, reference to amino acid positions refer to the numbering of full-length amino acid sequences including the signal sequence.

The present invention provides methods that use agents that specifically bind TIGIT. These agents are referred to herein as "TIGIT-binding agents". In some embodiments, the TIGIT-binding agent is an antibody. In some embodiments, the TIGIT-binding agent is a polypeptide. In certain embodiments, the TIGIT-binding agent binds mouse TIGIT. In certain embodiments, the TIGIT-binding agent binds human TIGIT. In certain embodiments, the TIGIT-binding agent binds mouse TIGIT and human TIGIT. In some embodiments, the TIGIT-binding agent binds human TIGIT and does not bind mouse TIGIT. Non-limiting examples of TIGIT-binding agents have been described in, for example, International Patent Application No. PCT/US2016/034549; International Patent Pub. Nos. WO 2016/106302 and WO 2016/028656; and U.S. Patent Application No. 2013/0251720.

In some embodiments, an agent binds TIGIT and interferes with the interaction of TIGIT with a second protein. In some embodiments, an agent binds TIGIT and interferes with the interaction of TIGIT with PVR. In some embodiments, an agent binds TIGIT and interferes with the interaction of TIGIT with PVRL2. In some embodiments, an agent binds TIGIT and interferes with the interaction of TIGIT with PVRL3. In some embodiments, an agent specifically binds TIGIT and the agent disrupts binding of TIGIT to PVR, and/or disrupts PVR activation of TIGIT signaling.

In certain embodiments, the TIGIT-binding agent is an antibody that specifically binds the extracellular domain of TIGIT, or a fragment thereof. In certain embodiments, the TIGIT-binding agent is an antibody that specifically binds the extracellular domain of mouse TIGIT, or a fragment thereof. In certain embodiments, the TIGIT-binding agent is an antibody that specifically binds the extracellular domain of human TIGIT, or a fragment thereof. In certain embodiments, the TIGIT-binding agent is an antibody that specifically binds the extracellular domain of mouse TIGIT and human TIGIT, or a fragment thereof. In some embodiments, the TIGIT-binding agent is an antibody that specifically binds the Ig-like domain of TIGIT. In some embodiments, the TIGIT-binding agent is an antibody that specifically binds the IgV domain of TIGIT. In some embodiments, the TIGIT-binding agent is an antibody that binds within amino acids 22-141 of human TIGIT. In some embodiments, the TIGIT-binding agent is an antibody that binds within amino acids 22-141 of SEQ ID NO:1. In some embodiments, the agent binds within amino acids 22-124 of human TIGIT. In some embodiments, the agent binds within amino acids 22-124 of SEQ ID NO:1. In certain embodiments, the TIGIT-binding agent binds within SEQ ID NO:3, or a fragment thereof. In some embodiments, the TIGIT-binding agent is an antibody that binds within amino acids 50-124 of human TIGIT. In some embodiments, the TIGIT-binding agent is an antibody that binds within amino acids 50-124 of SEQ ID NO:1. In certain embodiments, the TIGIT-binding agent binds within SEQ ID NO:3, or a fragment thereof.

In some embodiments, the TIGIT-binding agent is an antibody that binds an epitope comprising amino acids within SEQ ID NO:27. In some embodiments, the TIGIT-binding agent is an antibody that binds an epitope comprising amino acids within SEQ ID NO:28. In some embodiments, the TIGIT-binding agent is an antibody that binds an epitope comprising amino acids within SEQ ID NO:27 and SEQ ID NO:28. In some embodiments, the TIGIT-binding agent is an antibody that binds an epitope comprising amino acids Q62 and I109 of SEQ ID NO:1. In some embodiments, the TIGIT-binding agent is an antibody that binds an epitope comprising amino acids Q62 and T119 of SEQ ID NO:1. In some embodiments, the TIGIT-binding agent is an antibody that binds an epitope comprising amino acids Q64 and I109 of SEQ ID NO:1. In some embodiments, the TIGIT-binding agent is an antibody that binds an epitope comprising amino acids Q64 and T119 of SEQ ID NO:1. In some embodiments, the TIGIT-binding agent is an antibody that binds an epitope comprising amino acids Q62, Q64, and I109 of SEQ ID NO:1. In some embodiments, the TIGIT-binding agent is an antibody that binds an epitope comprising amino acids Q62, Q64, and T119 of SEQ ID NO:1. In some embodiments, the TIGIT-binding agent is an antibody that binds an epitope comprising amino acids Q62, I109, and T119 of SEQ ID NO:1. In some embodiments, the TIGIT-binding agent is an antibody that binds an epitope comprising amino acids Q64, I109, and T119 of SEQ ID NO:1. In some embodiments, the TIGIT-binding agent is an antibody that binds an epitope comprising amino acids Q62, Q64, I109, and T119 of SEQ ID NO:1. In some embodiments, the TIGIT-binding agent is an antibody that binds an epitope comprising at least one amino acid selected from the group consisting of: N58, E60, Q62, Q64, L65, F107, I109, H111, T117, T119, G120, and R121 of SEQ ID NO:1. In some embodiments, the epitope is a conformational epitope. In some embodiments, the TIGIT-binding agent is an antibody that binds an epitope which does not comprise amino acid V100 of SEQ ID NO:1.

In certain embodiments, the TIGIT-binding agent (e.g., an antibody) binds TIGIT with a dissociation constant ($K_D$) of about 1 µM or less, about 100 nM or less, about 40 nM or less, about 20 nM or less, about 10 nM or less, about 1 nM or less, about 0.1 nM or less, 50 µM or less, 10 µM or less, or 1 µM or less. In some embodiments, a TIGIT-binding agent binds TIGIT with a $K_D$ of about 20 nM or less. In some embodiments, a TIGIT-binding agent binds TIGIT with a $K_D$ of about 10 nM or less. In some embodiments, a TIGIT-binding agent binds TIGIT with a $K_D$ of about 1 nM or less. In some embodiments, a TIGIT-binding agent binds TIGIT with a $K_D$ of about 0.5 nM or less. In some embodiments, a TIGIT-binding agent binds TIGIT with a $K_D$ of about 0.1 nM or less. In some embodiments, a TIGIT-binding agent binds TIGIT with a $K_D$ of about 50 µM or less. In some embodiments, a TIGIT-binding agent binds TIGIT with a $K_D$ of about 25 µM or less. In some embodiments, a TIGIT-binding agent binds TIGIT with a $K_D$ of about 10 µM or less. In some embodiments, a TIGIT-binding agent binds TIGIT with a $K_D$ of about 1 µM or less. In some embodiments, the TIGIT-binding agent binds both human TIGIT and mouse TIGIT with a $K_D$ of about 10 nM or less. In some embodiments, a TIGIT-binding agent binds both human TIGIT and mouse TIGIT with a $K_D$ of about 1 nM or less. In some embodiments, a TIGIT-binding agent binds both human TIGIT and mouse TIGIT with a $K_D$ of about 0.1 nM or less. In some embodiments, the dissociation constant of the binding agent (e.g., an antibody) to TIGIT is the dissociation constant determined using a TIGIT fusion protein comprising at least a portion of the extracellular domain of TIGIT protein immobilized on a BiaCore® chip. In some embodiments, the dissociation constant of the binding agent (e.g., an antibody) to TIGIT is the dissociation constant determined using the binding agent captured by an anti-human IgG antibody on a BiaCore® chip and a soluble TIGIT protein.

In some embodiments, a TIGIT-binding agent comprises a first antigen-binding site that specifically binds TIGIT and a second antigen-binding site that specifically binds a second target. In some embodiments, a TIGIT-binding agent is a bispecific agent that comprises a first antigen-binding site that specifically binds TIGIT and a second antigen-binding site that specifically binds a second target. In some embodiments, a TIGIT-binding agent binds both TIGIT and the second target with a $K_D$ of about 100 nM or less. In some embodiments, a TIGIT-binding agent binds both TIGIT and the second target with a $K_D$ of about 50 nM or less. In some embodiments, a TIGIT-binding agent binds both TIGIT and the second target with a $K_D$ of about 20 nM or less. In some embodiments, a TIGIT-binding agent binds both TIGIT and the second target with a $K_D$ of about 10 nM or less. In some embodiments, a TIGIT-binding agent binds both TIGIT and the second target with a $K_D$ of about 1 nM or less. In some embodiments, the affinity of one of the antigen-binding sites may be weaker than the affinity of the other antigen-binding site. For example, the $K_D$ of one antigen binding site may be about 1 nM and the $K_D$ of the second antigen-binding site may be about 10 nM. In some embodiments, the difference in affinity between the two antigen-binding sites may be about 2-fold or more, about 3-fold or more, about 5-fold or more, about 8-fold or more, about 10-fold or more, about 15-fold or more, about 20-fold or more, about 30-fold or more, about 50-fold or more, or about 100-fold or more. Modulation of the affinities of the two antigen-binding sites may affect the biological activity of the bispecific antibody. For example, decreasing the affinity of the antigen-binding site for TIGIT or the second target, may have a desirable effect, for example decreased toxicity of the binding agent and/or increased therapeutic index.

In certain embodiments, the TIGIT-binding agent (e.g., an antibody) binds TIGIT with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a TIGIT-binding agent binds to human TIGIT with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, a TIGIT-binding agent binds mouse TIGIT and/or human TIGIT with an $EC_{50}$ of about 40 nM or less, about 20 nM or less, about 10 nM or less, about 1 nM or less or about 0.1 nM or less.

In certain embodiments, the TIGIT-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In certain embodiments, the antibody is an IgG1 antibody. In certain embodiments, the antibody is an IgG2 antibody. In some embodiments, the antibody is an IgG4 antibody. In certain embodiments, the antibody is an antibody fragment comprising an antigen-binding site. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some embodiments, the antibody is conjugated to a cytotoxic moiety. In some embodiments, the antibody is isolated. In some embodiments, the antibody is substantially pure.

In some embodiments, the TIGIT-binding agents are polyclonal antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, full-length recombinant protein, or fusion protein) using multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, a TIGIT-binding agent is a monoclonal antibody. Monoclonal antibodies can be prepared using hybridoma methods known to one of skill in the art. In some embodiments, using the hybridoma method, a mouse, rat, rabbit, hamster, or other appropriate host animal, is immunized as described above to elicit the production of antibodies that specifically bind the immunizing antigen. In some embodiments, lymphocytes can be immunized in vitro. In some embodiments, the immunizing antigen can be a human protein or a fragment thereof. In some embodiments, the immunizing antigen can be a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species.

The polynucleotide(s) encoding a monoclonal antibody can be modified, for example, by using recombinant DNA technology to generate alternative antibodies. In some embodiments, the constant domains of the light chain and heavy chain of, for example, a mouse monoclonal antibody can be substituted for constant regions of, for example, a human antibody to generate a chimeric antibody, or for a non-immunoglobulin polypeptide to generate a fusion antibody. In some embodiments, the constant regions are truncated or removed to generate a desired antibody fragment of a monoclonal antibody. Site-directed or high-density mutagenesis of the variable region(s) can be used to optimize specificity, affinity, etc. of a monoclonal antibody.

In some embodiments, a TIGIT-binding agent is a humanized antibody. Typically, humanized antibodies are human immunoglobulins in which the amino acid residues of the CDRs are replaced by amino acid residues from CDRs of a non-human species (e.g., mouse, rat, rabbit, hamster, etc.) that have the desired specificity, affinity, and/or binding capability using methods known to one skilled in the art. In some embodiments, some of the framework variable region amino acid residues of a human immunoglobulin are replaced with corresponding amino acid residues in an antibody from a non-human species. In some embodiments, a humanized antibody can be further modified by the substitution of additional residues either in the framework variable region and/or within the replaced non-human residues to further refine and optimize antibody specificity, affinity, and/or capability. In general, a humanized antibody will comprise variable domain regions containing all, or substantially all, of the CDRs that correspond to the non-human immunoglobulin whereas all, or substantially all, of the framework regions are those of a human immunoglobulin sequence. In some embodiments, the framework regions are those of a human consensus immunoglobulin sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject.

In certain embodiments, a TIGIT-binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated. In some embodiments, the human antibody can be selected from a phage library, where that phage library expresses human antibodies. Alternatively, phage display technology can be used to produce human antibodies and antibody fragments in vitro, from immunoglobulin variable domain gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production.

In some embodiments, the TIGIT-binding agent is a bispecific antibody. Thus, this invention encompasses bispecific antibodies that specifically recognize TIGIT and at least one additional target. Bispecific antibodies are capable of specifically recognizing and binding at least two different antigens or epitopes. The different epitopes can either be within the same molecule (e.g., two epitopes on TIGIT) or on different molecules (e.g., one epitope on TIGIT and one epitope on a different protein). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., a tumor and/or tumor microenvironment). In some embodiments, a bispecific antibody has the ability to concentrate the actions of two agents to a common target (e.g., a tumor or a tumor cell). In some embodiments, a bispecific antibody has the ability to target the actions of two agents to more than one biological pathway or function. In some embodiments, a bispecific antibody has the ability to target two different cells and bring them closer together (e.g., an immune cell and a tumor cell).

In some embodiments, the bispecific antibody is a monoclonal antibody. In some embodiments, the bispecific antibody is a humanized antibody. In some embodiments, the bispecific antibody is a human antibody. In some embodiments, the bispecific antibody is an IgG1 antibody. In some embodiments, the bispecific antibody is an IgG2 antibody. In some embodiments, the bispecific antibody is an IgG4 antibody. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, the antibodies can specifically recognize and bind TIGIT as well as a second antigen target, such as an effector molecule on an immune cell (e.g., CD2, CD3, CD28, CTLA4, PD-1, PD-L1, CD80, or CD86) or a Fc receptor (e.g., CD64, CD32, or CD16). In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy. In some cases, the "knobs" and "holes" terminology is replaced with the terms "protuberances" and "cavities". In some embodiments, the bispecific antibodies may comprise variant hinge regions incapable of forming disulfide linkages between the heavy chains. In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. For example, trispecific antibodies can be prepared. Thus, in certain embodiments the antibodies to TIGIT are multispecific.

In certain embodiments, the antibodies (or other polypeptides) described herein may be monospecific. In certain embodiments, each of the one or more antigen-binding sites that an antibody contains is capable of binding (or binds) a homologous epitope on TIGIT.

In certain embodiments, a TIGIT-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced by recombinant methods. In some embodiments, antibody fragments include Fv or single chain Fv (scFv) fragments. Fab, Fv, and scFv antibody fragments can be expressed in and secreted from $E.$ $coli$ or other host cells, allowing for the production of large amounts of these fragments. In some embodiments, antibody fragments are isolated from antibody phage libraries as discussed herein. For example, methods can be used for the construction of Fab expression libraries to allow rapid and effective identification of monoclonal Fab fragments with the desired specificity for TIGIT or derivatives, fragments, analogs or homologs thereof. In some embodiments, antibody fragments are linear antibody fragments. In certain embodiments, antibody fragments are monospecific or bispecific. In certain embodiments, the TIGIT-binding agent is a scFv. Various techniques can be used for the production of single-chain antibodies specific to TIGIT.

In some embodiments, especially in the case of antibody fragments, an antibody is modified in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells. It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., TIGIT). In this regard, the variable region may comprise or be derived from any type of mammal that can be induced to mount a humoral response and generate immunoglobulins against the desired antigen. As such, the variable region of the modified antibodies can be, for example, of human, murine, rat, rabbit, non-human primate (e.g. cynomolgus monkeys, macaques, etc.), or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding. In some embodiments, the mutation of a single amino acid in selected areas of the CH2 domain may be enough to substantially reduce Fc binding and increase cancer cell localization and/or tumor penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody. In some embodiments, the deletion or inactivation (through point mutations or other means) of a constant region domain may reduce Fc receptor binding of the circulating modified antibody thereby increasing cancer cell localization and/or tumor penetration. In other embodiments, the constant region modifications increase the serum half-life of the antibody. In other embodiments, the constant region modifications reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques.

In certain embodiments, a TIGIT-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor and/or complement factors. In certain embodiments, the antibody has no effector function(s).

The present invention further embraces variants and equivalents which are substantially homologous to the recombinant, monoclonal, chimeric, humanized, and human antibodies, or antibody fragments thereof, described herein. These variants can contain, for example, conservative substitution mutations, i.e. the substitution of one or more amino acids by similar amino acids.

In certain embodiments, the antibodies described herein are isolated. In certain embodiments, the antibodies described herein are substantially pure.

The TIGIT-binding agents (e.g., antibodies) of the present invention can be assayed for specific binding by any method known in the art. The immunoassays which can be used include, but are not limited to, competitive and non-competitive assay systems using techniques such as BiaCore® analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well-known in the art (see, e.g., Ausubel et al., Editors, 1994-present, *Current Protocols in Molecular Biology*, John Wiley & Sons, Inc., New York, N.Y.).

In a non-limiting example, screening for specific binding of an antibody to human TIGIT may be determined using ELISA. An ELISA comprises preparing antigen (e.g., TIGIT or a fragment thereof), coating wells of a 96-well microtiter plate with antigen, adding the test antibodies conjugated to a detectable compound such as an enzymatic substrate (e.g. horseradish peroxidase or alkaline phosphatase) to the well, incubating for a period of time, and detecting the presence of an antibody bound to the antigen. In some embodiments, the test antibodies are not conjugated to a detectable compound, but instead a secondary antibody that recognizes the antibody (e.g., an anti-Fc antibody) and is conjugated to a detectable compound is added to the wells. In some embodiments, instead of coating the well with the antigen, the test antibodies can be coated to the wells, the antigen (e.g., TIGIT) is added to the wells, followed by a secondary antibody conjugated to a detectable compound. One of skill in the art would be knowledgeable as to the parameters that can be modified to increase the signal detected as well as other variations of ELISAs known in the art.

In another non-limiting example, the specific binding of an antibody to TIGIT may be determined using FACS. A FACS screening assay may comprise generating a cDNA construct that expresses an antigen as a full-length protein (TIGIT) or a fusion protein (e.g., TIGIT-CD4TM), transfecting the construct into cells, expressing the antigen on the surface of the cells, mixing the test antibodies with the transfected cells, and incubating for a period of time. The cells bound by the test antibodies may be identified using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding agent to an antigen (e.g., TIGIT) and the off-rate of an antibody-antigen interaction can be determined by competitive binding assays. One example of a competitive binding assay is a radioimmunoassay comprising the incubation of labeled antigen (e.g., $^3$H or $^{125}$I-TIGIT), or fragment or variant thereof, with the antibody of interest in the presence of increasing amounts of unlabeled antigen followed by the detection of the antibody bound to the labeled antigen. The affinity of the antibody for the antigen and the binding off-rates can be determined from the data by Scatchard plot analysis. In some embodiments, BiaCore® kinetic analysis is used to determine the binding on and off rates of antibodies or agents that bind an antigen (e.g., TIGIT). In some embodiments, BiaCore® kinetic analysis comprises analyzing the binding and dissociation of antibodies from chips with immobilized antigen (e.g., TIGIT) on their surface. In some embodiments, BiaCore® kinetic analysis comprises analyzing the binding and dissociation of antigen (e.g., TIGIT) from chips with immobilized antibody (e.g., anti-TIGIT antibody) on their surface.

In certain embodiments of the methods described herein, the invention provides a TIGIT-binding agent (e.g., an antibody) that specifically binds human TIGIT, wherein the TIGIT-binding agent comprises one, two, three, four, five, and/or six of the CDRs of antibody OMP-313M32 (see Table 1). Anti-TIGIT antibody OMP-313M32 In some embodiments, the TIGIT-binding agent comprises one or more of the CDRs of OMP-313M32; two or more of the CDRs of OMP-313M32; three or more of the CDRs of OMP-313M32; four or more of the CDRs of OMP-313M32; five or more of the CDRs of OMP-313M32; or all six of the CDRs of OMP-313M32.

TABLE 1

| | OMP-313M32 |
|---|---|
| HC CDR1 | TSDYAWN (SEQ ID NO: 4) |
| HC CDR2 | YISYSGSTSYNPSLRS (SEQ ID NO: 5) |
| HC CDR3 | ARRQVGLGFAY (SEQ ID NO: 6) |
| LC CDR1 | KASQDVSTAVA (SEQ ID NO: 7) |
| LC CDR2 | SASYRYT (SEQ ID NO: 8) |
| LC CDR3 | QQHYSTP (SEQ ID NO: 9) |

In certain embodiments of the methods described herein, the invention provides a TIGIT-binding agent (e.g., an antibody) that specifically binds human TIGIT, wherein the TIGIT-binding agent comprises a heavy chain CDR1 comprising TSDYAWN (SEQ ID NO:4), a heavy chain CDR2 comprising YISYSGSTSYNPSLRS (SEQ ID NO:5), and a heavy chain CDR3 comprising ARRQVGLGFAY (SEQ ID NO:6). In some embodiments, the TIGIT-binding agent further comprises a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the TIGIT-binding agent comprises a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the TIGIT-binding agent comprises: (a) a heavy chain CDR1 comprising TSDYAWN (SEQ ID NO:4), a heavy chain CDR2 comprising YISYSGSTSYNPSLRS (SEQ ID NO:5), and a heavy chain CDR3 comprising ARRQVGLGFAY (SEQ ID NO:6); and (b) a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In certain embodiments of the methods described herein, the invention provides a TIGIT-binding agent (e.g., an antibody) that specifically binds human TIGIT, wherein the TIGIT-binding agent comprises: (a) a heavy chain CDR1 comprising TSDYAWN (SEQ ID NO:4) or a variant thereof comprising 1, 2, 3, or 4 amino acid substitutions; (b) a heavy chain CDR2 comprising YISYSGSTSYNPSLRS (SEQ ID NO:5) or a variant thereof comprising 1, 2, 3, or 4 amino acid substitutions; (c) a heavy chain CDR3 comprising ARRQVGLGFAY (SEQ ID NO:6) or a variant thereof comprising 1, 2, 3, or 4 amino acid substitutions; (d) a light chain CDR1 comprising KASQDVSTAVA (SEQ ID NO:7) or a variant thereof comprising 1, 2, 3, or 4 amino acid substitutions; (e) a light chain CDR2 comprising SASYRYT (SEQ ID NO:8) or a variant thereof comprising 1, 2, 3, or 4 amino acid substitutions; and (f) a light chain CDR3 comprising QQHYSTP (SEQ ID NO:9) or a variant thereof comprising 1, 2, 3, or 4 amino acid substitutions. In certain embodiments, the amino acid substitutions are conservative substitutions. In some embodiments, the substitutions are made as part of a humanization process. In some embodiments, the substitutions are made as part of a germline humanization process. In some embodiments, the substitutions are made as part of a binding optimization process.

In certain embodiments of the methods described herein, the invention provides a TIGIT-binding agent (e.g., an antibody) that specifically binds human TIGIT, wherein the TIGIT-binding agent comprises a heavy chain variable region having at least about 80% sequence identity to SEQ ID NO:10 and/or a light chain variable region having at least 80% sequence identity to SEQ ID NO:11. In certain embodiments, the TIGIT-binding agent comprises a heavy chain variable region having at least about 85%, at least about 90%, at least about 95%, at least about 97%, or at least about 99% sequence identity to SEQ ID NO:10. In certain embodiments, the TIGIT-binding agent comprises a light chain variable region having at least about 85%, at least about 90%, at least about 95%, at least about 97%, or at least about 99% sequence identity to SEQ ID NO:11. In certain embodiments, the TIGIT-binding agent comprises a heavy chain variable region having at least about 95% sequence identity to SEQ ID NO:10 and/or a light chain variable region having at least about 95% sequence identity to SEQ ID NO:11. In certain embodiments, the TIGIT-binding agent comprises a heavy chain variable region comprising SEQ ID NO:10 and/or a light chain variable region comprising SEQ ID NO:11. In certain embodiments, the TIGIT-binding agent comprises a heavy chain variable region comprising SEQ ID NO:10 and a light chain variable region comprising SEQ ID NO:11. In certain embodiments, the TIGIT-binding agent comprises a heavy chain variable region consisting essentially of SEQ ID NO:10 and a light chain variable region consisting essentially of SEQ ID NO:11. In certain embodiments, the TIGIT-binding agent comprises a heavy chain variable region consisting of SEQ ID NO:10 and a light chain variable region consisting of SEQ ID NO:11.

In certain embodiments of the methods described herein, the TIGIT-binding agent comprises a heavy chain variable region comprising SEQ ID NO:10 and a light chain variable region comprising SEQ ID NO:11. In certain embodiments, the TIGIT-binding agent comprises a heavy chain variable region consisting essentially of SEQ ID NO:10 and a light chain variable region consisting essentially of SEQ ID NO:11. In certain embodiments, the TIGIT-binding agent comprises a heavy chain variable region consisting of SEQ ID NO:10 and a light chain variable region consisting of SEQ ID NO:11.

In certain embodiments of the methods described herein, the invention provides a TIGIT-binding agent (e.g., an antibody) that specifically binds human TIGIT, wherein the TIGIT-binding agent comprises: a heavy chain having at least 90% sequence identity to SEQ ID NO:13 and/or a light chain having at least 90% sequence identity to SEQ ID NO:15. In some embodiments, the TIGIT-binding agent comprises: a heavy chain having at least 95% sequence identity to SEQ ID NO:13 and/or a light chain having at least 95% sequence identity to SEQ ID NO:15. In some embodiments, the TIGIT-binding agent comprises a heavy chain comprising SEQ ID NO:13 and/or a light chain comprising SEQ ID NO:15. In some embodiments, the TIGIT-binding agent comprises a heavy chain consisting essentially of SEQ ID NO:13 and a light chain consisting essentially of SEQ ID NO:15. In some embodiments, the TIGIT-binding agent comprises a heavy chain consisting of SEQ ID NO:13 and a light chain consisting of SEQ ID NO:15.

In certain embodiments of the methods described herein, the invention provides a TIGIT-binding agent (e.g., an antibody) that specifically binds human TIGIT, wherein the TIGIT-binding agent comprises: a heavy chain having at least 90% sequence identity to SEQ ID NO:17 and/or a light chain having at least 90% sequence identity to SEQ ID NO:15. In some embodiments, the TIGIT-binding agent comprises: a heavy chain having at least 95% sequence identity to SEQ ID NO:17 and/or a light chain having at least 95% sequence identity to SEQ ID NO:15. In some embodiments, the TIGIT-binding agent comprises a heavy chain comprising SEQ ID NO:17 and/or a light chain comprising SEQ ID NO:15. In some embodiments, the TIGIT-binding agent comprises a heavy chain consisting essentially of SEQ ID NO:17 and a light chain consisting essentially of SEQ ID NO:15. In some embodiments, the TIGIT-binding agent comprises a heavy chain consisting of SEQ ID NO:17 and a light chain consisting of SEQ ID NO:15.

In certain embodiments of the methods described herein, a TIGIT-binding agent comprises the heavy chain variable region and light chain variable region of the OMP-313M32 antibody. In some embodiments, the TIGIT-binding agent comprises the variable regions of the OMP-313M32 antibody wherein the heavy chain variable region and/or the light chain variable region from the OMP-313M32 antibody have been affinity-matured. In certain embodiments, a TIGIT-binding agent comprises the heavy chain and light chain of the OMP-313M32 antibody (with or without the leader sequence). In certain embodiments, a TIGIT-binding agent is the OMP-313M32 antibody. In certain embodiments, a TIGIT-binding agent comprises the heavy chain variable region of the OMP-313M32 antibody as part of an IgG1, IgG2, or IgG4 heavy chain. In certain embodiments, a TIGIT-binding agent comprises the heavy chain variable region of the OMP-313M32 antibody as part of a human IgG1 heavy chain. In certain embodiments, a TIGIT-binding agent comprises the heavy chain variable region of the OMP-313M32 antibody as part of a human IgG2 heavy chain. In certain embodiments, a TIGIT-binding agent comprises the heavy chain variable region of the OMP-313M32 antibody as part of a human IgG4 heavy chain. In certain embodiments, a TIGIT-binding agent which comprises the heavy chain variable region of the OMP-313M32 antibody as part of a human IgG4 heavy chain is referred to as the OMP-313M33 antibody.

In certain embodiments of the methods described herein, a TIGIT-binding agent comprises, consists essentially of, or consists of, the antibody OMP-313M32. In certain embodiments, a TIGIT-binding agent comprises, consists essentially of, or consists of, a variant of the antibody OMP-313M32. In certain embodiments, a TIGIT-binding agent comprises, consists essentially of, or consists of, the antibody OMP-313M33.

In some embodiments of the methods described herein, the TIGIT-binding agent comprises a heavy chain variable region encoded by the plasmid deposited with American Type Culture Collection (ATCC), 10801 University Boulevard, Manassas, Va., USA, under the conditions of the Budapest Treaty on Aug. 11, 2015, and designated PTA-122346. In some embodiments, the TIGIT-binding agent comprises a light chain variable region encoded by the plasmid deposited with ATCC, 10801 University Boulevard, Manassas, Va., USA, under the conditions of the Budapest Treaty on Aug. 11, 2015, and designated PTA-122347. In some embodiments, the TIGIT-binding agent comprises a heavy chain variable region encoded by the plasmid deposited with ATCC and designated PTA-122346 and a light chain variable region encoded by the plasmid deposited with ATCC and designated PTA-122347. In some embodiments, the TIGIT-binding agent comprises a heavy chain comprising a variable region encoded by the plasmid deposited with ATCC and designated PTA-122346. In some embodiments, the TIGIT-binding agent comprises a light chain encoded by the plasmid deposited with ATCC and designated PTA-122347. In some embodiments, the TIGIT-binding agent comprises a heavy chain comprising a variable region encoded by the plasmid deposited with ATCC and designated PTA-122346 and a light chain encoded by the plasmid deposited with ATCC and designated PTA-122347.

In some embodiments of the methods described herein, the TIGIT-binding agents are homodimeric agents/molecules and heterodimeric agents/molecules. In some embodiments, the homodimeric agents are polypeptides. In some embodiments, the heterodimeric molecules are polypeptides. Generally the homodimeric molecule comprises two identical polypeptides. Generally the heterodimeric molecule comprises at least two different polypeptides. In some embodiments, the heterodimeric molecule is capable of binding at least two targets, e.g., a bispecific agent. The targets may be, for example, two different proteins on a single cell or two different proteins on two separate cells. The term "arm" may be used herein to describe the structure of a homodimeric agent, a heterodimeric agent, and/or a bispecific agent. In some embodiments, each arm comprises at least one polypeptide. Generally, each arm of a heterodimeric molecule has a different function, for example, binding two different targets. In some embodiments, one arm may comprise an antigen-binding site from an antibody. In some embodiments, one arm may comprise a binding portion of a receptor. In some embodiments, one arm may comprise a ligand. In some embodiments, one arm may comprise a binding region of a ligand. In some embodiments, a homodimeric agent comprises two identical arms. In some embodiments, a heterodimeric agent comprises two different arms. In some embodiments, a bispecific agent comprises two different arms.

In some embodiments of the methods described herein, the invention provides a TIGIT-binding agent that is a homodimeric molecule. In some embodiments, the homodimeric molecule comprises two identical polypeptides. In some embodiments, the invention provides a TIGIT-binding agent that is a heterodimeric molecule. In some embodiments, the heterodimeric molecule comprises at least two different polypeptides. In some embodiments, the invention provides a TIGIT-binding agent that is a heterodimeric agent. In some embodiments, the invention provides a TIGIT-binding agent that is a bispecific agent. In certain embodiments, the TIGIT-binding agent is a bispecific antibody.

In some of the embodiments of the methods described herein the invention provides polypeptides, including, but not limited to, antibodies that specifically bind TIGIT. In some embodiments, a polypeptide binds human TIGIT. In some embodiments, a polypeptide binds mouse TIGIT. In some embodiments, a polypeptide binds mouse TIGIT and human TIGIT. In some embodiments, a polypeptide binds human TIGIT and does not bind mouse TIGIT. In some embodiments, a polypeptide binds human TIGIT and does not bind rat TIGIT. In some embodiments, a polypeptide binds human TIGIT and does not bind rabbit TIGIT. In some embodiments, a polypeptide binds human TIGIT and does not bind marmoset TIGIT. In some embodiments, a polypeptide binds human TIGIT and does not bind dog TIGIT. In some embodiments, a polypeptide binds human TIGIT and does not bind pig TIGIT. In some embodiments, a polypeptide binds human TIGIT and does not bind cynomolgus monkey TIGIT. In some embodiments, a polypeptide binds human TIGIT and does not bind rhesus monkey TIGIT.

In certain embodiments of the methods described herein, a polypeptide comprises one, two, three, four, five, and/or six of the CDRs of antibody OMP-313M32 (see Table 1 herein). In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments of the methods described herein, the invention provides a polypeptide that specifically binds human TIGIT, wherein the polypeptide comprises an amino acid sequence having at least about 80% sequence identity to SEQ ID NO:10, and/or an amino acid sequence having at least about 80% sequence identity to SEQ ID NO:11. In certain embodiments, the polypeptide comprises an amino acid sequence having at least about 85%, at least about 90%, at least about 95%, at least about 97%, or at least about 99% sequence identity to SEQ ID NO:10. In certain embodiments, the polypeptide comprises an amino acid sequence having at least about 85%, at least about 90%, at least about 95%, at least about 97%, or at least about 99% sequence identity to SEQ ID NO:64 or SEQ ID NO:11. In certain embodiments, the polypeptide comprises an amino acid sequence having at least about 95% sequence identity to SEQ ID NO:10 and/or an amino acid sequence having at least about 95% sequence identity to SEQ ID NO:11. In certain embodiments, the polypeptide comprises an amino acid sequence comprising SEQ ID NO:10 and/or an amino acid sequence comprising SEQ ID NO:11.

In some embodiments of the methods described herein, a polypeptide comprises one or more amino acid sequences selected from the group consisting of: SEQ ID NO:10, SEQ ID NO:11, SEQ ID NO:12, SEQ ID NO:13, SEQ ID NO:14, SEQ ID NO:15, SEQ ID NO:16, and SEQ ID NO:17. As defined herein, a polypeptide can occur as a single chain or as two or more associated chains. In certain embodiments, a polypeptide comprises an amino acid sequence comprising SEQ ID NO:10 and an amino acid sequence comprising SEQ ID NO:11. In certain embodiments, a polypeptide comprises an amino acid sequence comprising SEQ ID NO:12 and an amino acid sequence comprising SEQ ID NO:14. In certain embodiments, the polypeptide comprises an amino acid sequence comprising SEQ ID NO:13 and an amino acid sequence comprising SEQ ID NO:15. In certain embodiments, the polypeptide comprises an amino acid sequence comprising SEQ ID NO:16 and an amino acid sequence comprising SEQ ID NO:14. In certain embodiments, the polypeptide comprises an amino acid sequence comprising SEQ ID NO:17 and an amino acid sequence comprising SEQ ID NO:15.

In certain embodiments of the methods described herein, a polypeptide comprises an amino acid sequence consisting of SEQ ID NO:10 and an amino acid sequence consisting of SEQ ID NO:11. In certain embodiments, a polypeptide comprises an amino acid sequence consisting of SEQ ID NO:12 and an amino acid sequence consisting of SEQ ID NO:14. In certain embodiments, a polypeptide comprises an amino acid sequence consisting of SEQ ID NO:13 and an amino acid sequence consisting of SEQ ID NO:15. In certain embodiments, a polypeptide comprises an amino acid sequence consisting of SEQ ID NO:16 and an amino acid sequence consisting of SEQ ID NO:14. In certain embodiments, a polypeptide comprises an amino acid sequence consisting of SEQ ID NO:17 and an amino acid sequence consisting of SEQ ID NO:15.

Many proteins, including antibodies, contain a signal sequence that directs the transport of the proteins to various locations. Generally, signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or may be used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to a "native" or "parental" signal sequence. In some embodiments, the signal sequence of the polypeptide comprises amino acid substitutions and/or deletions that allow one cleavage site to be dominant, thereby resulting in a substantially homogeneous polypeptide with one N-terminus. In some embodiments, a signal sequence of the polypeptide affects the expression level of the polypeptide, e.g., increased expression or decreased expression.

In certain embodiments of the methods described herein, an antibody or other binding agent competes for specific binding to human TIGIT with a TIGIT-binding agent described herein. In some embodiments, an antibody or other binding agent competes for specific binding to TIGIT with a TIGIT-binding agent comprising: (a) a heavy chain CDR1 comprising TSDYAWN (SEQ ID NO:4), a heavy chain CDR2 comprising YISYSGSTSYNPSLRS (SEQ ID NO:5), and a heavy chain CDR3 comprising ARRQVGLGFAY (SEQ ID NO:6) and (b) a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In certain embodiments of the methods described herein, an antibody or other binding agent competes for specific binding to human TIGIT with a TIGIT-binding agent comprising a heavy chain variable region comprising SEQ ID NO:10 and a light chain variable region comprising SEQ ID NO:11. In certain embodiments, an antibody or other binding agent competes for specific binding to human TIGIT with a TIGIT-binding agent comprising a heavy chain comprising SEQ ID NO:13 and a light chain comprising SEQ ID NO:15. In certain embodiments, an antibody or other binding agent competes for specific binding to human TIGIT with a TIGIT-binding agent comprising a heavy chain comprising SEQ ID NO:17 and a light chain comprising SEQ ID NO:15.

In certain embodiments of the methods described herein, an antibody or other binding agent competes with antibody OMP-313M32 for specific binding to human TIGIT. In some embodiments, an antibody or other binding agent competes with a reference antibody for specific binding to human TIGIT, wherein the reference antibody is antibody OMP-313M32. In some embodiments, an antibody or other binding agent competes with a reference antibody for specific binding to human TIGIT, wherein the reference antibody is antibody 313M33.

In certain embodiments of the methods described herein, an antibody or other binding agent binds the same epitope, or essentially the same epitope, on TIGIT as a TIGIT-binding agent described herein. In certain embodiments, an antibody or other binding agent binds the same epitope, or essentially the same epitope, on human TIGIT as antibody OMP-313M32. In certain embodiments, an antibody or other binding agent binds the same epitope, or essentially the same epitope, on human TIGIT as antibody 313M33.

In another embodiment of the methods described herein, an antibody or other binding agent binds an epitope on TIGIT that overlaps with the epitope on TIGIT bound by a TIGIT-binding agent described herein. In another embodiment, the antibody or other binding agent binds an epitope on TIGIT that overlaps with the epitope on human TIGIT bound by antibody OMP-313M32. In another embodiment, the antibody or other binding agent binds an epitope on TIGIT that overlaps with the epitope on human TIGIT bound by antibody 313M33.

In some embodiments of the methods described herein, an antibody or other binding agent competes for binding to an epitope comprising amino acids within SEQ ID NO:27 with a TIGIT-binding agent described herein. In some embodiments, an antibody or other binding agent competes for binding to an epitope comprising amino acids within SEQ ID NO:28 with a TIGIT-binding agent described herein. In some embodiments, an antibody or other binding agent competes for binding to an epitope comprising amino acids within SEQ ID NO:27 and SEQ ID NO:28 with a TIGIT-binding agent described herein. In some embodiments, an antibody or other binding agent competes for binding to an epitope comprising amino acids Q62 and I109 of SEQ ID NO:1 with a TIGIT-binding agent described herein. In some embodiments, an antibody or other binding agent competes for binding to an epitope comprising amino acids Q62 and T119 of SEQ ID NO:1 with a TIGIT-binding agent described herein. In some embodiments, an antibody or other binding agent competes for binding with an epitope comprising amino acids Q64 and I109 of SEQ ID NO:1 with a TIGIT-binding agent described herein. In some embodiments, an antibody or other binding agent competes for binding to an epitope comprising amino acids Q64 and T119 of SEQ ID NO:1 with a TIGIT-binding agent described herein. In some embodiments, an antibody or other binding agent competes for binding to an epitope comprising amino acids Q62, Q64, and I109 of SEQ ID NO:1 with a TIGIT-binding agent described herein. In some embodiments, an antibody or other binding agent competes for binding to an epitope comprising amino acids Q62, Q64, and T119 of SEQ ID NO:1 with a TIGIT-binding agent described herein. In some embodiments, an antibody or other binding agent competes for binding to an epitope comprising amino acids Q62, I109, and T119 of SEQ ID NO:1 with a TIGIT-binding agent described herein. In some embodiments, an antibody or other binding agent competes for binding to an epitope comprising amino acids Q64, I109, and T119 of SEQ ID NO:1 with a TIGIT-binding agent described herein. In some embodiments, an antibody or other binding agent competes for binding to an epitope comprising amino acids Q62, Q64, I109, and T119 of SEQ ID NO:1 with a TIGIT-binding agent described herein. In some embodiments, an antibody or other binding agent competes for binding to an epitope comprising at least one amino acid selected from the group consisting of: N58, E60, Q62, Q64, L65, F107, I109, H111, T117, T119, G120, and R121 of SEQ ID NO:1 with a TIGIT-binding agent described herein.

In certain embodiments of the methods described herein, the TIGIT-binding agent (e.g., an antibody) binds TIGIT and modulates TIGIT activity. In some embodiments, the TIGIT-binding agent is a TIGIT antagonist and decreases TIGIT activity. In certain embodiments, the TIGIT-binding agent inhibits TIGIT activity by at least about 10%, at least about 20%, at least about 30%, at least about 50%, at least about 75%, at least about 90%, or about 100%. In certain embodiments, a TIGIT-binding agent that inhibits TIGIT activity is antibody OMP-313M32. In certain embodiments, a TIGIT-binding agent that inhibits TIGIT activity is antibody OMP-313M32. In certain embodiments, a TIGIT-binding agent that inhibits TIGIT activity is antibody OMP-313M33.

In some embodiments of the methods described herein, the TIGIT-binding agent binds TIGIT and inhibits or reduces TIGIT signaling. In certain embodiments, the TIGIT-binding agent (e.g., an antibody) inhibits TIGIT signaling by at least about 10%, at least about 20%, at least about 30%, at least about 50%, at least about 75%, at least about 90%, or about 100%. In some embodiments, the TIGIT-binding agent inhibits mouse TIGIT signaling. In some embodiments, the TIGIT-binding agent inhibits human TIGIT signaling. In certain embodiments, a TIGIT-binding agent that inhibits TIGIT signaling is antibody OMP-313M32. In certain embodiments, a TIGIT-binding agent that inhibits TIGIT signaling is antibody OMP-313M33.

TIGIT is phosphorylated at its cytoplasmic tail after interaction with its counter-receptor PVR. The phosphorylation of TIGIT is the beginning of a cascade that includes downstream events affecting other known signaling pathways. Therefore, evaluating TIGIT phosphorylation can give information about TIGIT activity and TIGIT signaling.

Phosphorylation assays are known to those of skill in the art and are commonly used to monitor protein activation and/or pathway activation. The assays may be used to monitor the effect of various treatments on activation of a target protein and/or a target pathway. For example, an in vitro phosphorylation assay can be used to evaluate the effect of a TIGIT antagonist on the PVR-induced activation of TIGIT.

In certain embodiments of the methods described herein, the TIGIT-binding agent (e.g., antibody) inhibits binding of TIGIT to a receptor. In certain embodiments, the TIGIT-binding agent inhibits binding of TIGIT to PVR. In some embodiments, the TIGIT-binding agent inhibits binding of TIGIT to PVR-L2, PVR-L3, and/or PVR-L4. In certain embodiments, the inhibition of binding of a TIGIT-binding agent to PVR is at least about 10%, at least about 25%, at least about 50%, at least about 75%, at least about 90%, or at least about 95%. In certain embodiments, the inhibition of binding of a TIGIT-binding agent to PVR-L2, PVR-L3, and/or PVR-L4 is at least about 10%, at least about 25%, at least about 50%, at least about 75%, at least about 90%, or at least about 95%. In certain embodiments, a TIGIT-binding agent that inhibits binding of TIGIT to PVR is antibody OMP-313M32. In certain embodiments, a TIGIT-binding agent that inhibits binding of TIGIT to PVR is antibody OMP-313M33. In certain embodiments, a TIGIT-binding agent that inhibits binding of TIGIT to PVR-L2, PVR-L3, and/or PVR-L4 is antibody OMP-313M32. In certain embodiments, a TIGIT-binding agent that inhibits binding of TIGIT to PVR-L2, PVR-L3, and/or PVR-L4 is antibody OMP-313M33.

In certain embodiments of the methods described herein, the TIGIT-binding agent (e.g., antibody) blocks binding of TIGIT to a receptor. In certain embodiments, the TIGIT-binding agent blocks binding of TIGIT to PVR. In certain embodiments, the blocking of binding of a TIGIT-binding agent to PVR is at least about 10%, at least about 25%, at least about 50%, at least about 75%, at least about 90%, or at least about 95%. In some embodiments, the TIGIT-binding agent blocks binding of TIGIT to PVRL2, PVRL3, and/or PVRL4. In certain embodiments, the blocking of binding of a TIGIT-binding agent to PVRL2, PVRL3, and/or PVRL4 is at least about 10%, at least about 25%, at least about 50%, at least about 75%, at least about 90%, or at least about 95%. In certain embodiments, a TIGIT-binding agent that blocks binding of TIGIT to PVR is antibody OMP-313M32. In certain embodiments, a TIGIT-binding agent that blocks binding of TIGIT to PVR is antibody OMP-313M33. In certain embodiments, a TIGIT-binding agent that blocks binding of TIGIT to PVRL2, PVRL3, and/or PVRL4 is antibody OMP-313M32. In certain embodiments, a TIGIT-binding agent that blocks binding of TIGIT to PVRL2, PVRL3, and/or PVRL4 is antibody OMP-313M33.

Binding assays are known to those of skill in the art and are described herein. Binding assays may be used to monitor the effect of a test agent on the interaction between a target protein and the protein's binding partner (e.g., receptor or ligand). For example, an in vitro binding assay can be used to evaluate if a TIGIT antagonist blocks the interaction of TIGIT to PVR.

In certain embodiments, the TIGIT-binding agents described herein have one or more of the following effects: inhibit proliferation of tumor cells, inhibit tumor growth, reduce the tumorigenicity of a tumor, reduce the tumorigenicity of a tumor by reducing the frequency of cancer stem cells in the tumor, trigger cell death of tumor cells, enhance or boost the immune response, enhance or boost the anti-tumor response, increase cytolytic activity of immune cells, increase killing of tumor cells, increase killing of tumor cells by immune cells, induce cells in a tumor to differentiate, differentiate tumorigenic cells to a non-tumorigenic state, induce expression of differentiation markers in the tumor cells, prevent metastasis of tumor cells, decrease survival of tumor cells, increase cell contact-dependent growth inhibition, increase tumor cell apoptosis, reduce epithelial mesenchymal transition (EMT), or decrease survival of tumor cells. In some embodiments, the agents have one or more of the following effects: inhibit viral infection, inhibit chronic viral infection, reduce viral load, trigger cell death of virus-infected cells, or reduce the number or percentage of virus-infected cells.

In certain embodiments of the methods described herein, the TIGIT-binding agents inhibit tumor growth. In certain embodiments, the TIGIT-binding agents inhibit tumor growth in vivo (e.g., in a mouse model, and/or in a human having cancer). In certain embodiments, tumor growth is inhibited at least about two-fold, about three-fold, about five-fold, about ten-fold, about 50-fold, about 100-fold, or about 1000-fold as compared to a untreated tumor.

In certain embodiments of the methods described herein, the agents (e.g., polypeptides and/or antibodies) bind TIGIT and modulate an immune response. In some embodiments, a TIGIT-binding agent activates and/or increases an immune response. In some embodiments, a TIGIT-binding agent increases, promotes, or enhances cell-mediated immunity. In some embodiments, a TIGIT-binding agent increases, promotes, or enhances innate cell-mediated immunity. In some embodiments, a TIGIT-binding agent increases, promotes, or enhances adaptive cell-mediated immunity. In some embodiments, a TIGIT-binding agent increases, promotes, or enhances T-cell activity. In some embodiments, a TIGIT-binding agent increases, promotes, or enhances cytolytic T-cell (CTL) activity. In some embodiments, a TIGIT-binding agent increases, promotes, or enhances NK cell activity. In some embodiments, a TIGIT-binding agent increases, promotes, or enhances lymphokine-activated killer cell (LAK) activity. In some embodiments, a TIGIT-binding agent increases, promotes, or enhances tumor-infiltrating lymphocyte (TIL) activity. In some embodiments, a TIGIT-binding agent inhibits or decreases Treg cell activity. In some embodiments, a TIGIT-binding agent inhibits or decreases MDSC activity. In some embodiments, a TIGIT-binding agent increases, promotes, or enhances tumor cell killing. In some embodiments, a TIGIT-binding agent increases, promotes, or enhances the inhibition of tumor growth.

In certain embodiments of the methods described herein, a TIGIT-binding agent is an antagonist of human TIGIT. In some embodiments, the agent is an antagonist of TIGIT and activates and/or increases an immune response. In some embodiments, the agent is an antagonist of TIGIT and activates and/or increases activity of NK cells. In certain embodiments, the agent increases the activity by at least about 10%, at least about 20%, at least about 30%, at least about 50%, at least about 75%, at least about 90%, or about 100%. In some embodiments, the agent is an antagonist of TIGIT and activates and/or increases activity of T-cells (e.g., T-cell cytolytic activity). In certain embodiments, the agent increases the activity by at least about 10%, at least about 20%, at least about 30%, at least about 50%, at least about 75%, at least about 90%, or about 100%. In some embodiments, the agent is an antagonist of TIGIT and induces and/or enhances a Th1-type immune response. In general, a Th1-type immune response includes production of interferon-gamma (IFN-γ), IL-2, and tumor necrosis factor-beta (TNF-β). In comparison, a Th2-type immune response generally includes production of IL-4, IL-5, IL-6, IL-9, IL-10, and IL-13. In some embodiments, the agent is an antagonist of TIGIT and induces and/or increases cytokine or lymphokine production. In some embodiments, the induction and/or increase in cytokine or lymphokines production may be an indirect effect.

In certain embodiments of the methods described herein, a TIGIT-binding agent increases activation of NK cells. In certain embodiments, a TIGIT-binding agent increases activation of T-cells. In certain embodiments, the activation of NK cells and/or T-cells by a TIGIT-binding agent results in an increase in the level of activation of NK cells and/or T-cells of at least about 10%, at least about 25%, at least about 50%, at least about 75%, at least about 90%, or at least about 95%. In certain embodiments, a TIGIT-binding agent that increases activation of NK cells is antibody OMP-313M32. In certain embodiments, a TIGIT-binding agent that increases activation of NK cells is antibody OMP-313M33.

In certain embodiments of the methods described herein, the TIGIT-binding agent (e.g., antibody) is an antagonist of regulatory T-cell (Treg) activity. In certain embodiments, a TIGIT-binding agent inhibits or decreases the activity of Tregs. In certain embodiments, the inhibition of activity of Tregs by a TIGIT-binding agent results in an inhibition of suppressive activity of a Treg cell of at least about 10%, at least about 25%, at least about 50%, at least about 75%, at least about 90%, at least about 95%, or about 100%. In certain embodiments, a TIGIT-binding agent that inhibits Treg activity is antibody OMP-313M32. In certain embodiments, a TIGIT-binding agent that inhibits Treg activity is antibody OMP-313M33.

In certain embodiments of the methods described herein, the TIGIT-binding agent (e.g., antibody) is an antagonist of myeloid-derived suppressor cells (MDSCs). In certain embodiments, the TIGIT-binding agent inhibits MDSC activity. In certain embodiments, the TIGIT-binding agent inhibits MDSC activity by at least about 10%, at least about 20%, at least about 30%, at least about 50%, at least about 75%, at least about 90%, or about 100%. In certain embodiments, a TIGIT-binding agent that inhibits MDSC activity is antibody OMP-313M32. In certain embodiments, a TIGIT-binding agent that inhibits MDSC activity is antibody OMP-313M33.

In certain embodiments of the methods described herein, the TIGIT-binding agent (e.g., antibody) increases natural killer (NK) cell activity. In certain embodiments, the TIGIT-binding agent increases NK cell activity by at least about 10%, at least about 20%, at least about 30%, at least about 50%, at least about 75%, at least about 90%, or about 100%. In certain embodiments, a TIGIT-binding agent that increases NK cell activity is antibody OMP-313M32. In certain embodiments, a TIGIT-binding agent that increases NK cell activity is antibody OMP-313M33.

In certain embodiments of the methods described herein, the TIGIT-binding agent (e.g., antibody) increases tumor-infiltrating lymphocyte (TIL) activity. In certain embodiments, the TIGIT-binding agent increases TIL activity by at least about 10%, at least about 20%, at least about 30%, at least about 50%, at least about 75%, at least about 90%, or about 100%. In certain embodiments, a TIGIT-binding agent that increases TIL cell activity is antibody OMP-313M32. In certain embodiments, a TIGIT-binding agent that increases TIL cell activity is antibody OMP-313M33.

In certain embodiments of the methods described herein, the TIGIT-binding agent (e.g., antibody) increases or enhances lymphokines-activated killer cell (LAK) activity. In certain embodiments, the TIGIT-binding agent increases LAK activity by at least about 10%, at least about 20%, at least about 30%, at least about 50%, at least about 75%, at least about 90%, or about 100%. In certain embodiments, a TIGIT-binding agent that increases LAK cell activity is antibody OMP-313M32. In certain embodiments, a TIGIT-binding agent that increases LAK cell activity is antibody OMP-313M33.

In vivo and in vitro assays for determining whether a TIGIT-binding agent (or candidate binding agent) modulates an immune response are known in the art or are being developed. In some embodiments, a functional assay that detects T-cell activation may be used. In some embodiments, a functional assay that detects T-cell proliferation may be used. In some embodiments, a functional assay that detects NK activity may be used. In some embodiments, a functional assay that detects CTL activity may be used. In some embodiments, a functional assay that detects Treg activity may be used. In some embodiments, a functional assay that detects MDSC activity may be used. In some embodiments, a functional assay that detects production of cytokines or lymphokines or cells producing cytokines or lymphokines may be used. In some embodiments, an ELISpot™ assay is used to measure antigen-specific T-cell frequency. In some embodiments, an ELISpot™ assay is used to measure cytokine release/production and/or used to measure the number of cytokine producing cells. In some embodiments, cytokine assays are used to identify a Th1-type response. In some embodiments, cytokine assays are used to identify a Th2-type response. In some embodiments, cytokine assays are used to identify a Th17-type response. In some embodiments, FACS analysis is used to measure activation markers on immune cells, including but not limited to, T-cells, B-cells, NK cells, macrophages, and/or myeloid cells.

In certain embodiments of the methods described herein, the TIGIT-binding agents have a circulating half-life in mice, rats, cynomolgus monkeys, or humans of at least about 2 hours, at least about 5 hours, at least about 10 hours, at least about 24 hours, at least about 3 days, at least about 1 week, or at least about 2 weeks. In certain embodiments, the TIGIT-binding agent is an IgG (e.g., IgG1, IgG2, or IgG4) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0. Known methods of increasing the circulating half-life of antibody fragments lacking the Fc region include such techniques as PEGylation.

In some embodiments of the methods described herein, the TIGIT-binding agents are polypeptides. In some embodiments, the polypeptides are recombinant polypeptides, natural polypeptides, or synthetic polypeptides comprising an antibody, or fragment thereof, that bind TIGIT. It will be recognized in the art that some amino acid sequences of the invention can be varied without significant effect of the structure or function of the protein. Thus, the invention further includes variations of the polypeptides which show substantial activity or which include regions of an antibody, or fragment thereof, that binds TIGIT. In some embodiments, amino acid sequence variations of TIGIT-binding polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in *Remington: The Science and Practice of Pharmacy,* 22$^{st}$ Edition, 2012, Pharmaceutical Press, London.

In certain embodiments of the methods described herein, the TIGIT-binding agents are used in any one of a number of conjugated (i.e. an immunoconjugate or radioconjugate) or non-conjugated forms. In certain embodiments, the agents can be used in a non-conjugated form to harness the subject's natural defense mechanisms including complement-dependent cytotoxicity (CDC) and antibody dependent cellular cytotoxicity (ADCC) to eliminate malignant or cancer cells.

In some embodiments of the methods described herein, the TIGIT-binding agent is conjugated to a cytotoxic agent. In some embodiments, the TIGIT-binding agent is an antibody is conjugated to a cytotoxic agent as an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, daunorubicin, pyrrolobenzodiazepines (PBDs), or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{115}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as calicheamicins, maytansinoids, trichothenes, and CC1065, and the derivatives of these toxins that have toxin activity, can also be used. Conjugates of an antibody and cytotoxic agent may be made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

IV. Polynucleotides

The present invention provides polynucleotides comprising polynucleotides that encode a TIGIT-binding agent. The term "polynucleotides that encode a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide (e.g., a nucleotide sequence) encoding a polypeptide comprising an amino acid sequence selected from the group consisting of: SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

In certain embodiments, a polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding an amino acid sequence selected from the group consisting of: SEQ ID NO:10, SEQ ID NO:11, SEQ ID NO:12, SEQ ID NO:13, SEQ ID NO:14, SEQ ID NO:15, SEQ ID NO:16, and SEQ ID NO:17. Also provided is a polynucleotide that comprises a polynucleotide that hybridizes to a polynucleotide encoding an amino acid sequence selected from the group consisting of: SEQ ID NO:10, SEQ ID NO:11, SEQ ID NO:12, SEQ ID NO:13, SEQ ID NO:14, SEQ ID NO:15, SEQ ID NO:16, and SEQ ID NO:17. In certain embodiments, the hybridization is under conditions of high stringency. Conditions of high stringency are known to those of skill in the art and may include but are not limited to, (1) employ low ionic strength and high temperature for washing, for example 15 mM sodium chloride/1.5 mM sodium citrate (1×SSC) with 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes in 0.2×SSC containing 50% formamide at 55° C., followed by a high-stringency wash consisting of 0.1×SSC containing EDTA at 55° C.

In some embodiments, the polynucleotide comprises a polynucleotide sequence selected from the group consisting of: SEQ ID NO:18, SEQ ID NO:19, SEQ ID NO:20, SEQ ID NO:21, and SEQ ID NO:22. In certain embodiments, a polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a nucleotide sequence selected from the group consisting of: SEQ ID NO:18, SEQ ID NO:19, SEQ ID NO:20, SEQ ID NO:21, and SEQ ID NO:22. Also provided is a polynucleotide that comprises a polynucleotide that hybridizes to a polynucleotide sequence selected from the group consisting of: SEQ ID NO:18, SEQ ID NO:19, SEQ ID NO:20, SEQ ID NO:21, and SEQ ID NO:22. In certain embodiments, the hybridization techniques are conducted under conditions of high stringency as described above.

In certain embodiments, a polynucleotide comprises the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide. The polynucleotides can also encode for a pro-protein which is the mature protein plus additional 5' amino acid residues. A mature protein having a pro-sequence is a pro-protein and is an inactive form of the protein. Once the pro-sequence is cleaved an active mature protein remains.

In certain embodiments, a polynucleotide comprises the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:29) which can be used in conjunction with other affinity tags.

The present invention further relates to variants of the polynucleotides described herein, wherein the variant encodes, for example, fragments, analogs, and/or derivatives.

In certain embodiments, the present invention provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a TIGIT-binding agent.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heterodimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

V. Kits Comprising Agents Described Herein

The present invention provides kits that comprise the TIGIT-binding agents described herein and that can be used to perform the methods described herein. In certain embodiments, a kit comprises at least one purified TIGIT-binding agent in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed TIGIT-binding agents of the present invention can be readily incorporated into one of the established kit formats which are well known in the art.

Further provided are kits that comprise a TIGIT-binding agent as well as at least one additional therapeutic agent. In certain embodiments, the second (or more) therapeutic agent is a chemotherapeutic agent. In certain embodiments, the second (or more) therapeutic agent is an antibody.

VI. Additional Exemplary Embodiments

In some embodiments, the methods of inhibiting tumor growth in a subject provided throughout this application comprise administering to a subject a therapeutically effective amount of an antibody that specifically binds the extracellular domain of TIGIT, wherein the tumor is a solid tumor with high MSI, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments the tumor with high MSI is selected from the group consisting of CRC, gastric cancer, endometrium cancer, hepatobiliary tract cancer, urinary tract cancer, brain cancer and skin cancer. In some embodiments, the antibody that specifically binds the extracellular domain of TIGIT is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise administering to a subject a therapeutically effective amount of an antibody that specifically binds the extracellular domain of TIGIT, wherein the tumor is a solid tumor with high MSI selected from the group consisting of a MSI CRC, a MSI gastric cancer, a MSI endometrium cancer, a MSI hepatobiliary tract cancer, a MSI urinary tract cancer, a MSI brain cancer and a MSI skin cancer, wherein the antibody is administered every two weeks at a dose of about 3 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the methods of inhibiting tumor growth in a subject comprise administering to a subject a therapeutically effective amount of an antibody that specifically binds the extracellular domain of TIGIT, wherein the tumor is a solid tumor with high MSI selected from the group consisting of a MSI CRC, a MSI gastric cancer, a MSI endometrium cancer, a MSI hepatobiliary tract cancer, a MSI urinary tract cancer, a MSI brain cancer and a MSI skin cancer, wherein the antibody is administered every two weeks at a dose of about 10 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the methods of inhibiting tumor growth in a subject comprise administering to a subject a therapeutically effective amount of an antibody that specifically binds the extracellular domain of TIGIT, wherein the tumor is a solid tumor with high MSI selected from the group consisting of a MSI CRC, a MSI gastric cancer, a MSI endometrium cancer, a MSI hepatobiliary tract cancer, a MSI urinary tract cancer, a MSI brain cancer and a MSI skin cancer, wherein the antibody is administered every two weeks at a dose of about 15 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the methods of inhibiting tumor growth in a subject comprise administering to a subject a therapeutically effective amount of an antibody that specifically binds the extracellular domain of TIGIT, wherein the tumor is a tumor refractory to treatment with an anti-PD1 antibody selected from the group consisting of a melanoma, a NSCLC, a renal cell carcinoma, a squamous cell carcinoma of the head and neck, a urothelial carcinoma, a colorectal cancer (e.g. MSI or dMMR metastatic CRC) and hepatocellular carcinoma, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the antibody that specifically binds the extracellular domain of TIGIT is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise administering to a subject a therapeutically effective amount of an antibody that specifically binds the extracellular domain of TIGIT, wherein the tumor is a tumor refractory to treatment with an anti-PD-L1 antibody selected from the group consisting of a melanoma, a NSCLC, a renal cell carcinoma, a squamous cell carcinoma of the head and neck, a urothelial carcinoma, a colorectal cancer (e.g. MSI or dMMR metastatic CRC) and hepatocellular carcinoma, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the antibody that specifically binds the extracellular domain of TIGIT is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise administering to a subject a therapeutically effective amount of an antibody that specifically binds the extracellular domain of TIGIT, wherein the tumor is a tumor resistant to treatment with an anti-PD1 antibody selected from the group consisting of a melanoma, a NSCLC, a renal cell carcinoma, a squamous cell carcinoma of the head and neck, a urothelial carcinoma, a colorectal cancer (e.g. MSI or dMMR metastatic CRC) and hepatocellular carcinoma, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with an anti-PD1 antibody. In some embodiments, the antibody that specifically binds the extracellular domain of TIGIT is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise administering to a subject a therapeutically effective amount of an antibody that specifically binds the extracellular domain of TIGIT, wherein the tumor is a tumor resistant to treatment with an anti-PD-L1 antibody selected from the group consisting of a melanoma, a NSCLC, a renal cell carcinoma, a squamous cell carcinoma of the head and neck, a urothelial carcinoma, a colorectal cancer (e.g. MSI or dMMR metastatic CRC) and hepatocellular carcinoma, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the subject has previously been treated with an anti-PD-L1 antibody. In some embodiments, the antibody that specifically binds the extracellular domain of TIGIT is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise selectively administering to the subject a therapeutically effective amount of an antibody that specifically binds the extracellular domain of TIGIT, on the basis that the tumor/cancer expresses PVR and/or PVRL2, wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9). In some embodiments, the tumor is selected from the group consisting of head and neck cancer, esophageal cancer, gastric cancer, cervical cancer, TNBR, anal cancer, hepatocellular cancer, a solid tumor with high MSI (e.g. MSI CRC), NSCLC and colorectal cancer. In some embodiments, the antibody that specifically binds the extracellular domain of TIGI is administered every two weeks at a dose of about 0.3 mg/kg, about 1 mg/kg, about 3 mg/kg, about 10 mg/kg, or about 15 mg/kg.

In some embodiments, the methods of inhibiting tumor growth in a subject comprise selectively administering to the subject a therapeutically effective amount of an antibody that specifically binds the extracellular domain of TIGIT, on the basis that the tumor/cancer expresses PVR and/or PVRL2, wherein the tumor/cancer is selected from the group consisting of head and neck cancer, esophageal cancer, gastric cancer, cervical cancer, TNBR, anal cancer, hepatocellular cancer, a solid tumor with high MSI (e.g. MSI CRC), NSCLC and colorectal cancer, wherein the antibody is administered every two weeks at a dose of about 3 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the methods of inhibiting tumor growth in a subject comprise selectively administering to the subject a therapeutically effective amount of an antibody that specifically binds the extracellular domain of TIGIT, on the basis that the tumor/cancer expresses PVR and/or PVRL2, wherein the tumor/cancer is selected from the group consisting of head and neck cancer, esophageal cancer, gastric cancer, cervical cancer, TNBR, anal cancer, hepatocellular cancer, a solid tumor with high MSI (e.g. MSI CRC), NSCLC and colorectal cancer, wherein the antibody is administered every two weeks at a dose of about 10 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

In some embodiments, the methods of inhibiting tumor growth in a subject comprise selectively administering to the subject a therapeutically effective amount of an antibody that specifically binds the extracellular domain of TIGIT, on the basis that the tumor/cancer expresses PVR and/or PVRL2, wherein the tumor/cancer is selected from the group consisting of head and neck cancer, esophageal cancer, gastric cancer, cervical cancer, TNBR, anal cancer, hepatocellular cancer, a solid tumor with high MSI (e.g. MSI CRC), NSCLC and colorectal cancer, wherein the antibody is administered every two weeks at a dose of about 15 mg/kg, and wherein the antibody that binds human TIGIT comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

In Vivo Tumor Growth Inhibition in Humanized Mice by an Anti-TIGIT Antibody

A humanized mouse model was used to study the efficacy of treatment with an anti-hTIGIT antibody on a human tumor. The humanized mice were obtained from Jackson Laboratories. These mice were created by injecting human hematopoietic stem cells (CD34+ cells) into irradiated NSG mice. After 15 weeks, the presence of mature human lymphocytes was confirmed by flow cytometry. Each mouse was injected subcutaneously with patient-derived melanoma tumor cells (OMP-M9; 75,000 cells/mouse). Tumors were allowed to grow 19 days until they had reached an average volume of approximately 50 mm³. Tumor-bearing mice were randomized into groups (n=8 mice per group). Tumor-bearing mice were treated with either a control antibody or anti-hTIGIT antibody OMP-313M32. Mice were dosed every 5 days at 1 mg/kg or 5 mg/kg. Tumor growth was monitored and tumor volumes were measured with electronic calipers at the indicated time points.

As shown in FIG. 1, tumor growth was inhibited in the mice treated with antibody OMP-313M32 as compared to control. These results show that targeting TIGIT was effective at augmenting an anti-tumor immune response of human lymphocytes and contributing to inhibiting human tumor growth in vivo. In addition, these results demonstrated that humanized mouse models bearing patient-derived xenografts can be used to study the anti-hTIGIT antibody OMP-313M32 (which only binds human TIGIT) in parallel with pre-clinical studies carried out with the anti-TIGIT antibodies 313R12 and 313R19 and murine tumor models.

Example 2

Phase 1 Study

An open-label Phase 1 dose escalation and expansion study of OMP-313M32 in patients with certain locally advanced or metastatic tumors was designed. Patients have tumors that have progressed after standard therapy or have tumors where therapy has proven to be intolerable or is considered inappropriate. Prior to enrollment, patients will undergo screening to determine study eligibility. The study objectives are to evaluate the safety and tolerability of OMP-313M32 in patients; to estimate the maximum tolerated dose (MTD) of OMP-313M32; to characterize the dose-limiting toxicities (DLTs) of OMP-313M32; to identify a recommended Phase 2 dose of OMP-313M32; to characterize the pharmacokinetics of OMP-313M32; to characterize the immunogenic potential of OMP-313M32; to make preliminary assessment of the anti-tumor activity of OMP-313M32; and to make a preliminary assessment of pharmacodynamics (PD) markers.

As shown in FIG. 2, dose escalation is performed to determine the maximum tolerated dose (MTD) or the maximum administered dose (MAD) in the initial phase of the study. Dose levels of 0.3, 1.0, 3, 10, and 15 mg/kg of OMP-313M32 are administered by IV infusion once every 2 weeks. No dose escalation or reduction is allowed within a dose cohort. Three patients are treated at each dose level if no DLTs are observed. If 1 of 3 patients experiences a DLT, the dose level is expanded to 6 patients. If 2 or more patients experience a DLT, no further patients are dosed at that level and 3 additional patients are added to the preceding dose cohort unless 6 patients are being treated at that dose level. Patients are assessed for DLTs for 28 days (Day 1 to Day 29).

In the dose expansion phase of the study, patients will be enrolled at a dose level equal to the MTD or MAD of OMP-313M32. The expansion phase is designed to better characterize the safety and tolerability and to preliminarily evaluate the anti-tumor activity of OMP-313M32 in patients with specific tumor types or subtypes. The tumor types to be considered for evaluation in the dose expansion phase(s) include, but are not limited to, head and neck cancer, esophageal/gastroesophageal cancer, gastric cancer, colorectal cancer, hepatocellular cancer/liver cancer, cervical cancer, lung cancer, melanoma, Merkel cell carcinoma, renal cell carcinoma/kidney cancer, bladder cancer, ovarian cancer, pancreatic cancer, endometrial cancer, and triple negative breast cancer. As used herein, "lung cancer" includes non-small cell lung cancer (NSCLC) and small cell lung cancer. NSCLC may include NSCLC squamous cell and NSCLC adenocarcinoma. The colorectal cancers (CRCs) may include microsatellite instability-high CRC and microsatellite stable CRC. Patients in the dose expansion phase may have tumors that are resistant or refractory to treatment with a PD-1 antagonist (e.g., an anti-PD-1 antibody) or a PD-L1 antagonist (e.g., an anti-PD-L1 antibody). Patients in the dose expansion phase may be subjects that have been previously treated with a PD-1 antagonist (e.g., an anti-PD-1 antibody) or a PD-L1 antagonist (e.g., an anti-PD-L1 antibody) where tumor growth has progressed during or after treatment (may be referred to as anti-PD-1/PD-L1 progressors).

All patients enrolled in the dose escalation and expansion cohorts will undergo a biopsy prior to treatment and at least one tumor biopsy after treatment has started unless there is a medical contraindication. A biopsy will be performed at baseline and approximately 2-3 weeks after the first administration of OMP-313M32. Additional biopsies may be collected at the investigator's discretion. Biopsy methods may include core needle, punch, forceps, or excisional/incisional biopsies. The expression of TIGIT, PVR, PVRL2, FOXP3 and other immune markers will be assessed in FFPE tumor specimens. The expression levels of additional proteins and genes (e.g., immune gene signatures) may be evaluated and correlated with clinical benefit.

Example 3

TIGIT Protein Expression Assessed by IHC

To investigate TIGIT protein expression, a TIGIT immunohistochemistry (IHC) assay was developed and optimized using a proprietary mouse anti-hTIGIT monoclonal antibody. Four-micron FFPE sections were cut and mounted onto positively-charged capillary gap slides. Tissues were dewaxed through four, 5-minute changes of xylene followed by a graded alcohol series to distilled water. Steam heat-induced epitope recovery (SHIER) was performed with SHIER 2 solution (citrate-based buffer pH 6.0-6.2) for 20 minutes in the upper chamber of a Black and Decker® Steamer. Slides were pre-treated with proteinase K enzyme (1:40 dilution) for 10 minutes and were incubated in a blocking solution for 15 minutes to reduce non-specific background staining. Slides were incubated with the anti-hTIGIT antibody overnight at 1 µg/ml. To block endogenous peroxidase activity slides were incubated in hydrogen peroxide 3 times for 2.5 minutes and washed in PBS. Specific binding was detected using a Polink-2 Plus Detection Kit designed for mouse antibodies and using DAB and hematoxylin. Positive staining is indicated by the presence of a brown chromogen reaction product of the horseradish peroxidase and DAB substrate. Hematoxylin counterstain provides a blue nuclear stain to assess cell and tissue morphology.

A panel of samples covering 17 different cancer types was assessed in the IHC assay (Table 2) for staining of TIGIT in tumor cells, in tumor-associated immune cells, and in non-tumor/stromal immune cells.

TABLE 2

| Cancer Type | No. of Samples |
| --- | --- |
| NSCLC Adenocarcinoma | 25 |
| NSCLC Squamous cell carcinoma | 20 |
| Ovarian Cancer | 24 |
| Prostate Cancer | 22 |
| Pancreatic Cancer | 25 |
| Colorectal Cancer | 24 |
| Head & Neck Cancer | 20 |
| Cervical Cancer | 15 |
| Bladder Cancer | 23 |
| Esophageal Cancer | 15 |
| T-cell Lymphoma | 18 |
| Leukemia | 13 |
| Melanoma | 22 |
| Endometrial Cancer | 13 |
| Triple Negative Breast Cancer (TNBC) | 21 |
| Renal Cell Carcinoma | 27 |
| Gastric Cancer | 22 |

For tumor cells, reactivity was evaluated on the plasma membrane, using percentages observed at differential intensities. Intensity scoring included: 0=null, 1+=low or weak, 2+=moderate, and 3+=high or strong. The percentage recorded at each intensity level was reported as 0 to 100% in increments of 10 above 10% and increments of 1 below 10%. The scoring data for TIGIT expression in tumor cells was evaluated using a standard H-score approach and a Percent Score approach. The H-score is calculated using the percentage of cells with intensity of expression on a three-point semi-quantitative scale (0, 1+, 2+, or 3+). Thus, scores range from 0 to 300. H-score=[(% at 1+)×1]+[(% at 2+)×2]+[(% at 3+)×3]. The Percent Score is calculated by summing the percentage of intensities ? 1+, ? 2+, and ≥3+. Thus scores range from 0 to 100. Percent score ≥1+=(% at 1+)+(% at 2+)+(% at 3+); percent score ≥2+=(% at 2+)+(% at 3+); percent score ≥3+=(% at 3+).

Each sample was also analyzed for TIGIT reactivity in immune cells in (1) areas of stroma/non-tumor and (2) areas within tumor or closely-associated with tumor. Immune cell reactivity was scored using an Abundance Scale from 0-3 where, 0=no immune cell staining; 1=few immune cell staining; 2=moderate amount of immune cell staining; and 3=high amount of immune cell staining.

The results of the IHC assay for TIGIT expression on tumor-associated immune cells summarized in Table 3.

TABLE 3

TIGIT staining on tumor-associated immune cells

| | Cancer Indication | % of Cases with Abundance ≥ 2+ |
| --- | --- | --- |
| High Range = 30-100% of cases ≥ 2+ | TNBC | 67 |
| | T-cell lymphoma | 50 |
| | Head and Neck cancer | 35 |
| | Cervical cancer | 33 |
| Moderate Range = 10-29% of cases ≥ 2+ | Gastric cancer | 18 |
| | Melanoma | 18 |
| | NSCLC squamous cell | 15 |
| | Bladder cancer | 13 |
| | Ovarian cancer | 8 |
| Low Range = 0-9% of cases ≥ 2+ | Endometrial cancer | 8 |
| | Renal cell cancer | 7 |
| | Colon cancer | 4 |
| | NSCLC adenocarcinoma | 4 |
| | Pancreatic cancer | 4 |
| | Esophageal cancer | 0 |
| | Leukemia | 0 |
| | Prostate cancer | 0 |

Overall, triple negative breast cancer, T-cell lymphoma, head and neck cancer, and cervical cancer had the highest staining in both stroma and tumor-associated immune cells. Consistent with this IHC data, analyses of 33 tumor types in The Cancer Genome Atlas (TGCA) by RNA-Seq showed a good correlation of the expression levels of TIGIT and T-cell markers. The overall incidence of TIGIT staining on the plasma membrane of tumor cells was infrequent and low intensity. These results strongly suggest that TIGIT is expressed predominantly on immune cells in tumors and the tumor microenvironment.

Example 4

Pharmacodynamics (PD) Biomarkers

A multi-platform approach was taken to investigate anti-TIGIT treatment pharmacodynamic (PD) biomarkers in tumors and in matched whole blood samples from tumor-bearing mice treated with the surrogate anti-TIGIT antibody 313R12. Tumor tissues and matched whole blood samples were analyzed by microarray, immunochemistry (IHC), and flow cytometry for immune cell prevalence and function.

Antibody 313R12 was administered to immunocompetent mice bearing CT26.WT colon, 4T1 breast, or B16F10 melanoma tumors. These tumors are considered to have varying levels of immunogenicity—CT26.WT tumors are highly immunogenic and cytotoxic T-cell rich; 4T1 tumors are highly immunogenic and immunosuppressive; and B16F10 tumors are poorly immunogenic and immunologically silent. Mice were treated once a week in each of the models.

To identify potential gene expression PD biomarkers that correlate with efficacy, RNA was isolated from tumor tissue and peripheral blood samples collected at study termination for each of the 3 models. Microarray analyses were performed using samples from 3 animals from the following groups: (1) 4T1 tumor bearing mice treated with 0.1 mg/kg and 12.5 mg/kg 313R12, (2) B16F10 tumor-bearing mice treated with 0.1 mg/kg and 12.5 mg/kg 313R12, (3) CT26.WT tumor-bearing mice treated with 0.1, 0.5, 2.5, and 12.5 mg/kg 313R12, and (4) control mice. Global gene expression levels were profiled by microarray on treated and control tissues. Immune cell-related gene changes, with emphasis on T-cell, NK cell, and B-cell markers were examined. Changes of immune cell populations and cytokine secretions were monitored by flow cytometry, Luminex, and IHC.

In tumor samples, anti-TIGIT treatment promoted increased expression of genes associated with T-cells, CD8 T-cells, cytotoxic cells, Th1 cells, NK cells, Teff cells, and T-cell activation markers. These gene expression changes were validated by quantitative real-time PCR, (i.e., CD3e, CD8a, Ncr1, Ifn-gamma, Gzma, and CD266). Similar results were seen in gene expression changes in the blood samples. These results suggest that PD biomarkers can be used in the clinic to study on-target activity of anti-TIGIT antibody OMP-313M32.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

Following are the sequences disclosed in the application:

```
Human TIGIT amino acid sequence
                                                              (SEQ ID NO: 1)
MRWCLLLIWAQGLRQAPLASGMMTGTIETTGNISAEKGGSIILQCHLSSTTAQVTQVNWE

QQDQLLAICNADLGWHISPSFKDRVAPGPGLGLTLQSLTVNDTGEYFCIYHTYPDGTYTG

RIFLEVLESSVAEHGARFQIPLLGAMAATLVVICTAVIVVVALTRKKKALRIHSVEGDLR

RKSAGQEEWSPSAPSPPGSCVQAEAAPAGLCGEQRGEDCAELHDYFNVLSYRSLGNCSFF

TETG

Human TIGIT amino acid sequence without predicted signal sequence
                                                              (SEQ ID NO: 2)
MMTGTIETTGNISAEKGGSIILQCHLSSTTAQVTQVNWEQQDQLLAICNADLGWHISPSF

KDRVAPGPGLGLTLQSLTVNDTGEYFCIYHTYPDGTYTGRIFLEVLESSVAEHGARFQIP

LLGAMAATLVVICTAVIVVVALTRKKKALRIHSVEGDLRRKSAGQEEWSPSAPSPPGSCV

QAEAAPAGLCGEQRGEDCAELHDYFNVLSYRSLGNCSFFTETG

Human TIGIT extracellular domain amino acid sequence
                                                              (SEQ ID NO: 3)
MMTGTIETTGNISAEKGGSIILQCHLSSTTAQVTQVNWEQQDQLLAICNADLGWHISPSF
KDRVAPGPGLGLTLQSLTVNDTGEYFCIYHTYPDGTYTGRIFLEVLESSVAEHGARFQIP OMP-313M32/313M33 Heavy chain CDR1
                                                              (SEQ ID NO: 4)
TSDYAWN OMP-313M32/313M33 Heavy chain CDR2
                                                              (SEQ ID NO: 5)
YISYSGSTSYNPSLRS OMP-313M32/313M33 Heavy chain CDR3
                                                              (SEQ ID NO: 6)
ARRQVGLGFAY OMP-313M32/313M33 Light chain CDR1
                                                              (SEQ ID NO: 7)
KASQDVSTAVA OMP-313M32/313M33 Light chain CDR2
                                                              (SEQ ID NO: 8)
SASYRYT OMP-313M32/313M33 Light chain CDR3
                                                              (SEQ ID NO: 9)
QQHYSTP OMP-313M32/313M33 Heavy chain variable region amino acid sequence
                                                              (SEQ ID NO: 10)
QVQLQESGPGLVKPSETLSLTCAVSGYSITSDYAWNWIRQPPGKGLEWIGYISYSGSTSY
NPSLRSRVTISRDTSKNQFFLKLSSVTAADTAVYYCARRQVGLGFAYWGQGTLVTVSS
```

OMP-313M32/313M33 Light chain variable region amino acid sequence
(SEQ ID NO: 11)
DIQMTQSPSSLSASVGDRVTITCKASQDVSTAVAWYQQKPGKAPKLLIYSASYRYTGVPS
RFSGSGSGTDFTFTISSLQPEDIATYYCQQHYSTPWTFG OMP-313M32 Heavy chain (IgG1) amino acid sequence with predicted signal
sequence underlined
(SEQ ID NO: 12)
MDWTWRILFLVAAATGAHSQVQLQESGPGLVKPSETLSLTCAVSGYSITSDYAWNWIRQP

PGKGLEWIGYISYSGSTSYNPSLRSRVTISRDTSKNQFFLKLSSVTAADTAVYYCARRQV

GLGFAYWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSC

DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

OMP-313M32 Heavy chain (IgG1) amino acid sequence without signal sequence
(SEQ ID NO: 13)
QVQLQESGPGLVKPSETLSLTCAVSGYSITSDYAWNWIRQPPGKGLEWIGYISYSGSTSY

NPSLRSRVTISRDTSKNQFFLKLSSVTAADTAVYYCARRQVGLGFAYWGQGTLVTVSSAS

TKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKRVEPKSCDKTHTCPPCPAPELLGGPS

VFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSKLTVDKSRWQQ

GNVFSCSVMHEALHNHYTQKSLSLSPGK

OMP-313M32/313M33 Light chain amino acid sequence with predicted signal
sequence underlined
(SEQ ID NO: 14)
MVLQTQVFISLLLLWISGAYGDIQMTQSPSSLSASVGDRVTITCKASQDVSTAVAWYQQKP

GKAPKLLIYSASYRYTGVPSRFSGSGSGTDFTFTISSLQPEDIATYYCQQHYSTPWTFGQ

GTKVEIKRTVAAPSVFIFPPSDEQLKSGTASVVCLLNNFYPREAKVQWKVDNALQSGNSQ

ESVTEQDSKDSTYSLSNTLTLSKADYEKHKVYACEVTHQGLSSPVTKSFNRGEC

OMP-313M32/313M33 Light chain amino acid sequence without signal sequence
(SEQ ID NO: 15)
DIQMTQSPSSLSASVGDRVTITCKASQDVSTAVAWYQQKPGKAPKLLIYSASYRYTGVPS

RFSGSGSGTDFTFTISSLQPEDIATYYCQQHYSTPWTFGQGTKVEIKRTVAAPSVFIFPP

SDEQLKSGTASVVCLLNNFYPREAKVQWKVDNALQSGNSQESVTEQDSKDSTYSLSNTLT

LSKADYEKHKVYACEVTHQGLSSPVTKSFNRGEC

313M33 Heavy chain (IgG4) amino acid sequence with predicted signal
sequence underlined
(SEQ ID NO: 16)
MDWTWRILFLVAAATGAHSQVQLQESGPGLVKPSETLSLTCAVSGYSITSDYAWNWIRQP

PGKGLEWIGYISYSGSTSYNPSLRSRVTISRDTSKNQFFLKLSSVTAADTAVYYCARRQV

GLGFAYWGQGTLVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVESKYG

PPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

313M33 Heavy chain (IgG4) amino acid sequence without signal sequence
(SEQ ID NO: 17)
QVQLQESGPGLVKPSETLSLTCAVSGYSITSDYAWNWIRQPPGKGLEWIGYISYSGSTSY

NPSLRSRVTISRDTSKNQFFLKLSSVTAADTAVYYCARRQVGLGFAYWGQGTLVTVSSAS

TKGPSVFPLAPCSRSTSESTAALGCLVKDYFPEPVTVSWNSGALTSGVHTFPAVLQSSGL

YSLSSVVTVPSSSLGTKTYTCNVDHKPSNTKVDKRVESKYGPPCPSCPAPEFLGGPSVFL

FPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVDKSRWQEGNVF

SCSVMHEALHNHYTQKSLSLSLGK

OMP-313M32/313M33 Heavy chain variable region nucleotide sequence
(SEQ ID NO: 18)
CAGGTCCAGCTGCAGGAGTCTGGCCCAGGACTGGTGAAGCCTTCTGAGACCCTGTCCCTC

ACCTGCGCTGTCTCTGGTTACTCCATCACCTCCGATTATGCCTGGAACTGGATTCGGCAG

CCCCCAGGGAAGGGGCTGGAGTGGATTGGGTACATAAGCTACTCTGGTAGCACTAGCTAC

AACCCATCTCTCCGGTCACGGGTCACAATATCACGGGACACATCCAAGAACCAGTTCTTC

CTGAAGCTGTCCTCTGTGACCGCCGCTGACACCGCCGTGTATTACTGTGCAAGGAGACAG

GTCGGGCTGGGGTTTGCTTACTGGGGCCAAGGAACCCTGGTCACCGTCAGCTCA

OMP-313M32/313M33 Light chain variable region nucleotide sequence
(SEQ ID NO: 19)
GACATCCAGATGACCCAGTCTCCATCCTCCCTGTCTGCATCTGTTGGAGACAGAGTCACC

ATCACTTGCAAGGCTTCTCAGGATGTGTCTACTGCTGTTGCCTGGTATCAGCAGAAACCA

GGGAAAGCCCCTAAGCTCCTGATCTACTCTGCATCCTATCGGTACACTGGGGTCCCATCA

AGGTTCTCCGGATCTGGATCTGGGACAGATTTTACTTTCACCATCAGCAGCCTGCAGCCT

GAAGATATTGCAACATATTACTGTCAGCAACATTATTCTACTCCTTGGACATTCGGC

OMP-313M32 Heavy chain (IgG1) nucleotide sequence
(SEQ ID NO: 20)
ATGGACTGGACCTGGAGGATACTCTTTCTCGTGGCTGCAGCCACAGGAGCCCACTCCCAG

GTCCAGCTGCAGGAGTCTGGCCCAGGACTGGTGAAGCCTTCTGAGACCCTGTCCCTCACC

TGCGCTGTCTCTGGTTACTCCATCACCTCCGATTATGCCTGGAACTGGATTCGGCAGCCC

CCAGGGAAGGGGCTGGAGTGGATTGGGTACATAAGCTACTCTGGTAGCACTAGCTACAAC

CCATCTCTCCGGTCACGGGTCACAATATCACGGGACACATCCAAGAACCAGTTCTTCCTG

AAGCTGTCCTCTGTGACCGCCGCTGACACCGCCGTGTATTACTGTGCAAGGAGACAGGTC

GGGCTGGGGTTTGCTTACTGGGGCCAAGGAACCCTGGTCACCGTCAGCTCAGCCAGCACA

AAGGGCCCCTCCGTGTTCCCTCTGGCCCCTTCCTCCAAGTCCACCTCCGGCGGCACCGCC

GCTCTGGGCTGCCTGGTGAAGGACTACTTCCCTGAGCCTGTGACCGTGTCCTGGAACTCT

GGCGCCCTGACCTCTGGCGTGCACACCTTCCCAGCCGTGCTGCAGTCCTCCGGCCTGTAC

TCCCTGTCCTCCGTGGTGACCGTGCCTTCCTCCTCCCTGGGCACCCAGACCTACATCTGC

AACGTGAACCACAAGCCTTCCAACACCAAGGTGGACAAGCGGGTGGAGCCTAAGTCCTGC

GACAAGACCCACACCTGCCCTCCCTGCCCTGCCCCTGAGCTGCTGGGCGGACCTTCCGTG

TTCCTGTTCCCTCCTAAGCCTAAGGACACCCTGATGATCTCCCGGACCCCTGAGGTGACC

TGCGTGGTGGTGGACGTGTCCCACGAGGATCCTGAGGTGAAGTTCAATTGGTACGTGGAC

GGCGTGGAGGTGCACAACGCTAAGACCAAGCCAAGGGAGGAGCAGTACAACTCCACCTAC

CGGGTGGTGTCTGTGCTGACCGTGCTGCACCAGGACTGGCTGAACGGCAAAGAATACAAG

```
TGCAAGGTCTCCAACAAGGCCCTGCCCGCTCCCATCGAGAAAACCATCTCCAAGGCCAAG

GGCCAGCCTCGCGAGCCTCAGGTGTACACCCTGCCACCCAGCCGGGAGGAGATGACCAAG

AACCAGGTGTCCCTGACCTGTCTGGTGAAGGGCTTCTACCCTTCCGATATCGCCGTGGAG

TGGGAGTCTAACGGCCAGCCCGAGAACAACTACAAGACCACCCCTCCTGTGCTGGACTCC

GACGGCTCCTTCTTCCTGTACTCCAAGCTGACCGTGGACAAGTCCCGGTGGCAGCAGGGC

AACGTGTTCTCCTGCTCCGTGATGCACGAGGCCCTGCACAACCACTACACCCAGAAGAGC

CTGTCTCTGTCTCCTGGCAAGTGA
```

OMP-313M32/313M33 Light chain nucleotide sequence (SEQ ID NO: 21)

```
ATGGTGCTCCAGACCCAGGTCTTCATTTCCCTGCTGCTCTGGATCAGCGGAGCCTACGGG

GACATCCAGATGACCCAGTCTCCATCCTCCCTGTCTGCATCTGTTGGAGACAGAGTCACC

ATCACTTGCAAGGCTTCTCAGGATGTGTCTACTGCTGTTGCCTGGTATCAGCAGAAACCA

GGGAAAGCCCCTAAGCTCCTGATCTACTCTGCATCCTATCGGTACACTGGGGTCCCATCA

AGGTTCTCCGGATCTGGATCTGGGACAGATTTTACTTTCACCATCAGCAGCCTGCAGCCT

GAAGATATTGCAACATATTACTGTCAGCAACATTATTCTACTCCTTGGACATTCGGCCAA

GGGACCAAGGTGGAAATCAAACGTACGGTGGCTGCACCATCTGTCTTCATCTTCCCTCCA

TCTGATGAGCAGCTCAAATCTGGAACTGCCTCTGTTGTGTGCCTGCTGAATAACTTCTAT

CCCAGAGAGGCCAAAGTCCAGTGGAAGGTGGATAACGCCCTCCAATCCGGCAACTCCCAG

GAGAGTGTCACAGAGCAGGACAGCAAGGACAGCACCTACAGCCTCAGCAACACCCTGACA

CTGAGCAAAGCAGACTACGAGAAACACAAAGTCTATGCCTGCGAAGTCACCCATCAGGGC

CTGTCTTCCCCCGTCACAAAGAGCTTCAACAGGGGAGAGTGCTAA
```

313M33 Heavy chain (IgG4) nucleotide sequence (SEQ ID NO: 22)

```
ATGGACTGGACCTGGAGGATACTCTTTCTCGTGGCTGCAGCCACAGGAGCCCACTCCCAG

GTCCAGCTGCAGGAGTCTGGCCCAGGACTGGTGAAGCCTTCTGAGACCCTGTCCCTCACC

TGCGCTGTCTCTGGTTACTCCATCACCTCCGATTATGCCTGGAACTGGATTCGGCAGCCC

CCAGGGAAGGGGCTGGAGTGGATTGGGTACATAAGCTACTCTGGTAGCACTAGCTACAAC

CCATCTCTCCGGTCACGGGTCACAATATCACGGGACACATCCAAGAACCAGTTCTTCCTG

AAGCTGTCCTCTGTGACCGCCGCTGACACCGCCGTGTATTACTGTGCAAGGAGACAGGTC

GGGCTGGGGTTTGCTTACTGGGGCCAAGGAACCCTGGTCACCGTCAGCTCAGCCAGCACA

AAGGGCCCATCCGTCTTCCCCCTGGCACCCTGCTCCCGGAGCACCTCCGAGAGCACAGCC

GCCCTGGGCTGCCTGGTCAAGGACTACTTCCCCGAACCCGTTACCGTGTCTTGGAACTCC

GGCGCACTGACCAGCGGCGTGCACACCTTCCCTGCTGTCCTCCAATCCTCTGGACTCTAC

TCCCTCTCCTCCGTGGTGACAGTGCCCTCCAGCAGCCTGGGCACTAAGACCTACACCTGC

AACGTCGATCACAAGCCCAGCAACACCAAGGTGGACAAGAGAGTTGAGTCCAAATATGGA

CCCCCATGCCCACCTTGCCCAGCACCTGAGTTCCTGGGGGGACCATCAGTCTTCCTGTTC

CCCCCAAAACCCAAGGACACTCTCATGATCTCCCGGACCCCTGAGGTCACTTGCGTGGTG

GTGGACGTGAGCCAGGAAGACCCCGAGGTCCAGTTCAACTGGTATGTGGATGGCGTGGAG

GTTCATAATGCCAAGACAAAGCCTCGGGAGGAGCAGTTCAACAGCACCTACCGGGTGGTC

AGCGTCCTCACCGTCCTGCACCAAGACTGGCTGAACGGCAAGGAGTACAAGTGCAAGGTC

TCCAACAAAGGGCTCCCATCCTCCATCGAGAAAACCATCTCCAAAGCCAAAGGGCAGCCC

CGGGAGCCACAGGTGTACACCCTGCCCCCATCCCAAGAGGAGATGACCAAGAACCAAGTG
```

-continued

```
TCCCTGACCTGCCTGGTCAAAGGCTTCTACCCCAGCGACATCGCCGTGGAGTGGGAGAGC

AATGGGCAGCCTGAGAACAACTACAAGACCACTCCTCCCGTGCTGGACTCCGACGGCTCC

TTCTTCCTCTACTCCCGGCTCACCGTGGACAAGAGCAGGTGGCAGGAGGGCAATGTCTTC

TCCTGCTCCGTGATGCATGAGGCTCTGCACAACCACTACACACAGAAGAGCCTCTCCCTG

TCTCTGGGCAAATGA
```

Human IgG1 Heavy chain constant region (SEQ ID NO: 23)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG2 Heavy chain constant region (SEQ ID NO: 24)

ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGK

Human IgG3 Heavy chain constant region (SEQ ID NO: 25)

ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDT

LMISRTPEVTCVVVDVSHEDPEVQFKWYVDGVEVHNAKTKPREEQYNSTFRVVSVLTVLH

QDWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMHE

ALHNRFTQKSLSLSPGK

Human IgG4 Heavy chain constant region (SEQ ID NO: 26)

ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

Human TIGIT amino acids 55-70

(SEQ ID NO: 27)

TQVNWEQQDQLLAICN

Human TIGIT amino acids 105-122

(SEQ ID NO: 28)

EYFCIYHTYPDGTYTGRI

FLAG Tag (SEQ ID NO: 29)

DYKDDDDK

What is claimed is:

1. A method of inhibiting cancer in a human patient having cancer, comprising administering to said human patient a therapeutically effective amount of a full-length antibody that specifically binds the extracellular domain of human TIGIT,
   wherein said cancer is a head and neck cancer, cervical carcinoma, gastric cancer, ovarian cancer, melanoma, sarcoma, lung cancer, gastroesophageal, leukemia, lymphoma, anal cancer, pancreatic cancer, hepatocellular cancer, liver cancer, renal cell carcinoma, kidney cancer, bladder cancer, a micro satellite instability-high colorectal cancer, a micro satellite stable colorectal cancer, a triple negative breast cancer, a Merkel cell carcinoma, an endometrial cancer, or an esophageal cancer; and
   wherein said full-length antibody that binds human TIGIT is capable of mediating antibody-dependent cell cytotoxicity (ADCC) and/or complement-dependent cytotoxicity (CDC) and comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

2. The method of claim 1 wherein said human patient was previously treated with a human PD-1 antagonist or a human PD-L1 antagonist and there is tumor growth, progression, or recurrence during or after treatment with said human PD-1 antagonist or said human PD-L1 antagonist.

3. The method of claim 1, wherein said antibody that binds human TIGIT comprises:
   (i) a heavy chain variable region comprising SEQ ID NO: 10 and a light chain variable region comprising SEQ ID NO: 11;
   (ii) a heavy chain amino acid sequence of SEQ ID NO: 13 and a light chain amino acid sequence of SEQ ID NO: 15; or
   (iii) a heavy chain amino acid sequence of SEQ ID NO: 17 and a light chain amino acid sequence of SEQ ID NO: 15.

4. The method of claim 1, wherein said antibody that binds human TIGIT comprises:
   (i) a heavy chain variable region comprising SEQ ID NO: 10 and a light chain variable region comprising SEQ ID NO: 11; or
   (ii) a heavy chain amino acid sequence of SEQ ID NO: 13 and a light chain amino acid sequence of SEQ ID NO: 15.

5. The method of claim 1, wherein said antibody that binds human TIGIT comprises a heavy chain variable region encoded by the plasmid deposited with ATCC as Designation No. PTA-122346 and a light chain variable region encoded by the plasmid deposited with ATCC as Designation No. PTA-122347.

6. The method of claim 1, wherein the method further comprises administering to said patient an additional human therapeutic agent, wherein said additional human therapeutic agent is administered prior to, concurrently with, or subsequently to the administration of said antibody that binds to human TIGIT.

7. The method of claim 1, wherein the method further comprises administering to said patient at least one additional therapeutic agent selected from the group consisting of nivolumab, pembrolizumab, atezolizumab, avelumab, ipilimumab, bevacizumab, ramucirumab, trastuzumab, pertuzumab, panitumumab, cetuximab, cemiplimab, and durvalumab wherein said additional therapeutic agent is administered prior to, concurrently with, or subsequently to the administration of said antibody that binds to human TIGIT.

8. The method of claim 7, wherein said additional therapeutic agent is selected from the group consisting of nivolumab, pembrolizumab, and ipilimumab.

9. The method of claim 1, wherein said antibody that binds human TIGIT is intravenously administered to said human patient.

10. The method of claim 1, wherein said antibody that binds human TIGIT is administered once every week, once every two weeks, once every three weeks, or once every four weeks.

11. The method of claim 1 wherein said antibody that binds human TIGIT comprises:
   a heavy chain amino acid sequence of SEQ ID NO: 13 and a light chain amino acid sequence of SEQ ID NO:15;
   wherein said antibody that binds human TIGIT is intravenously administered to said human patient;
   wherein said antibody that binds human TIGIT is administered once every week, once every two weeks, once every three weeks, or once every four weeks; and
   wherein the method further comprises administering to said patient at least one additional human therapeutic agent, wherein said additional human therapeutic agent is administered prior to, concurrently with, or subsequently to the administration of said antibody that binds to human TIGIT.

12. A method of inhibiting cancer in a human patient having cancer, comprising administering to said human patient a therapeutically effective amount of a full-length antibody that specifically binds the extracellular domain of human TIGIT,
   wherein said human patient was previously treated with a human PD-1 antagonist or a human PD-L1 antagonist and there is tumor growth, progression, or recurrence during or after treatment with said human PD-1 antagonist or said human PD-L1 antagonist; and
   wherein said full-length antibody that binds human TIGIT is capable of mediating antibody-dependent cell cytotoxicity (ADCC) and/or complement-dependent cytotoxicity (CDC) and comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

13. The method of claim 12, wherein said antibody that binds human TIGIT comprises:
   (i) a heavy chain variable region comprising SEQ ID NO: 10 and a light chain variable region comprising SEQ ID NO: 11;
   (ii) a heavy chain amino acid sequence of SEQ ID NO: 13 and a light chain amino acid sequence of SEQ ID NO: 15; or
   (iii) a heavy chain amino acid sequence of SEQ ID NO: 17 and a light chain amino acid sequence of SEQ ID NO: 15.

14. The method of claim 12, wherein said antibody that binds human TIGIT comprises:

(i) a heavy chain variable region comprising SEQ ID NO: 10 and a light chain variable region comprising SEQ ID NO: 11; or
(ii) a heavy chain amino acid sequence of SEQ ID NO: 13 and a light chain amino acid sequence of SEQ ID NO: 15.

15. The method of claim 12, wherein the method further comprises administering to said patient an additional human therapeutic agent, wherein said additional human therapeutic agent is administered prior to, concurrently with, or subsequently to the administration of said antibody that binds to human TIGIT.

16. The method of claim 15, wherein the method further comprises administering to said patient at least one additional therapeutic agent selected from the group consisting of nivolumab, pembrolizumab, atezolizumab, avelumab, ipilimumab, bevacizumab, ramucirumab, trastuzumab, pertuzumab, panitumumab, cetuximab, cemiplimab, and durvalumab wherein said additional therapeutic agent is administered prior to, concurrently with, or subsequently to the administration of said antibody that binds to human TIGIT.

17. The method of claim 16, wherein said additional therapeutic agent is selected from the group consisting of nivolumab, pembrolizumab, and ipilimumab.

18. The method of claim 12, wherein said antibody that binds human TIGIT is intravenously administered to said subject.

19. The method of claim 12, wherein said antibody that binds human TIGIT is administered once every week, once every two weeks, once every three weeks, or once every four weeks.

20. The method of claim 12, wherein said cancer is a head and neck cancer, cervical carcinoma, gastric cancer, ovarian cancer, melanoma, sarcoma, lung cancer, gastroesophageal, leukemia, lymphoma, anal cancer, pancreatic cancer, hepatocellular cancer, liver cancer, renal cell carcinoma, kidney cancer, bladder cancer, a microsatellite instability-high colorectal cancer, a microsatellite stable colorectal cancer, a triple negative breast cancer, a Merkel cell carcinoma, an endometrial cancer, or an esophageal cancer.

21. The method of claim 12 wherein said antibody that binds human TIGIT comprises:
a heavy chain amino acid sequence of SEQ ID NO: 13 and a light chain amino acid sequence of SEQ ID NO:15;
wherein said antibody that binds human TIGIT is intravenously administered to said human patient;
wherein said antibody that binds human TIGIT is administered once every week, once every two weeks, once every three weeks, or once every four weeks; and
wherein the method further comprises administering to said patient at least one additional human therapeutic agent, wherein said additional human therapeutic agent is administered prior to, concurrently with, or subsequently to the administration of said antibody that binds to human TIGIT.

22. A method of inhibiting cancer in a human patient having cancer, comprising administering to said human patient a therapeutically effective amount of a full-length antibody that specifically binds the extracellular domain of human TIGIT,
wherein the cancer expresses poliovirus receptor (PVR) and/or poliovirus receptor-related 2 (PVRL2); and wherein said full-length antibody that binds human TIGIT is capable of mediating antibody-dependent cell cytotoxicity (ADCC) and/or complement-dependent cytotoxicity (CDC) and comprises a heavy chain CDR1 comprising TSDYAWN (SEQ ID NO:4), a heavy chain CDR2 comprising YISYSGSTSYNPSLRS (SEQ ID NO:5), a heavy chain CDR3 comprising ARRQVGLGFAY (SEQ ID NO:6), a light chain CDR1 comprising KASQDVSTAVA (SEQ ID NO:7), a light chain CDR2 comprising SASYRYT (SEQ ID NO:8), and a light chain CDR3 comprising QQHYSTP (SEQ ID NO:9).

23. The method of claim 22, wherein the antibody that binds human TIGIT comprises:
(i) a heavy chain variable region comprising SEQ ID NO: 10 and a light chain variable region comprising SEQ ID NO: 11;
(ii) a heavy chain amino acid sequence of SEQ ID NO: 13 and a light chain amino acid sequence of SEQ ID NO: 15; or
(iii) a heavy chain amino acid sequence of SEQ ID NO: 17 and a light chain amino acid sequence of SEQ ID NO: 15.

24. The method of claim 22, wherein the antibody that binds human TIGIT comprises:
(i) a heavy chain variable region comprising SEQ ID NO: 10 and a light chain variable region comprising SEQ ID NO: 11; or
(ii) a heavy chain amino acid sequence of SEQ ID NO: 13 and a light chain amino acid sequence of SEQ ID NO: 15.

25. The method of claim 22, wherein the method further comprises administering to said patient an additional human therapeutic agent, wherein said additional human therapeutic agent is administered prior to, concurrently with, or subsequently to the administration of said antibody that binds to human TIGIT.

26. The method of claim 25, wherein the method further comprises administering to said patient at least one additional therapeutic agent selected from the group consisting of nivolumab, pembrolizumab, atezolizumab, avelumab, ipilimumab, bevacizumab, ramucirumab, trastuzumab, pertuzumab, panitumumab, cetuximab, cemiplimab, and durvalumab wherein said additional therapeutic agent is administered prior to, concurrently with, or subsequently to the administration of said antibody that binds to human TIGIT.

27. The method of claim 25, wherein said additional therapeutic agent is selected from the group consisting of nivolumab, pembrolizumab, and ipilimumab.

28. The method of claim 22, wherein said antibody that binds human TIGIT is intravenously administered to said human patient, and wherein said antibody that binds human TIGIT is administered once every week, once every two weeks, once every three weeks, or once every four weeks.

29. The method of claim 22, wherein said cancer is a head and neck cancer, cervical carcinoma, gastric cancer, ovarian cancer, melanoma, sarcoma, lung cancer, gastroesophageal, leukemia, lymphoma, anal cancer, pancreatic cancer, hepatocellular cancer, liver cancer, renal cell carcinoma, kidney cancer, bladder cancer, a micro satellite instability-high colorectal cancer, a micro satellite stable colorectal cancer, a triple negative breast cancer, a Merkel cell carcinoma, an endometrial cancer, or an esophageal cancer.

30. The method of claim 22 wherein said antibody that binds human TIGIT comprises:
a heavy chain amino acid sequence of SEQ ID NO: 13 and a light chain amino acid sequence of SEQ ID NO:15;
wherein said antibody that binds human TIGIT is intravenously administered to said human patient;

wherein said antibody that binds human TIGIT is administered once every week, once every two weeks, once every three weeks, or once every four weeks; and wherein the method further comprises administering to said patient at least one additional human therapeutic agent, wherein said additional human therapeutic agent is administered prior to, concurrently with, or subsequently to the administration of said antibody that binds to human TIGIT.

* * * * *

UNITED STATES PATENT AND TRADEMARK OFFICE
CERTIFICATE OF CORRECTION

PATENT NO. : 11,136,384 B2  
APPLICATION NO. : 17/119883  
DATED : October 5, 2021  
INVENTOR(S) : Jakob Dupont et al.

Page 1 of 1

It is certified that error appears in the above-identified patent and that said Letters Patent is hereby corrected as shown below:

On the Title Page

Add the following inventors in item (72):  
--Austin L. Gurney, Redwood City, CA (US)  
Ming-Hong Xie, Redwood City, CA (US)--

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 29

<210> SEQ ID NO 1
<211> LENGTH: 244
<212> TYPE: PRT
<213> ORGANISM: Artificial Sequence
<220> FEATURE:
<223> OTHER INFORMATION: Human TIGIT amino acid sequence

<400> SEQUENCE: 1

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 2
<211> LENGTH: 223
<212> TYPE: PRT
<213> ORGANISM: Artificial Sequence
<220> FEATURE:
<223> OTHER INFORMATION: Human TIGIT amino acid sequence without
      predicted signal sequence

<400> SEQUENCE: 2

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

```
Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65              70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Val Ala Glu
                100                 105                 110

His Gly Ala Arg Phe Gln Ile Pro Leu Leu Gly Ala Met Ala Ala Thr
                115                 120                 125

Leu Val Val Ile Cys Thr Ala Val Ile Val Val Ala Leu Thr Arg
130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
                180                 185                 190

Gln Arg Gly Glu Asp Cys Ala Glu Leu His Asp Tyr Phe Asn Val Leu
                195                 200                 205

Ser Tyr Arg Ser Leu Gly Asn Cys Ser Phe Phe Thr Glu Thr Gly
210                 215                 220

<210> SEQ ID NO 3
<211> LENGTH: 120
<212> TYPE: PRT
<213> ORGANISM: Artificial Sequence
<220> FEATURE:
<223> OTHER INFORMATION: Human TIGIT extracellular domain amino acid
      sequence

<400> SEQUENCE: 3

Met Met Thr Gly Thr Ile Glu Thr Thr Gly Asn Ile Ser Ala Glu Lys
 1               5                  10                  15

Gly Gly Ser Ile Ile Leu Gln Cys His Leu Ser Ser Thr Thr Ala Gln
                 20                  25                  30

Val Thr Gln Val Asn Trp Glu Gln Gln Asp Gln Leu Leu Ala Ile Cys
                 35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65              70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Val Ala Glu
                100                 105                 110

His Gly Ala Arg Phe Gln Ile Pro
            115                 120

<210> SEQ ID NO 4
<211> LENGTH: 7
<212> TYPE: PRT
<213> ORGANISM: Artificial Sequence
<220> FEATURE:
<223> OTHER INFORMATION: OMP-313M32/313M33 Heavy chain CDR1

<400> SEQUENCE: 4

Thr Ser Asp Tyr Ala Trp Asn
```

<210> SEQ ID NO 5
<211> LENGTH: 16
<212> TYPE: PRT
<213> ORGANISM: Artificial Sequence
<220> FEATURE:
<223> OTHER INFORMATION: OMP-313M32/313M33 Heavy chain CDR2

<400> SEQUENCE: 5

Tyr Ile Ser Tyr Ser Gly Ser Thr Ser Tyr Asn Pro Ser Leu Arg Ser
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: OMP-313M32/313M33 Heavy chain CDR3

<400> SEQUENCE: 6

Ala Arg Arg Gln Val Gly Leu Gly Phe Ala Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: OMP-313M32/313M33 Light chain CDR1

<400> SEQUENCE: 7

Lys Ala Ser Gln Asp Val Ser Thr Ala Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: OMP-313M32/313M33 Light chain CDR2

<400> SEQUENCE: 8

Ser Ala Ser Tyr Arg Tyr Thr
1               5

<210> SEQ ID NO 9
<211> LENGTH: 7
<212> TYPE: PRT
<213> ORGANISM: Artificial Sequence
<220> FEATURE:
<223> OTHER INFORMATION: OMP-313M32/313M33 Light chain CDR3

<400> SEQUENCE: 9

Gln Gln His Tyr Ser Thr Pro
1               5

<210> SEQ ID NO 10
<211> LENGTH: 118
<212> TYPE: PRT
<213> ORGANISM: Artificial Sequence
<220> FEATURE:
<223> OTHER INFORMATION: OMP-313M32/313M33 Heavy chain variable region
      amino acid sequence

<400> SEQUENCE: 10

Gln Val Gln Leu Gln Glu Ser Gly Pro Gly Leu Val Lys Pro Ser Glu

-continued

```
                1               5                  10                 15
            Thr Leu Ser Leu Thr Cys Ala Val Ser Gly Tyr Ser Ile Thr Ser Asp
                      20                 25                 30
            Tyr Ala Trp Asn Trp Ile Arg Gln Pro Pro Gly Lys Gly Leu Glu Trp
                      35                 40                 45
            Ile Gly Tyr Ile Ser Tyr Ser Gly Ser Thr Ser Tyr Asn Pro Ser Leu
                      50                 55                 60
            Arg Ser Arg Val Thr Ile Ser Arg Asp Thr Ser Lys Asn Gln Phe Phe
             65                 70                 75                 80
            Leu Lys Leu Ser Ser Val Thr Ala Ala Asp Thr Ala Val Tyr Tyr Cys
                      85                 90                 95
            Ala Arg Arg Gln Val Gly Leu Gly Phe Ala Tyr Trp Gly Gln Gly Thr
                      100                105                110
            Leu Val Thr Val Ser Ser
                      115

<210> SEQ ID NO 11
<211> LENGTH: 99
<212> TYPE: PRT
<213> ORGANISM: Artificial Sequence
<220> FEATURE:
<223> OTHER INFORMATION: OMP-313M32/313M33 Light chain variable region
      amino acid sequence

<400> SEQUENCE: 11

Asp Ile Gln Met Thr Gln Ser Pro Ser Ser Leu Ser Ala Ser Val Gly
             1               5                  10                 15
            Asp Arg Val Thr Ile Thr Cys Lys Ala Ser Gln Asp Val Ser Thr Ala
                      20                 25                 30
            Val Ala Trp Tyr Gln Gln Lys Pro Gly Lys Ala Pro Lys Leu Leu Ile
                      35                 40                 45
            Tyr Ser Ala Ser Tyr Arg Tyr Thr Gly Val Pro Ser Arg Phe Ser Gly
                      50                 55                 60
            Ser Gly Ser Gly Thr Asp Phe Thr Phe Thr Ile Ser Ser Leu Gln Pro
             65                 70                 75                 80
            Glu Asp Ile Ala Thr Tyr Tyr Cys Gln Gln His Tyr Ser Thr Pro Trp
                      85                 90                 95
            Thr Phe Gly

<210> SEQ ID NO 12
<211> LENGTH: 467
<212> TYPE: PRT
<213> ORGANISM: Artificial Sequence
<220> FEATURE:
<223> OTHER INFORMATION: OMP-313M32 Heavy chain (IgG1) amino acid
      sequence with predicted signal sequence
<220> FEATURE:
<221> NAME/KEY: MISC_FEATURE
<222> LOCATION: (1)..(19)
<223> OTHER INFORMATION: predicted signal sequence

<400> SEQUENCE: 12

Met Asp Trp Thr Trp Arg Ile Leu Phe Leu Val Ala Ala Ala Thr Gly
             1               5                  10                 15
            Ala His Ser Gln Val Gln Leu Gln Glu Ser Gly Pro Gly Leu Val Lys
                      20                 25                 30
            Pro Ser Glu Thr Leu Ser Leu Thr Cys Ala Val Ser Gly Tyr Ser Ile
                      35                 40                 45
            Thr Ser Asp Tyr Ala Trp Asn Trp Ile Arg Gln Pro Pro Gly Lys Gly
```

```
            50                  55                  60
Leu Glu Trp Ile Gly Tyr Ile Ser Tyr Ser Gly Ser Thr Ser Tyr Asn
65                  70                  75                  80

Pro Ser Leu Arg Ser Arg Val Thr Ile Ser Arg Asp Thr Ser Lys Asn
                85                  90                  95

Gln Phe Phe Leu Lys Leu Ser Ser Val Thr Ala Ala Asp Thr Ala Val
            100                 105                 110

Tyr Tyr Cys Ala Arg Arg Gln Val Gly Leu Gly Phe Ala Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465
```

<210> SEQ ID NO 13
<211> LENGTH: 448
<212> TYPE: PRT
<213> ORGANISM: Artificial Sequence
<220> FEATURE:
<223> OTHER INFORMATION: OMP-313M32 Heavy chain (IgG1) amino acid sequence without signal sequence

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Ser Tyr Asn Pro Ser Leu
    50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                355                 360                 365
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
                435                 440                 445

<210> SEQ ID NO 14
<211> LENGTH: 234
<212> TYPE: PRT
<213> ORGANISM: Artificial Sequence
<220> FEATURE:
<223> OTHER INFORMATION: OMP-313M32/313M33 Light chain amino acid
      sequence with predicted signal sequence
<220> FEATURE:
<221> NAME/KEY: MISC_FEATURE
<222> LOCATION: (1)..(20)
<223> OTHER INFORMATION: predicted signal sequence

<400> SEQUENCE: 14

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Gln Gln His Tyr
            100                 105                 110

Ser Thr Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 15
```

<211> LENGTH: 214
<212> TYPE: PRT
<213> ORGANISM: Artificial Sequence
<220> FEATURE:
<223> OTHER INFORMATION: OMP-313M32/313M33 Light chain amino acid
      sequence without signal sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 464
<212> TYPE: PRT
<213> ORGANISM: Artificial Sequence
<220> FEATURE:
<223> OTHER INFORMATION: 313M33 Heavy chain (IgG4) amino acid sequence
      with predicted signal sequence
<220> FEATURE:
<221> NAME/KEY: MISC_FEATURE
<222> LOCATION: (1)..(19)
<223> OTHER INFORMATION: predicted signal sequence

<400> SEQUENCE: 16

Met Asp Trp Thr Trp Arg Ile Leu Phe Leu Val Ala Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Thr Ser Asp Tyr Ala Trp Asn Trp Ile Arg Gln Pro Pro Gly Lys Gly
50                  55                  60

Leu Glu Trp Ile Gly Tyr Ile Ser Tyr Ser Gly Ser Thr Ser Tyr Asn

```
            65                  70                  75                  80
Pro Ser Leu Arg Ser Arg Val Thr Ile Ser Arg Asp Thr Ser Lys Asn
                    85                  90                  95

Gln Phe Phe Leu Lys Leu Ser Ser Val Thr Ala Ala Asp Thr Ala Val
                100                 105                 110

Tyr Tyr Cys Ala Arg Arg Gln Val Gly Leu Gly Phe Ala Tyr Trp Gly
                115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser Gln Glu Asp Pro
                275                 280                 285

Glu Val Gln Phe Asn Trp Tyr Val Asp Gly Val Glu Val His Asn Ala
            290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
                420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
    450                 455                 460

<210> SEQ ID NO 17
<211> LENGTH: 445
<212> TYPE: PRT
<213> ORGANISM: Artificial Sequence
```

<220> FEATURE:
<223> OTHER INFORMATION: 313M33 Heavy chain (IgG4) amino acid sequence
without signal sequence

<400> SEQUENCE: 17

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Ser Tyr Asn Pro Ser Leu
    50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
                420                 425                 430
His Tyr Thr Gln Lys Ser Leu Ser Leu Ser Leu Gly Lys
                435                 440                 445

<210> SEQ ID NO 18
<211> LENGTH: 354
<212> TYPE: DNA
<213> ORGANISM: Artificial Sequence
<220> FEATURE:
<223> OTHER INFORMATION: OMP-313M32/313M33 Heavy chain variable region
      nucleotide sequence

<400> SEQUENCE: 18
caggtccagc tgcaggagtc tggcccagga ctggtgaagc cttctgagac cctgtccctc        60
acctgcgctg tctctggtta ctccatcacc tccgattatg cctggaactg gattcggcag       120
cccccaggga aggggctgga gtggattggg tacataagct actctggtag cactagctac       180
aacccatctc tccggtcacg ggtcacaata tcacgggaca catccaagaa ccagttcttc       240
ctgaagctgt cctctgtgac cgccgctgac accgccgtgt attactgtgc aaggagacag       300
gtcgggctgg ggtttgctta ctggggccaa ggaaccctgg tcaccgtcag ctca             354

<210> SEQ ID NO 19
<211> LENGTH: 297
<212> TYPE: DNA
<213> ORGANISM: Artificial Sequence
<220> FEATURE:
<223> OTHER INFORMATION: OMP-313M32/313M33 Light chain variable region
      nucleotide sequence

<400> SEQUENCE: 19
gacatccaga tgacccagtc tccatcctcc ctgtctgcat ctgttggaga cagagtcacc        60
atcacttgca aggcttctca ggatgtgtct actgctgttg cctggtatca gcagaaacca       120
gggaaagccc ctaagctcct gatctactct gcatcctatc ggtacactgg ggtcccatca       180
aggttctccg gatctggatc tgggacagat tttactttca ccatcagcag cctgcagcct       240
gaagatattg caacatatta ctgtcagcaa cattattcta ctccttggac attcggc          297

<210> SEQ ID NO 20
<211> LENGTH: 1404
<212> TYPE: DNA
<213> ORGANISM: Artificial Sequence
<220> FEATURE:
<223> OTHER INFORMATION: OMP-313M32 Heavy chain (IgG1) nucleotide
      sequence

<400> SEQUENCE: 20
atggactgga cctggaggat actctttctc gtggctgcag ccacaggagc ccactcccag        60
gtccagctgc aggagtctgg cccaggactg gtgaagcctt ctgagaccct gtccctcacc       120
tgcgctgtct ctggttactc catcacctcc gattatgcct ggaactggat tcggcagccc       180
ccagggaagg ggctggagtg gattgggtac ataagctact ctggtagcac tagctacaac       240
ccatctctcc ggtcacgggt cacaatatca cgggacacat ccaagaacca gttcttcctg       300
aagctgtcct ctgtgaccgc cgctgacacc gccgtgtatt actgtgcaag gagacaggtc       360
gggctggggt ttgcttactg gggccaagga accctggtca ccgtcagctc agccagcaca       420
```

```
aagggcccct ccgtgttccc tctggcccct cctccaagt ccacctccgg cggcaccgcc    480
gctctgggct gcctggtgaa ggactacttc cctgagcctg tgaccgtgtc ctggaactct    540
ggcgccctga cctctggcgt gcacaccttc ccagccgtgc tgcagtcctc cggcctgtac    600
tccctgtcct ccgtggtgac cgtgccttcc tcctccctgg gcacccagac ctacatctgc    660
aacgtgaacc acaagccttc caacaccaag gtggacaagc gggtggagcc taagtcctgc    720
gacaagaccc acacctgccc tccctgccct gcccctgagc tgctgggcgg accttccgtg    780
ttcctgttcc ctcctaagcc taaggacacc ctgatgatct cccggacccc tgaggtgacc    840
tgcgtggtgg tggacgtgtc ccacgaggat cctgaggtga agttcaattg gtacgtggac    900
ggcgtggagg tgcacaacgc taagaccaag ccaagggagg agcagtacaa ctccacctac    960
cgggtggtgt ctgtgctgac cgtgctgcac caggactggc tgaacggcaa agaatacaag   1020
tgcaaggtct ccaacaaggc cctgcccgct ccatcgaga aaccatctc caaggccaag    1080 ggccagcctc gcgagcctca ggtgtacacc ctgccaccca gccggaggga gatgaccaag   1140
aaccaggtgt ccctgacctg tctggtgaag ggcttctacc cttccgatat cgccgtggag   1200
tgggagtcta acggccagcc cgagaacaac tacaagacca cccctcctgt gctggactcc   1260
gacggctcct tcttcctgta ctccaagctg accgtggaca agtcccggtg gcagcagggc   1320
aacgtgttct cctgctccgt gatgcacgag gccctgcaca accactacac ccagaagagc   1380
ctgtctctgt ctcctggcaa gtga                                          1404

<210> SEQ ID NO 21
<211> LENGTH: 705
<212> TYPE: DNA
<213> ORGANISM: Artificial Sequence
<220> FEATURE:
<223> OTHER INFORMATION: OMP-313M32/313M33 Light chain nucleotide
      sequence

<400> SEQUENCE: 21
atggtgctcc agacccaggt cttcatttcc ctgctgctct ggatcagcgg agcctacggg    60
gacatccaga tgacccagtc tccatcctcc ctgtctgcat ctgttggaga cagagtcacc   120
atcacttgca aggcttctca ggatgtgtct actgctgttg cctggtatca gcagaaacca   180
gggaaagccc ctaagctcct gatctactct gcatcctatc ggtacactgg ggtcccatca   240
aggttctccg gatctggatc tgggacagat tttactttca ccatcagcag cctgcagcct   300
gaagatattg caacatatta ctgtcagcaa cattattcta ctccttggac attcggccaa    360
gggaccaagg tggaaatcaa acgtacggtg gctgcaccat ctgtcttcat cttccctcca    420
tctgatgagc agctcaaatc tggaactgcc tctgttgtgt gcctgctgaa taacttctat    480
cccagagagg ccaaagtcca gtggaaggtg gataacgccc tccaatccgg caactcccag    540
gagagtgtca cagagcagga cagcaaggac agcacctaca gcctcagcaa cacactgaca    600
ctgagcaaag cagactacga aaacacaaa gtctatgcct cgaagtcac ccatcagggc    660 ctgtcttccc ccgtcacaaa gagcttcaac aggggagagt gctaa                   705

<210> SEQ ID NO 22
<211> LENGTH: 1395
<212> TYPE: DNA
<213> ORGANISM: Artificial Sequence
<220> FEATURE:
<223> OTHER INFORMATION: 313M33 Heavy chain (IgG4) nucleotide sequence

<400> SEQUENCE: 22
```

```
atggactgga cctggaggat actctttctc gtggctgcag ccacaggagc ccactcccag    60
gtccagctgc aggagtctgg cccaggactg gtgaagcctt ctgagaccct gtccctcacc   120
tgcgctgtct ctggttactc catcacctcc gattatgcct ggaactggat tcggcagccc   180
ccagggaagg ggctggagtg gattgggtac ataagctact ctggtagcac tagctacaac   240
ccatctctcc ggtcacgggt cacaatatca cgggacacat ccaagaacca gttcttcctg   300
aagctgtcct ctgtgaccgc cgctgacacc gccgtgtatt actgtgcaag agacaggtc   360
gggctggggt ttgcttactg gggccaagga accctggtca ccgtcagctc agccagcaca   420
aagggcccat ccgtcttccc cctggcaccc tgctcccgga gcacctccga gagcacagcc   480
gccctgggct gcctggtcaa ggactacttc cccgaacccg ttaccgtgtc ttggaactcc   540
ggcgcactga ccagcggcgt gcacaccttc cctgctgtcc tccaatcctc tggactctac   600
tccctctcct ccgtggtgac agtgccctcc agcagcctgg gcactaagac ctacacctgc   660
aacgtcgatc acaagcccag caacaccaag gtggacaaga gagttgagtc caaatatgga   720
cccccatgcc caccttgccc agcacctgag ttcctggggg gaccatcagt cttcctgttc   780
cccccaaaac ccaaggacac tctcatgatc tcccggaccc ctgaggtcac ttgcgtggtg   840
gtggacgtga gccaggaaga ccccgaggtc cagttcaact ggtatgtgga tggcgtggag   900
gttcataatg ccaagacaaa gcctcgggag gagcagttca acagcaccta ccgggtggtc   960
agcgtcctca ccgtcctgca ccaagactgg ctgaacggca aggagtacaa gtgcaaggtc  1020
tccaacaaag gctcccatc ctccatcgag aaaaccatct ccaaagccaa agggcagccc  1080
cgggagccac aggtgtacac cctgccccca tcccaagagg agatgaccaa gaaccaagtg  1140
tccctgacct gcctggtcaa aggcttctac cccagcgaca tcgccgtgga gtgggagagc  1200
aatgggcagc ctgagaacaa ctacaagacc actcctcccg tgctggactc cgacggctcc  1260
ttcttcctct actcccggct caccgtggac aagagcaggt ggcaggaggg caatgtcttc  1320
tcctgctccg tgatgcatga ggctctgcac aaccactaca cacagaagag cctctccctg  1380
tctctgggca aatga                                                   1395
```

<210> SEQ ID NO 23
<211> LENGTH: 330
<212> TYPE: PRT
<213> ORGANISM: Artificial Sequence
<220> FEATURE:
<223> OTHER INFORMATION: Human IgG1 Heavy chain constant region

<400> SEQUENCE: 23

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 326
<212> TYPE: PRT
<213> ORGANISM: Artificial Sequence
<220> FEATURE:
<223> OTHER INFORMATION: Human IgG2 Heavy chain constant region

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 25
<211> LENGTH: 377
<212> TYPE: PRT
<213> ORGANISM: Artificial Sequence
<220> FEATURE:
<223> OTHER INFORMATION: Human IgG3 Heavy chain constant region

<400> SEQUENCE: 25

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

```
Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 26
<211> LENGTH: 327
<212> TYPE: PRT
<213> ORGANISM: Artificial Sequence
<220> FEATURE:
<223> OTHER INFORMATION: Human IgG4 Heavy chain constant region

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 27
<211> LENGTH: 16
<212> TYPE: PRT
<213> ORGANISM: Artificial Sequence
<220> FEATURE:
<223> OTHER INFORMATION: Human TIGIT amino acids 55-70

<400> SEQUENCE: 27

Thr Gln Val Asn Trp Glu Gln Gln Asp Gln Leu Leu Ala Ile Cys Asn
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: Human TIGIT amino acids 105-122

<400> SEQUENCE: 28

Glu Tyr Phe Cys Ile Tyr His Thr Tyr Pro Asp Gly Thr Tyr Thr Gly
1               5                   10                  15

Arg Ile

<210> SEQ ID NO 29
<211> LENGTH: 8
<212> TYPE: PRT
<213> ORGANISM: Artificial Sequence
<220> FEATURE:
<223> OTHER INFORMATION: FLAG Tag

<400> SEQUENCE: 29

Asp Tyr Lys Asp Asp Asp Asp Lys
1               5
```